(12) United States Patent
Ojima et al.

(10) Patent No.: US 11,858,880 B2
(45) Date of Patent: *Jan. 2, 2024

(54) ANTI-FUNGALS COMPOUNDS TARGETING THE SYNTHESIS OF FUNGAL SPHINGOLIPIDS

(71) Applicant: THE RESEARCH FOUNDATION FOR THE STATE UNIVERSITY OF NEW YORK, Albany, NY (US)

(72) Inventors: Iwao Ojima, Port Jefferson, NY (US); Maurizio Del Poeta, Mount Sinai, NY (US); Cristina Lazzarini, East Setauket, NY (US); Krupanandan Hanarahalli, Setauket, NY (US); Yi Sun, Mount Sinai, NY (US)

(73) Assignee: THE RESEARCH FOUNDATION FOR THE STATE UNIVERSITY OF NEW YORK, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/837,548

(22) Filed: Jun. 10, 2022

(65) Prior Publication Data

US 2022/0394973 A1 Dec. 15, 2022

Related U.S. Application Data

(62) Division of application No. 16/622,431, filed as application No. PCT/US2018/037846 on Jun. 15, 2018, now Pat. No. 11,414,378.

(60) Provisional application No. 62/521,069, filed on Jun. 16, 2017.

(51) Int. Cl.
| | |
|---|---|
| *C07C 251/86* | (2006.01) |
| *A61P 31/10* | (2006.01) |
| *C07D 213/86* | (2006.01) |
| *C07D 215/54* | (2006.01) |
| *C07D 239/30* | (2006.01) |
| *C07D 307/68* | (2006.01) |
| *C07D 309/08* | (2006.01) |
| *C07D 333/38* | (2006.01) |
| *A01N 37/28* | (2006.01) |
| *A61K 31/195* | (2006.01) |
| *A61K 45/06* | (2006.01) |

(52) U.S. Cl.
CPC ............ *C07C 251/86* (2013.01); *A01N 37/28* (2013.01); *A61K 31/195* (2013.01); *A61P 31/10* (2018.01); *C07D 213/86* (2013.01); *C07D 215/54* (2013.01); *C07D 239/30* (2013.01); *C07D 307/68* (2013.01); *C07D 309/08* (2013.01); *C07D 333/38* (2013.01); *A61K 45/06* (2013.01)

(58) Field of Classification Search
CPC ............................... C07C 251/86; A61P 31/10
See application file for complete search history.

(56) References Cited

U.S. PATENT DOCUMENTS

| | | |
|---|---|---|
| 5,306,712 A | 4/1994 | Tobitsuka |
| 5,786,374 A | 7/1998 | Farooq |
| 5,922,710 A | 7/1999 | Muller |
| 5,932,583 A | 8/1999 | Ziegler |
| 6,211,240 B1 | 4/2001 | Zurfluh |
| 6,232,339 B1 | 5/2001 | Gypser |
| 7,504,362 B2 | 3/2009 | Ekller |
| 7,943,774 B2 | 5/2011 | Cristau |
| 8,063,063 B2 | 11/2011 | Sutton |
| 8,124,616 B2 | 2/2012 | Frechette |
| 8,299,262 B2 | 10/2012 | Grammenos |
| 9,029,549 B2 | 5/2015 | Cristau |
| 9,108,958 B2 | 8/2015 | Ebel |
| 9,215,875 B2 | 12/2015 | Cristau |
| 9,221,827 B2 | 12/2015 | Duffy |
| 9,221,841 B2 | 12/2015 | Hans |
| 9,586,969 B2 | 3/2017 | Bou Hamdan |
| 9,730,447 B2 | 8/2017 | Bereznak |
| 9,896,454 B2 | 2/2018 | Quaranta |
| 10,098,350 B2 | 10/2018 | Bereznak |
| 10,221,171 B2 | 3/2019 | Gestwicki |
| 10,266,544 B2 | 4/2019 | Lee |
| 10,314,820 B2 | 6/2019 | Ander |

(Continued)

FOREIGN PATENT DOCUMENTS

| | | |
|---|---|---|
| WO | WO 2010/083307 A2 | 7/2010 |
| WO | WO 2016/094307 A1 | 6/2016 |
| WO | WO 2016/160552 A1 | 10/2016 |

OTHER PUBLICATIONS

G. L. Backes et al., Synthesis and antifungal activity of substituted salicylaldehyde hydrazones, hydrazides and sulfohydrazides, Bioorganic & Medicinal Chemistry, 2014, 22(17), pp. 4629-4636.

(Continued)

*Primary Examiner* — Golam M Shameem
(74) *Attorney, Agent, or Firm* — Gary J. Gershik

(57) ABSTRACT

The present invention provides a compound having the structure:

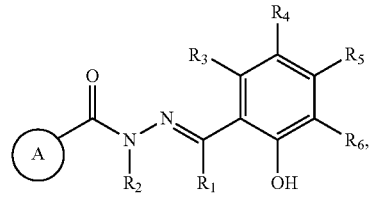

and use of the compound for inhibiting the growth of or killing

20 Claims, 3 Drawing Sheets

(56) References Cited

U.S. PATENT DOCUMENTS

| | | |
|---|---|---|
| 10,407,435 B2 | 9/2019 | Shuttleworth |
| 10,450,279 B2 | 10/2019 | Grammenos |
| 10,570,124 B2 | 2/2020 | Radu |
| 10,646,577 B2 | 5/2020 | Shokat |
| 10,696,634 B2 | 6/2020 | Grammenos |
| 10,906,897 B2 | 2/2021 | Quaranta |
| 10,947,205 B2 | 3/2021 | Mandal |
| 10,947,237 B2 | 3/2021 | Bhattacharjee |
| 10,952,436 B2 | 3/2021 | Quaranta |
| 11,014,889 B2 | 5/2021 | Hoffman |
| 11,053,205 B2 | 7/2021 | Huigens |
| 11,064,697 B2 | 7/2021 | Grammenos |
| 11,414,378 B2 * | 8/2022 | Ojima .................. C07D 333/38 |
| 2012/0010075 A1 | 1/2012 | Young |
| 2012/0027548 A1 | 2/2012 | Whitfield, Jr. et al. |
| 2014/0204859 A1 | 7/2014 | Cordiero et al. |
| 2018/0232298 A1 | 8/2018 | Lopian |
| 2020/0207705 A1 | 7/2020 | Ojima et al. |

OTHER PUBLICATIONS

Feb. 8, 2021 Office Action issued in connection with U.S. Appl. No. 16/622,431.

Feb. 25, 2022 Notice of Allowance issued in connection with U.S. Appl. No. 16/622,431.

Jul. 22, 2021 Office Action issued in connection with U.S. Appl. No. 16/622,431.

Jun. 8, 2021 Response to Feb. 8, 2021 Office Action issued in connection with U.S. Appl. No. 16/622,431.

N. P. Buu-Hoi et al., "Tuberculostatic hydrazides and their derivatives", J. Chem. Soc., 1953, pp. 1358-1364.

Nov. 30, 2020 Response to Sep. 28, 2020 Office Action issued in connection with U. S. Appl. No. 16/622,431.

Oct. 22, 2021 Response to Jul. 22, 2021 Office Action issued in connection with U.S. Appl. No. 16/622,431.

S. Bala et al., "Design, characterization, computational studies, and pharmacological evaluation of substituted-N'-[ (1E) substituted-phenylmethylidene] benzohydrazide analogs", Med. Chem. Res., 2013, 22, pp. 2755-2767.

Sep. 28, 2020 Office Action issued in connection with U.S. Appl. No. 16/622,431.

Y.-X. Feng et al. , "Synthesis, molecular structures, and antimicrobial activities of N'- (3, 5-dibromo-2-hydroXybenzylidene) 2-fluorobenzohydrazide and N'-(4-diethylamino-2 hydroxybenzylidene) -2-fluorobenzohydrazide", J. Chil. Chem. Soc., 2014, 59(3), pp. 2555-2558.

International Search Report dated Sep. 27, 2018 in connection with PCT International Application No. PCT/US2018/037846Journal of Coordination Chemistry, published on Mar. 31, 2014, vol. 67, issue 6, p. 1022-1031.

Written Opinion (form PCT/ISA/237) dated Sep. 27, 2018 in connection with PCT International Application No. PCT/US2018/037846.

S. Bala et al.: "Design, characterization, computational studies, and pharmacological evaluation of substituted-N'-[ (1E) substituted phenylmethylidene] benzohydrazide analogs", Med. Chem. Res., vol. 22, No. 6, Oct. 19, 2013 (Oct. 19, 2013), pp. 2755-2767, XP055557589.

Bhat AK et al.: "Chemotherapy of fungus infections. Ill. Alkyl or aryl thiosemicarbazones, acid hydrazones, and styryl aryl ketones of 5-bromo-and 5-nitrosalicylaldehydes", Indian Journal of Chemistry, Council of Scientific and Industrial Research (C S I R) , IN, vol. 10, No. 7, Jan. 1, 1972 (Jan. 1, 1972), pp. 694-698, XP009525187, ISSN: 0019-5103.

N. P. Buu-Hoi et al.: "278. Tuberculostatic hydrazides and their derivatives", J. Che Soc., 1953, pp. 1358-1364, XP055557591.

Chan et al., A Method for Identifying Small-Molecule Aggregators Using Photonic Crystal Biosensor Microplates JALA, 2009, p. 348-359.

Gawande et al., Synthesis and biological evaluation of azetidinone derivatives from 2-a (phenylacetyl) benzohydrazide moiety by microwave method Der Pharma Chemica, 2014, 6, p. 70-74; 37, p. 606-612.

Li, Synthesis and structures of two molybdenum (VI) complexes derived from similar benzohydrazone ligands with catalytic properties Journal of Coordination Chemistry, published on Mar. 31, 2014, vol. 67, issue 6, p. 1022-1031.

Xue L et al.: "Dioxomolybdenum (VI) complexes derived from tridentate hydrazone ligands: Synthesis, characterization, crystal structures, and antibacterial activity", Russian Journal of Coordination Chemistry, Consultants Bureau, New York, NY, US, vol. 42, No. 2, Mar. 22, 2016 (Mar. 22, 2016), pp. 137-142, XP035650389, ISSN: 1070-3284, DOI: 10.1134/S1070328416020093.

Yuan et al., Syntheses, Characterization, and Crystal Structures of Oxovanadium (V) Complexes with Similar Tridentate Hydrazones Russian Journal of Coordination Chemistry, 2011.

Zhao et al., 1, 8-Naphthalimide-based 'turn-on' fluorescent sensor for the detection of zinc ion in aqueous media and its applications for bioimaging Tet. Lett., 2013, 54, p. 3353-3358).

Datta, K et al., "Spread of Cryptococcus gattii into Pacific Northwest Region of the United States", Emerging Infectious Diseases, 2009, vol. 15, No. 8, pp. 1185-1191.

Dromer, F et al. , "Determinants of Disease Presentation and Outcome during Cryptococcosis: The CryptoA/D Study", PLoS ONE, 2007, vol. 4, No. 2, pp. 297-308.

Dromer, F. et al., "Major Role for Amphotericin B-Flucytosine Combination in Severe Cryptococcosis", PLoS ONE, 2008, vol. 3 No. 8, pp. 1-9.

Hajjeh, R.A. et al., "Cryptococcosis: Population-Based Multistate Active Surveillance and Risk Factors in Human Immunodeficiency Virus-Infected Persons", The Journal of Infectious Diseases, 1999, vol. 179, pp. 449-454.

Heung, L.J. et al., "Role of Sphingolipids in Microbial Pathogenesis", Infection and Immunity, 2006, vol. 74, No. 1, pp. 28-39.

Johnson, M.D and Perfect, J. R., "Caspofungin: first approved agent in a new class of antifungals" Expert Opinion on Pharmacotherapy, 2003, vol. 4, No. 5, pp. 807-823.

Lightowler, J.V.J., et al. , "Treatment of Cryptococcal Meningitis in KwaZulu-Natal, South Africa", PLoS ONE, 2010, vol. 5, vol. 1, pp. 1-5.

Luberto, C et al., "Roles for inositol-phosphoryl ceramide synthase 1 (IPC1) in pathogenesis of C. neoformans", Genes & Development, 2001, vol. 15, pp. 201-212.

McQuiston, T. J et al., "Sphingolipids as Targets for Microbial Infections", Mini-Reviews in Medicinal Chemistry, 2006, vol. 6, pp. 671-680.

Mor V. et al., "Identification of a New Class of Antifungals Targeting the Synthesis of Fungal Sphingolipids", MBio, 2015, vol. 6, No. 3, pp. 1-15.

Mor V. et al., Erratum for Nor et al., "Identification of a New Class of Antifungals Targeting the Synthesis of Fungal Sphingolipids" MBio, 2018, vol. 9, No. 2, pp. 1-2.

Perfect, J.R. et al., "Voriconazole Treatment for Less-Common, Emerging, or Refractory Fungal Infections", Clinical Infectious Diseases, 2003, vol. 36, pp. 1122-1131.

Rhome, R. et al., "Biosynthesis and Immunogenicity of Glucosylceramide in Cryptococcus neoformans and Other Human Pathogens", Eukaryotic Cell, 2007, vol. 6, No. 10, pp. 1715-1726.

Rhome, R. and Poeta, M.D., "Sphingolipid Signaling in Fungal Pathogens", Adv Exp Med Biol, 2010, vol. 688, pp. 232-237.

Rhome, R. et al., "Surface Localization of Glucosylceramide during Cryptococcus neoformans Infection Allows Targeting as a Potential Antifungal", PLoS ONE, 2011, vol. 6, No. 1, pp. 1-13.

Rittershaus P.C., et al., "Glucosylceramide synthase is an essential regulator of pathogenicity of Cryptococcus neoformans", The Journal of Clinical Investigation, 2006, vol. 116, No. 6, pp. 1651-1659.

Shea, J.M. et al., "The Cryptococcal Enzyme Inositol Phosphosphingolipid-Phospholipase C Confers Resistance to the Antifungal Effects of Macrophages and Promotes Fungal Dissemination to the Central Nervous System", Infection and Immunity, 2006, vol. 74, No. 10, pp. 5977-5988.

(56) References Cited

OTHER PUBLICATIONS

Singh, A. et al., "Methylation of glycosylated sphingolipid modulates membrane lipid topography and pathogenicity of Cryptococcus neoformans", Cell Microbiol, 2012, vol. 14, No. 4, pp. 500-516.

Lazzarini, Cristina & Haranahalli, Krupanandan & McCarthy, J. & Mallamo, John & Ojima, Iwao & Poeta, Maurizio. (2020). Preclinical Evaluation of Acylhydrazone SB-AF-1002 as a Novel Broad-Spectrum Antifungal Agent. Antimicrobial Agents and Chemotherapy. 64. 10.1128/AAC. 00946-20.

Lazzarini C, Haranahalli K, Rieger R, Ananthula HK, Desai PB, Ashbaugh A, Linke MJ, Cushion MT, Ruzsicska B, Haley J, Ojima I, Del Poeta M. Acylhydrazones as Antifungal Agents Targeting the Synthesis of Fungal Sphingolipids. Antimicrob Agents Chemother. Apr. 26, 2018; 62 (5) : e00156-18. doi: 10.1128/AAC.00156-18. PMID: 29507066; PMCID: PMC5923120.

Haranahalli K, Lazzarini C, Sun Y, et al. SAR Studies on Aromatic Acylhydrazone-Based Inhibitors of Fungal Sphingolipid Synthesis as Next-Generation Antifungal Agents. J Med Chem. 2019;62 (17 : 8249-8273. doi: 10. 1021/acs. jmedchem. 9b01004.

\* cited by examiner

ANTI-FUNGALS COMPOUNDS TARGETING THE SYNTHESIS OF FUNGAL SPHINGOLIPIDS

CROSS-REFERENCE TO RELATED APPLICATIONS

This application is a divisional of U.S. application Ser. No. 16/622,431, filed Dec. 13, 2019, now allowed, which is a § 371 national stage of PCT International Application No. PCT/US2018/037846, filed Jun. 15, 2018, claiming the benefit of U.S. Provisional Application No. 62/521,069, filed Jun. 16, 2017, the contents of each of which are hereby incorporated by reference.

Throughout, this application, certain publications are referenced in parentheses. Full citations for these publications may be found immediately preceding the claims. The disclosures of these publications in their entireties are hereby incorporated by reference into this application in order to describe more fully the state of the art to which this invention relates.

GOVERNMENT SUPPORT

This invention was made with government support under grant numbers AI116420 and AI100631 awarded by the National Institutes of Health. The government has certain rights in the invention.

BACKGROUND OF THE INVENTION

Globally, over 300 million people are afflicted by a serious fungal infection and 25 million are at risk of dying or losing their sight (Fungal Infection Trust 2011). Among fungal infections, invasive fungal infections such as cryptococcosis, candidiasis, aspergillosis and pneumocystosis are the most common and the most life-threatening (Brown, G. D. et al. 2012; Gullo, A. 2009; Tuite, N. L. & Lacey. K. 2013). These infections have risen dramatically over the last 20 years, some over 14-fold. The CDC estimates that more than 1 million new cases per year of cryptococcosis will occur worldwide in patients with AIDS, and 600,000 will die from the infection. This is a drastic increase considering that prior to the mid-1950s, fewer than 300 cases had been reported in the medical literature (reviewed in Sorrell, T. C. et al. 2011). Certain medical devices, such as catheters, provide the port of entry to fungi that colonize the skin and mucosa. As a result, disseminated candidiasis is the 4th most common hospital-acquired sepsis wroth >120,000 deaths/year (Perlroth, J. et al. 2007; Rueping, M. J. et al. 2009; Guery B. P. et al. 2009). Disseminated aspergillosis represents another invasive fungal infection that is steadily increasing in immunocompromised patients with a mortality rate of 450,000/year (Mayr, A. & Lass-Florl, C. 2011; Maschmeyer, G. et al. 2007; Munoz, P. et al. 2008; Ruping, M. J. et al. 2008). *Aspergillus* spp. is also responsible for severe asthma by fungal sensitization (SAFS) accounting for 100,000 additional deaths annually.

*Pneumocystis* spp. are a group of host-specific opportunistic fungi that reside in the lungs of humans and animals in nature. The organism is named *P. jirovecii* in humans, *P. carinii* in rats, and *P. murina* in mice. *Pneumocystis* pneumonia (PCP) remains the most prevalent opportunistic infection in patients infected with the human immunodeficiency virus (HIV). An estimated 539 million patients were discharged from hospitals between 1986 and 2005, of whom an estimated 312,411 had AIDS-associated PCP. Although numbers of cases of PCP has decreased in economically developed countries, the worldwide incidence is estimated to exceed 400,000 (Kelley, C. F. et al, 2009). Reports on mortality rates for PCP are variable, ranging from 13% to as high as 80%, which even at the lowest rate results in more than 52,000 deaths per year (Kelley, C. F. et al. 2009). PCP is also prevalent in other patient groups, notably patients that are chronically immune suppressed due to solid organ transplantation or due to chemotherapy for cancer or autoimmune disease. *P. jirovecii* (Pj) is also a frequent colonizer of the respiratory tract in immunocompetent individuals with other underlying pulmonary diseases, such as Chronic Obstructive Pulmonary Disease (COPD), in which it initiates a deleterious inflammatory reaction (Huang, L. et al. 2006). Based on these reports, over 1,300,000 people are estimated to die every year because of invasive fungal infections and, most likely, this is an underestimated figure (1, 2). This mortality rate is similar to the one from malaria (1,240,000/year) (WHO World Malaria Report 2013) and tuberculosis (1,400, 000/year) (WHO World Global Tuberculosis 2013).

While there are about 30 branded prescription antifungal drugs on the market, three classes of antifungals are mainly used to manage invasive fungal infections: 1) Azoles, such as fluconazole launched in the mid-1980s, 2) polyenes, such as amphotericin B launched in the mid-1950s and 3) echinocandins, such as caspofungin launched in early 2000. However, the increased use of current azoles has led to an increase in drug resistance, limiting their effectiveness. In addition, drug-drug interaction issues can be a major impediment to the use of voriconazole, itraconazole and posaconazole. The interactions with cancer chemotherapy agents and immunosuppressants can be particularly difficult to handle clinically. Systemic antifungals, such as amphotericin B, tend to have relatively high toxicity and side effects. The echinocandins have a lower incidence of adverse events compared to older antifungals but they bind highly to serum proteins, there are no oral formulations, and their antifungal spectrum of activity is very narrow (Farowski, F. et al. 2012; Farowski, F. et al. 2013; Odabasi, Z. et al. 2007; Saribas, Z. et al. 2012; Yanni, S. B. et al. 2011). In the case of *Pneumocystis*, the situation is direr. *Pneumocystis* pneumonia does not respond to any of the standard antifungals described above (Carmona, E. M. & Limper, A. H. 2011). The drug of choice for the treatment and chemoprophylaxis of PCP is trimethoprim-sulfamethoxazoe (TMP-SMX). Analysis of *P. jirovecii* isolates demonstrates that the pathogen is evolving mutations in the target genes of TMP-SMX, suggesting *P. jirovecii* could soon become resistant to SMX in the combination, considered the more potent of the two drugs that makeup the combination therapy (Ma, L. et al. 1999). Atovaquone and pentamidine, both second line treatments, suffer from low efficacy and severe adverse events (SAEs) that include nephrotoxicity, neutropenia, hypotension and hypoglycemia (Benfield, T. et al. 2008). Atovaquone inhibits the mitochondrial cytochrome Bcl complex in parasites at much lower concentrations than the respective mammalian complex. However, evolving resistance to atovaquone, corresponding to mutations in the *Pneumocystis* cytochrome b gene, has been observed (Kazanjian, P. et al. 2001). Pentamidine has a broad antimicrobial action with no specific target known and is highly toxic and often considered to be a drug of last resort. We are faced, then, with a growing patient population, a microorganism that cannot be easily subjected to detailed biochemical analysis in the laboratory, a developing resistance to standard of care medications and a limited industrial effort to advance new therapies into the clinic. Thus, there is a need for new, safer and more effective compounds.

Studies in our and other laboratories identified sphingolipids as key regulators of fungal pathogenesis (reviewed in Heung, L. J. et al. 2006 and Singh, A. 2011). Particularly, a fungal sphingolipid named glucosylceramide (GlcCer) is required for the pathogenic fungus *Cryptococcus neoformans* to cause a lethal meningo-encephalitis (Kechichian, T. B. et al. 2007; Rittershaus, P. C. et al. 2006). In fact, mice survived the infection by a *C. neoformans* mutant strain lacking the final enzyme for the synthesis of GlcCer (GlcCer synthase 1 or Gcs1). The Δgcs1 mutant was confined in the lung granuloma and it did not reach the bloodstream and, thus, it did not disseminate to the brain. Later, other investigators corroborated and extended our findings that mutation of genes involved in the last steps of the GlcCer pathway affect fungal virulence not only of fungi infecting humans, such as *C. neoformans* (Liu, O. W. et al. 2008; Singh, A. et al. 2012), *Candida albicans* (Oura, T. & Kajiwara, S. 2010; Noble, S. M. et al. 2010; Oura, T. & Kajiwara, S. 2008), and *Aspergillus fumigatus* (Levery, S. B. et al. 2002), but also of fungi infecting plants (da Silva, A. F. et al. 2004; Ramaoorthy, V. et al. 2009). That GlcCer is required for fungal virulence in plants is also suggested by studies showing that plants defend themselves against fungi by producing specific defensins (e.g. RsAFP2 and others) that bind to fungal and not mammalian. GlcCer (Thevissen, K. et al. 2004). Interestingly, these plant defensins are able to bind GlcCer of human pathogenic fungi and able to kill them in vitro and, in some cases, during in vivo infection in animal models (Thevissen, K. 2004; Tavares, P M. 2008; Aerts, A M. 2007; Lobo, D S. 2007; Thevissen, K. 2012; Mello Ede, O. et al. 2014; Oguro, Y. et al. 2014; Goncalves, S. et. al. 2012; de Medeiros, L. N. et al. 2010).

Mechanistic studies revealed that GlcCer is involved in the regulation of fungal cell replication in environments characterized by neutral/alkaline pH (Kechichian, T. B. et al. 2007; Levery, S. B. et al. 2002; Rhome, R. et al. 2011). Particularly, when fungal cells lacking GlcCer are exposed to neutral/alkaline pH, they cannot progress through the cell cycle and, thus, cytokinesis does not occur (Rittershaus, P. C. et. al. 2006; Levery, S. B. et al. 2002; Saito, K. et al. 2006). Later, we linked this phenomenon to the regulation by GlcCer of physical properties of fungal plasma membranes of *C. neoformans* (Singh, A. et al. 2012). The synthesis of GlcCer seems to be important also during *Pneumocystis* pneumonia (PCP) as GlcCer synthase transcripts have been found to be elevated at the time of isolation of the fungus from a fulminate lung infection (Cushion, M. T. et al. 2007). Interestingly, in most dimorphic fungi, production of GlcCer is detected only in the host infective form (yeast) and not in the environmental form (mold) (Warnecke, C. et al. 2003; Rhome, R. et al. 2007; Toledo, M. S. et al. 2001). Taken together, these studies suggest that GlcCer is most likely a pan-fungal virulence factor required during infection to promote fungal growth at neutral/alkaline environments in the host (e.g. alveolar spaces, cerebrospinal fluid and bloodstream), and as such, it is a promising novel drug target. Currently, inhibitors that block the fungal but not the mammalian GlcCer synthesis are not available.

SUMMARY OF THE INVENTION

The present invention provides a compound having the structure:

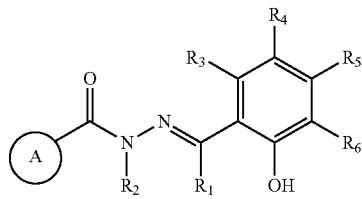

wherein
$R_1$ is —H, alkyl, alkenyl, or alkynyl;
$R_2$ is —H, alkyl, alkenyl, or alkynyl;
$R_3$, $R_4$, $R_5$, and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, or
$R_3$ and $R_4$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_5$ and $R_6$ combine to form a fused aryl or fused heteroaryl, which are each unsubstituted or substituted, or
$R_3$ and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_4$ and $R_5$ combine to form a fused aryl or fused heteroaryl, which are each unsubstituted or substitute, or
$R_5$ and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_3$ and $R_6$ combine to form a fused aryl or fused heteroaryl, which are each unsubstituted or substituted; and
A is an aryl or heteroaryl, which are each unsubstituted or substituted,
wherein when $R_3$, $R_4$, and $R_6$ are each —H and $R_5$ is —OH or —OCH$_3$, or $R_3$, $R_5$, and $R_6$ are each —H and $R_4$ is —Br, then A is other than ortho-tolyl or meta-bromophenyl,
or a pharmaceutically acceptable salt or ester thereof.

DETAILED DESCRIPTION OF THE INVENTION

Figure 1A:
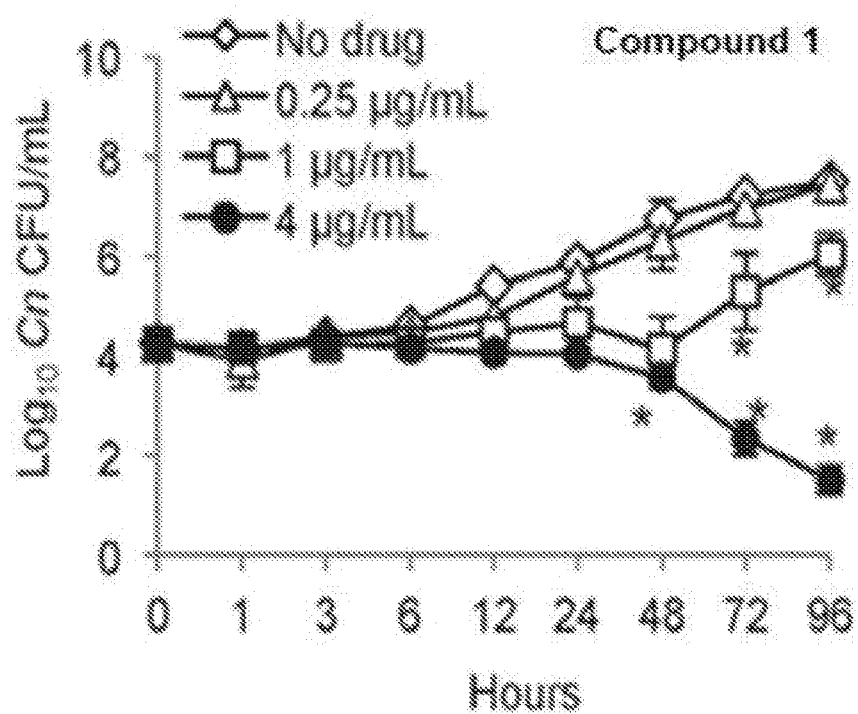
FIG. 1A. Compound 1 killed *C. neoformans* in a concentration dependent manner.

The present invention provides a compound having the structure

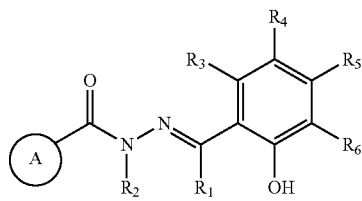

wherein
R₁ is —H, alkyl, alkenyl, or alkynyl;
R₂ is —H, alkyl, alkenyl, or alkynyl;
R₃, R₄, R₅, and R₆ are each independently —H, halogen, C₁-C₆ alkyl, —OH, —O—(C₁-C₆ alkyl), —CHF₂, —CF₃, —OCHF₂ or —OCF₃, or
R₃ and R₄ are each independently —H, halogen, C₁-C₆ alkyl, —OH, —O—(C₁-C₆ alkyl), —CHF₂, —CF₃, —OCHF₂ or —OCF₃, and R₅ and R₆ combine to form a fused aryl or fused heteroaryl, which are each unsubstituted or substituted, or
R₃ and R₆ are each independently —H, halogen, C₁-C₆ alkyl, —OH, —O—(C₁-C₆ alkyl), —CHF₂, —CF₃, —OCHF₂ or —OCF₃, and R₄ and R₅ combine to form a fused aryl or fused heteroaryl, which are each unsubstituted or substitute, or
R₅ and R₆ are each independently —H, halogen, C₁-C₆ alkyl, —OH, —O—(C₁-C₆ alkyl), —CHF₂, —CF₃, —OCHF₂ or —OCF₃, and R₃ and R₄ combine to form a fused aryl or fused heteroaryl, which are each unsubstituted or substituted; and
A is an aryl or heteroaryl, which are each unsubstituted or substituted,
wherein when R₃, R₄, and R₆ are each —H and R₅ is —OH or —OCH₃ or R₃, R₅, and R₆ are each —H and R₄ is —Br, then A is other than ortho-tolyl or meta-bromophenyl,
or a pharmaceutically acceptable salt or ester thereof.

The present invention provides a compound having the structure:

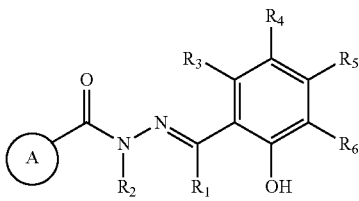

wherein
R₁ is —H;
R₂ is —H;
R₃, R₄, R₅, and R₆ are each independently —H, halogen, C₁-C₆ alkyl, —OH, —O—(C₁-C₆ alkyl), —CHF₂, —CF₃, —OCHF₂ or —OCF₃, or
R₃ and R₄ are each independently —H, halogen, C₁-C₆ alkyl, —OH, —O—(C₁-C₆ alkyl), —CHF₂, —CF₃, —OCHF₂ or —OCF₃, and R₅ and R₆ combine to form a fused aryl or fused heteroaryl, which are each unsubstituted or substituted, or
R₃ and R₆ are each independently —H, halogen, C₃-C₆ alkyl, —OH, —O—(C₁-C₆ alkyl), —CHF₂, —CF₃, —OCHF₂ or —OCF₃, and R₄ and R₅ combine to form a fused aryl or fused heteroaryl, which are each unsubstituted or substitute, or
R₅ and R₆ are each independently —H, halogen, C₁-C₆ alkyl, —OH, —O—(C₁-C₆ alkyl), —CHF₂, —CF₃, —OCHF₂ or —OCF₃, and R₃ and R₄ combine to form a fused aryl or fused heteroaryl, which are each unsubstituted or substituted; and
A is a phenyl, which is unsubstituted or substituted,
wherein when R₃, R₄, and R₆ are each —H and R₅ is —OH or —OCH₃, or R₃, R₅, and R₆ are each —H and R₄ is —Br, then A is other than ortho-tolyl or meta-bromophenyl,
or a pharmaceutically acceptable salt or ester thereof.

The present invention provides a compound having the structure:

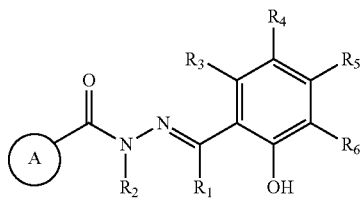

wherein
R₁ is —H;
R₂ is —H;
R₃, R₄, R₅, and R₆ are each independently —H, halogen, C₁-C₆ alkyl, —OH, —O—(C₁-C₆ alkyl), —CHF₂, —CF₃, —OCHF₂ or —OCF₃; and
A is a phenyl, which is unsubstituted or substituted,
wherein when R₃, R₄, and R₆ are each —H and R₅ is —OH or —OCH₃, or R₃, R₅, and R₆ are each —H and R₄ is —Br, then A is other than ortho-tolyl or meta-bromophenyl,
or a pharmaceutically acceptable salt or ester thereof.

The present invention provides a compound having the structure:

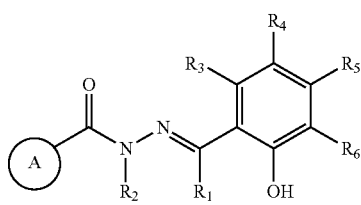

wherein
R₁ is —H;
R₂ is —H;
R₃, R₄, R₅, and R₆ are each independently —H, halogen, C₁-C₆ alkyl, —OH, —O—(C₁-C₆ alkyl), —CHF₂, —CF₃, —OCHF₂ or —OCF₃; and
A is a phenyl, which disubstituted,
or a pharmaceutically acceptable salt or ester thereof.

The present invention provides a compound having the structure:

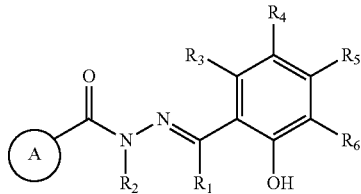

wherein
R₁ is —H;
R₂ is —H;
R₃, R₄, R₅, and R₆ are each independently —H, halogen, C₁-C₆ alkyl, —OH, —O—(C₁-C₆ alkyl), —CHF₂, —CF₃, —OCHF₂ or —OCF₃; and A is a phenyl, which trisubstituted,
or a pharmaceutically acceptable salt or ester thereof.

In some embodiments, wherein when $R_3$ and $R_5$ are each —H and $R_4$ and $R_6$ are each —Br, then A is other than para-bromophenyl, meta-bromophenyl, ortho-tolyl or 3-quinolinyl.

In some embodiments, wherein when $R_3$, $R_5$ and $R_6$ are each —H and $R_4$ is —Br, then A is other than 3,5-dibromo-ortho-hydorxyphenyl, para-bromophenyl, meta-bromophenyl or ortho-tolyl.

In some embodiments, wherein when $R_3$ and $R_5$ are each —H and $R_4$ and $R_6$ are each —Br, then A is other than para-bromophenyl, meta-bromophenyl, ortho-tolyl or 3-quinolinyl; and when $R_3$, $R_5$ and $R_6$ are each —H and $R_4$ is —Br, then A is other than 3,5-dibromo-ortho-hydorxy, para-bromophenyl, meta-bromophenyl or ortho-tolyl.

In some embodiments, wherein when $R_3$ and $R_5$ are each —H and $R_4$ and $R_6$ are each —Br, then A is other than para-bromophenyl; and when $R_3$, $R_5$ and $R_6$ are each —H and $R_4$ is —Br, then A is other than 3,5-dibromo-ortho-hydorxyphenyl.

In some embodiments, A is other than para-bromophenyl, meta-bromophenyl, ortho-tolyl or 3-quinolinyl.

In some embodiments, A is other than 3,5-dibromo-ortho-hydorxyphenyl, para-bromophenyl, meta-bromophenyl or ortho-tolyl In some embodiments, A is other than ortho-tolyl or meta-bromophenyl.

In some embodiments, A is other than 3,5-dibromo-ortho-hydorxyphenyl, para-bromophenyl, meta-bromophenyl, ortho-tolyl or 3-quinolinyl.

In some embodiments, wherein the aryl or heteroaryl is substituted with halogen, $C_1$-$C_6$ alkyl, —OH, —O—($C_1$-$C_6$ alkyl), —CHF$_2$, —CF$_3$, —OCHF$_2$ or —OCF$_3$.

In some embodiments, wherein the fused aryl or fused heteroaryl is substituted with halogen, $C_1$-$C_6$ alkyl, —OH, —O—($C_1$-$C_6$ alkyl), —CHF$_2$, —CF$_3$, —OCHF$_2$ or —OCF$_3$.

In some embodiments, the compound wherein one of $R_3$-$R_6$ is other than —H.

In some embodiments, the compound wherein two of $R_3$-$R_6$ is other than —H.

In some embodiments, the compound, wherein A is monosubstituted.

In some embodiments, the compound wherein A is disubstituted.

In some embodiments, the compound wherein A is trisubstituted.

In some embodiments, the compound wherein $R_3$, $R_4$, $R_5$, and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$.

In some embodiments, the compound wherein $R_3$, $R_4$, $R_5$, and $R_6$ are each independently halogen, —O—($C_1$-$C_6$ alkyl), —OCF$_3$ or —CF$_3$.

In some embodiments, the compound wherein $R_3$, $R_4$, $R_5$, and $R_6$ are each independently halogen or —O—($C_1$-$C_6$ alkyl).

In some embodiments, the compound wherein $R_3$, $R_4$, $R_5$, and $R_6$ are each independently —Cl, —Br, —F, —O—($C_1$-$C_6$ alkyl), —OCF$_3$ or —CF$_3$.

In some embodiments, the compound wherein $R_3$, $R_4$, $R_5$, and $R_6$ are each independently —Cl, —Br, or —O—($C_1$-$C_6$ alkyl).

In some embodiments, the compound wherein
$R_3$ is —H, $R_4$ is —CH$_3$, Cl or Br, $R_5$ is —H, and $R_6$ is —CH$_3$, Cl or Br; or $R_3$ is —H, $R_4$ is —CH$_3$, Cl or Br, $R_5$ is and $R_6$ is H; or
$R_3$ is —H, $R_4$ is —H, $R_5$ is —CH$_3$, Cl or Br, and $R_6$ is —H.

In some embodiments, the compound having the structure:

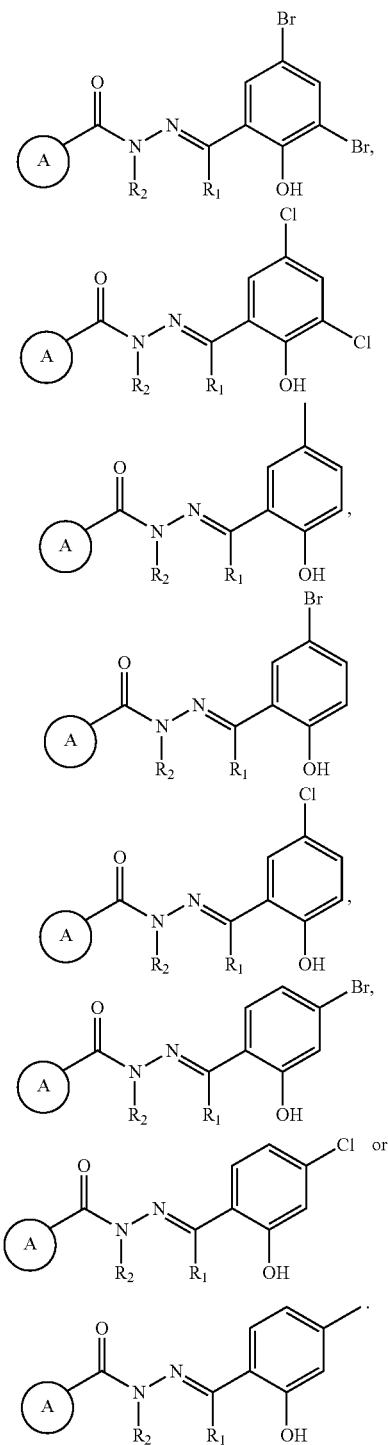

In some embodiments, the compound wherein
$R_3$ is —H, $R_4$ is —F, —OCF$_3$ or —CF$_3$, $R_5$ is —H, and $R_6$ is —H; or
$R_3$ is —H, $R_4$ is —H, $R_5$ is —H, and $R_6$ is Cl or Br.

In some embodiments, the compound having the structure:

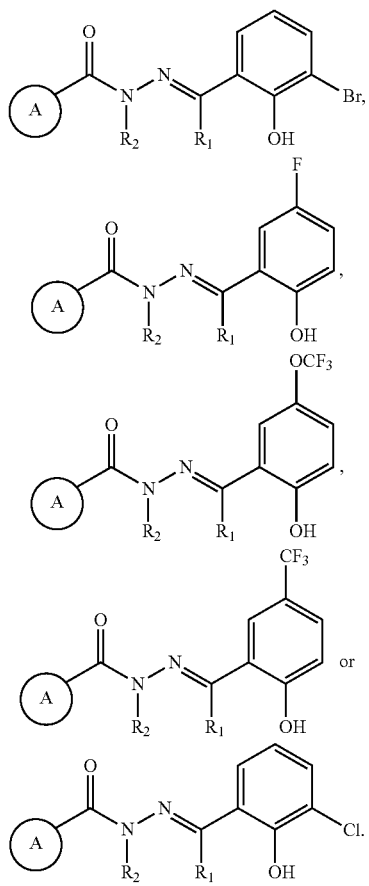

In some embodiments, the compound wherein $R_3$ and $R_4$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_5$ and $R_6$ combine to form a fused aryl or fused heteroaryl, which are each unsubstituted or substituted with halogen, $C_1$-$C_6$ alkyl, —OH, —O—($C_1$-$C_6$ alkyl), —CHF$_2$, —CF$_3$, —OCHF$_2$ or —OCF$_3$.

In some embodiments, the compound wherein $R_3$ and $R_4$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_5$ and $R_6$ combine to form a fused unsubstituted phenyl.

In some embodiments, the compound wherein $R_3$ and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_4$ and $R_5$ combine to form a fused aryl or fused heteroaryl, which are each unsubstituted or substituted with halogen, $C_1$-$C_6$ alkyl, —OH, —O—($C_1$-$C_6$ alkyl), —CHF$_2$, —CF$_3$, —OCHF$_2$ or —OCF$_3$.

In some embodiments, the compound wherein $R_3$, and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_4$ and $R_5$ combine to form a fused unsubstituted phenyl.

In some embodiments, the compound wherein $R_5$ and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_3$ and $R_4$ combine to form a fused aryl or fused heteroaryl, which are each unsubstituted or substituted with halogen, $C_1$-$C_6$ alkyl, —OH, —O—($C_2$-$C_6$ alkyl), —CHF$_2$, —CF$_3$, —OCHF$_2$ or —OCF$_3$.

In some embodiments, the compound wherein $R_5$ and $R_6$ are each independently —H, halogen, $C_1$-$C_6$ alkyl, —OH, —O—($C_1$-$C_6$ alkyl), —CHF$_2$, —CF$_3$, —OCHF$_2$ or —OCF$_3$, and $R_3$ and $R_4$ combine to form a fused unsubstituted phenyl.

In some embodiments, the compound having the structure:

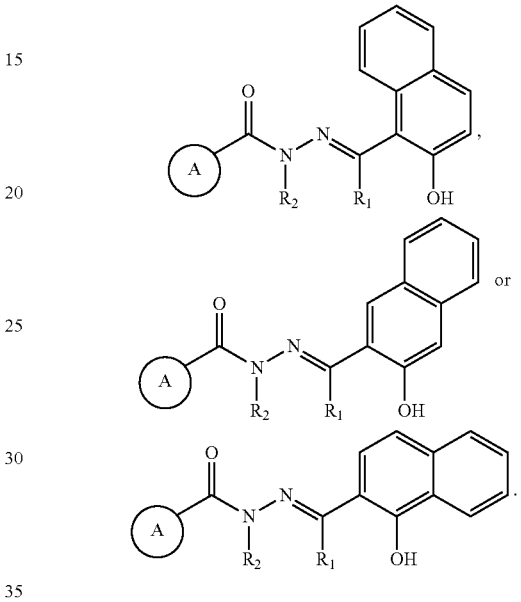

In some embodiments, the compound wherein A is an unsubstituted aryl.

In some embodiments, the compound wherein A is a substituted aryl.

In some embodiments, the compound wherein A is an unsubstituted heteroaryl.

In some embodiments the compound wherein A is an substituted heteroaryl.

In some embodiments, the compound wherein the aryl is a phenyl, 1-naphthyl or 2-naphthyl.

In some embodiments, the compound wherein the heteroaryl is a pyridinyl, pyrrolyl, thienyl, furyl, quinolyl, isoquinolyl, indolyl, benzothienyl or benzofuryl.

In some embodiments, the compound wherein A has the structure:

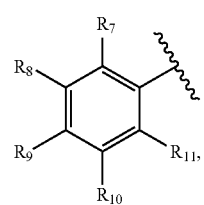

wherein $R_7$, $R_8$, $R_9$, $R_{10}$ and $R_{11}$ are each, independently, —H, halogen, $C_1$-$C_6$ alkyl, —OH, —O—($C_1$-$C_6$ alkyl), —CHF$_2$, —CF$_3$, —OCHF$_2$, —OCF$_3$, —CN, —CH$_2$OCH$_3$, —N(CH)$_2$, —CH$_2$F, —N$_3$ or —CCH.

In some embodiments, the compound wherein A has the structure:

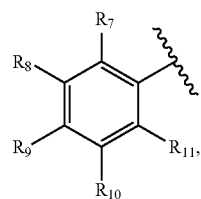

wherein $R_7$, $R_8$, $R_9$, $R_{10}$ and $R_{11}$ are each, independently, —H, halogen, $C_1$-$C_6$ alkyl, —OH, —O—($C_1$-$C_6$ alkyl), —CHF$_2$, —CF$_3$, —OCHF$_2$ or —OCF$_3$.

In some embodiments, the compound wherein $R_7$, $R_8$, $R_9$, $R_{10}$ and $R_{11}$ are each, independently, halogen or —O—($C_1$-$C_6$ alkyl).

In some embodiments, the compound wherein $R_7$, $R_8$, $R_9$, $R_{10}$ and $R_{11}$ are each, independently, —Cl, —Br, or —O—($C_1$-$C_6$ alkyl).

In some embodiments, the compound wherein one of $R_7$ or $R_{11}$ is —H.

In some embodiments, the compound wherein A has the structure:

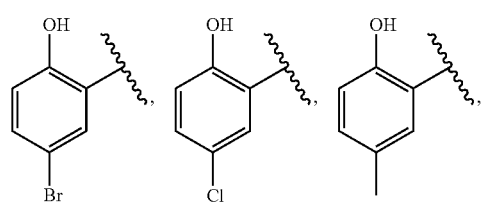

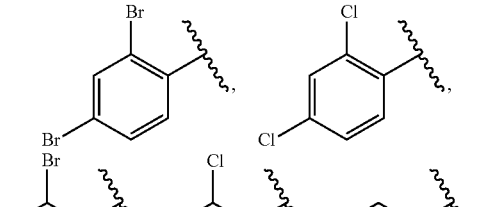

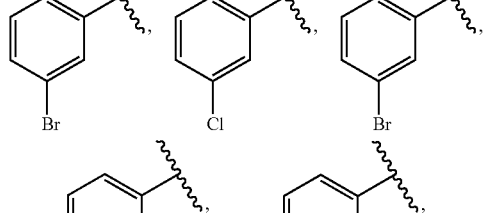

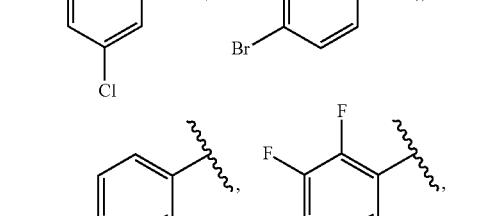

-continued

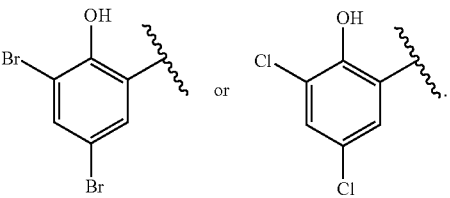

In some embodiments, the compound wherein A has the structure:

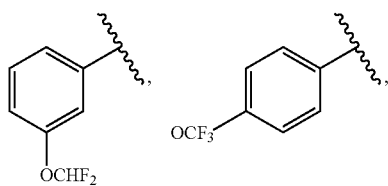

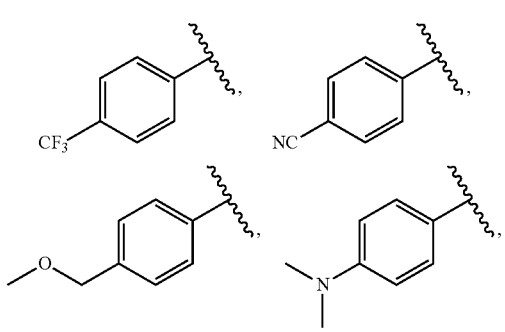

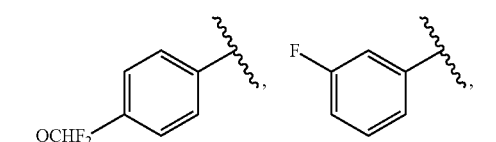

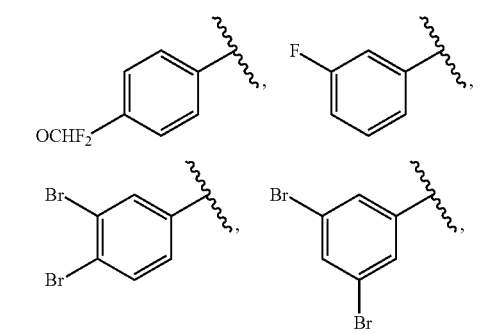

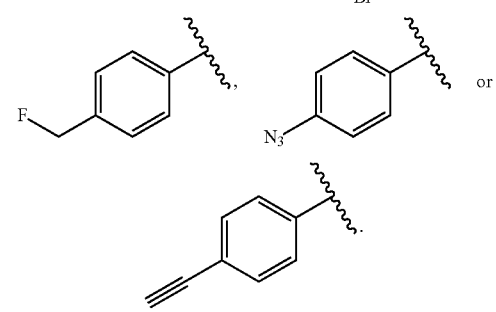

In some embodiments, the compound wherein A has the structure:
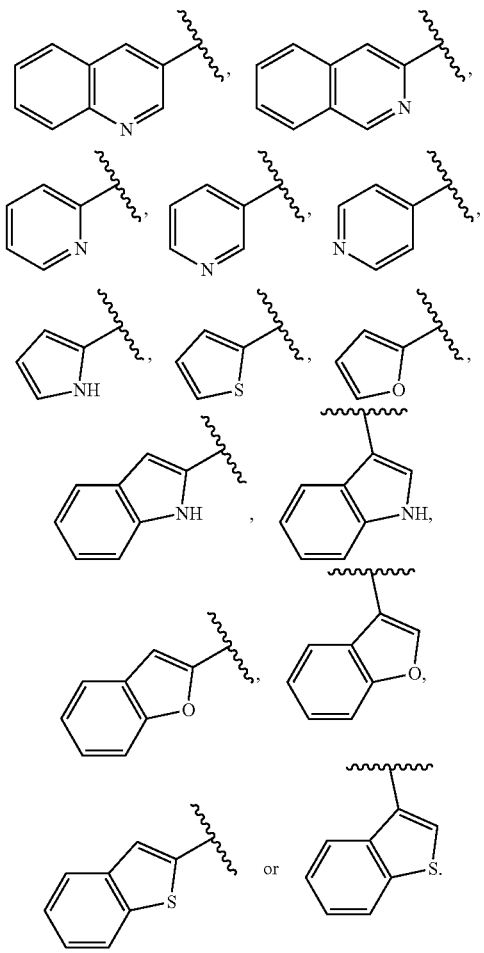
In some embodiments, the compound wherein A has the structure:
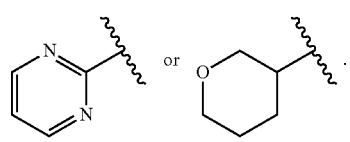 [SMILES: *c1ncccn1 ; *C1CCCOC1]
In some embodiments, the compound having the structure:
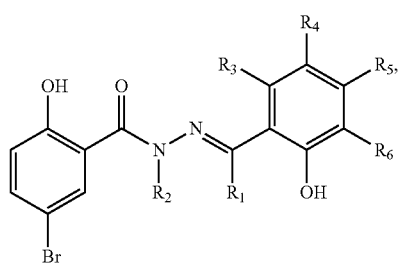
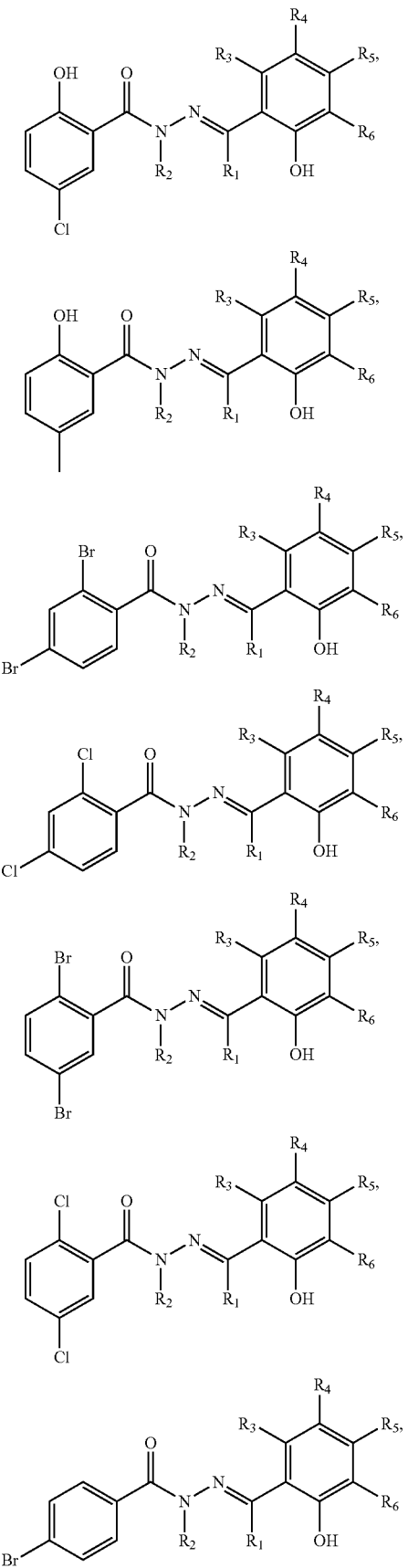

-continued
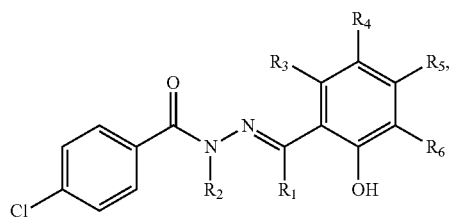
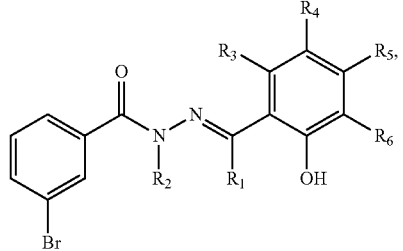
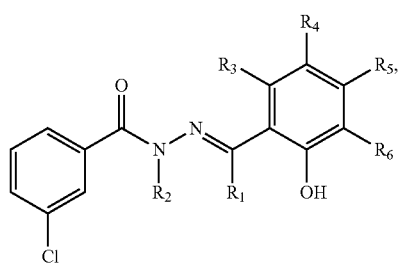
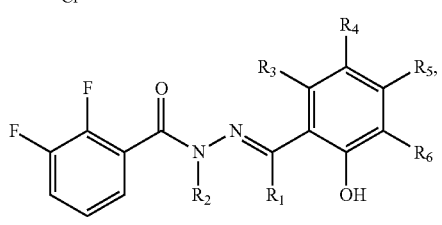
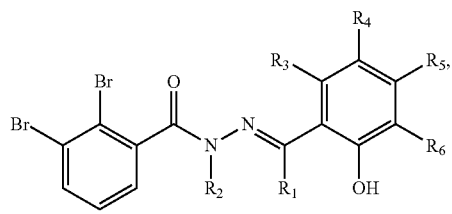
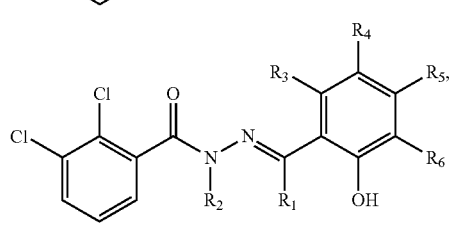
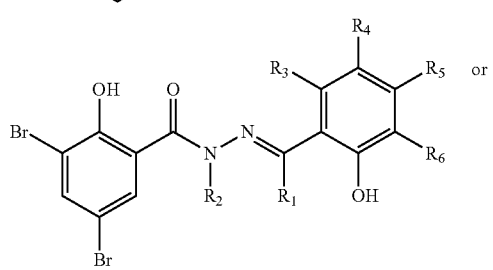 or
-continued
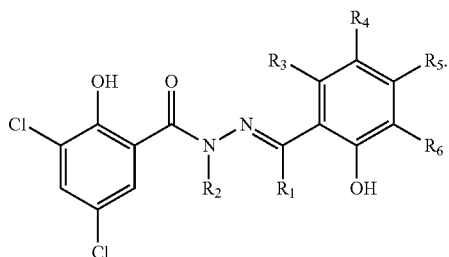
In some embodiments, the compound wherein $R_1$ is —H or —CH$_3$; and $R_2$ is —H or —CH$_3$. In some embodiments, the compound wherein $R_1$ is —H; and $R_2$ is —H.
In some embodiments, the compound having the structure:
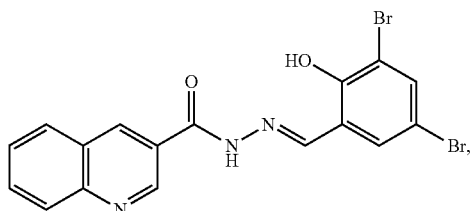
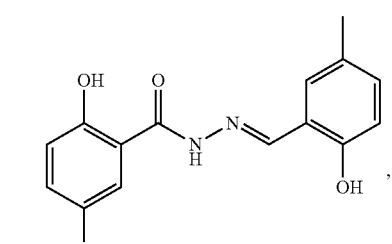
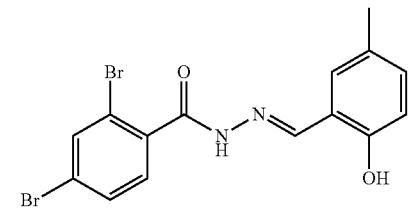
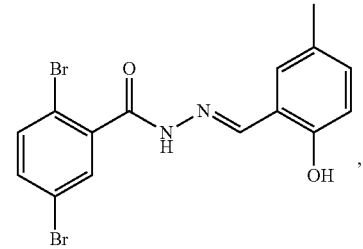
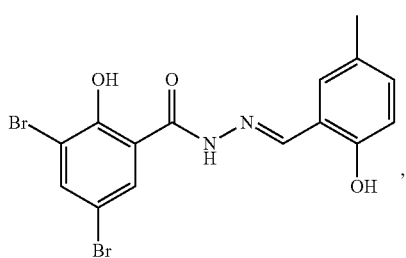

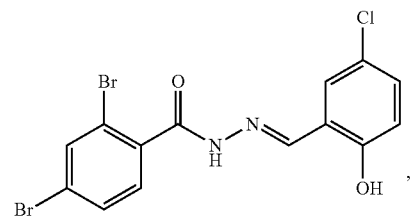
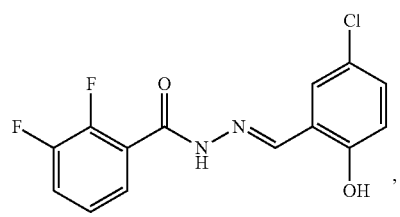
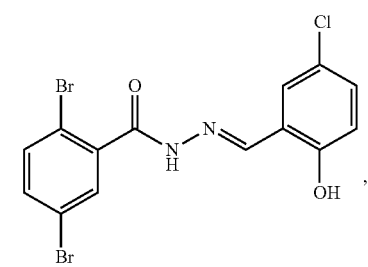
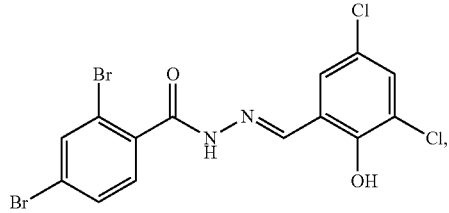
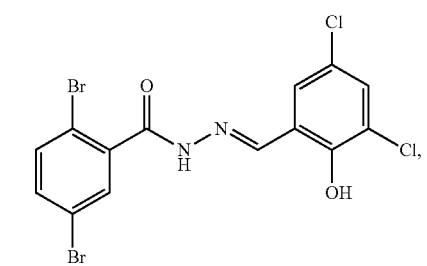
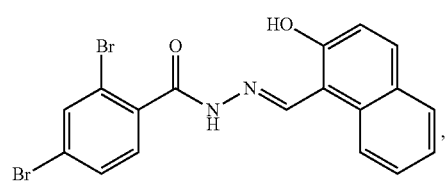
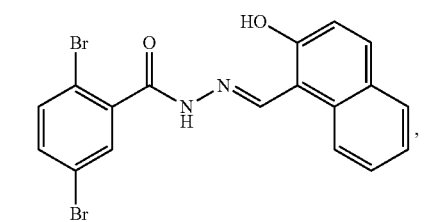
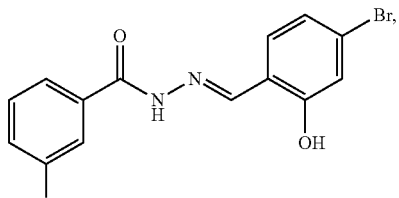
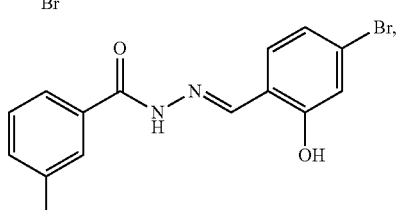
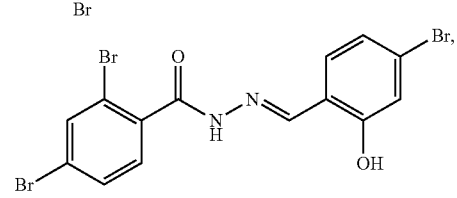
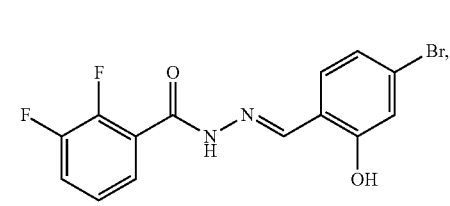
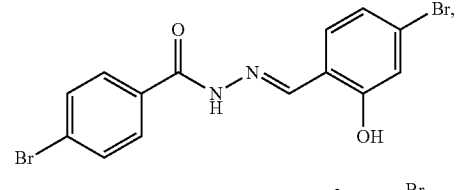
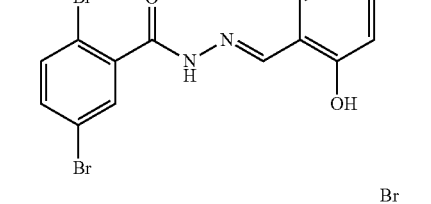
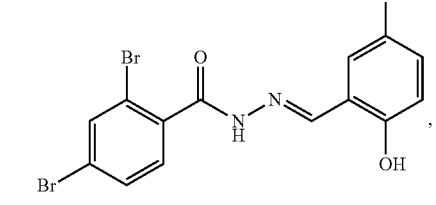
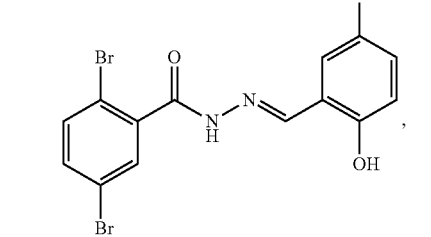

-continued
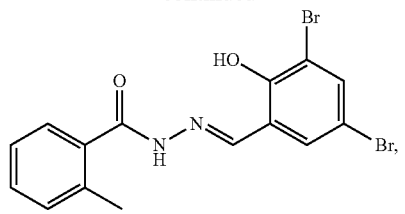
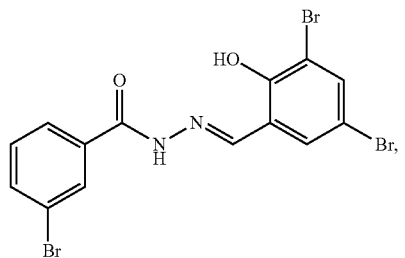
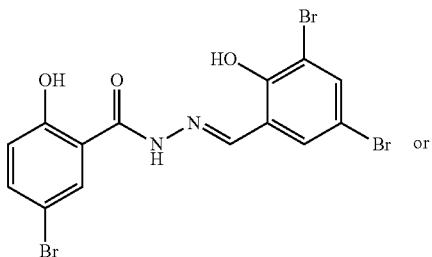 or
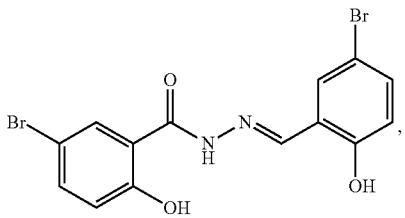,
or a pharmaceutically acceptable salt or ester thereof.
In some embodiments, the compound having the structure
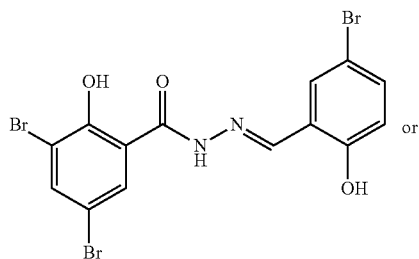 or
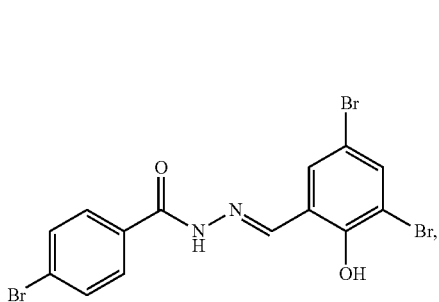
or a pharmaceutically acceptable salt or ester thereof.
In some embodiments, the compound having the structure:
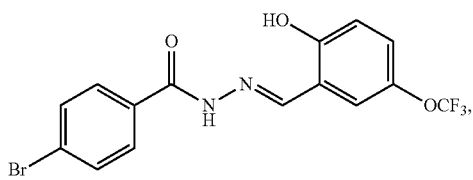
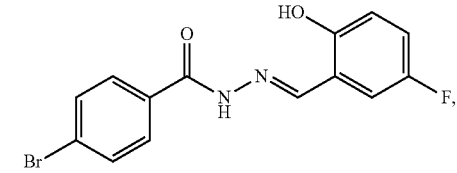
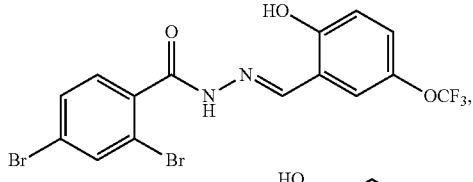
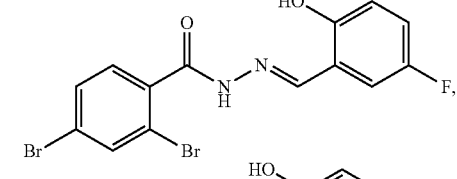
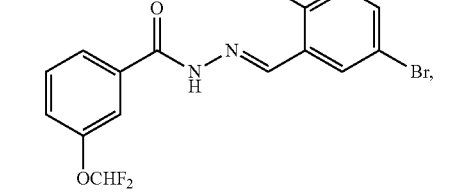
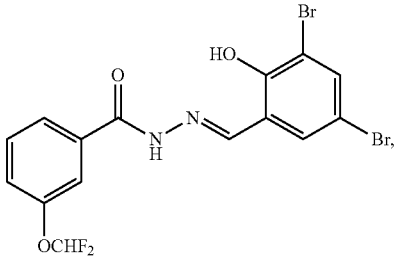
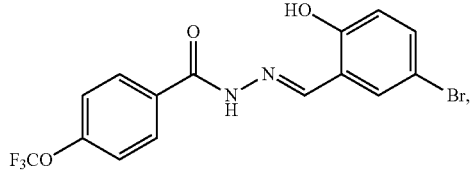
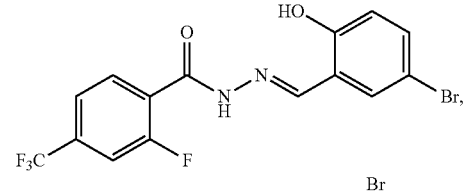
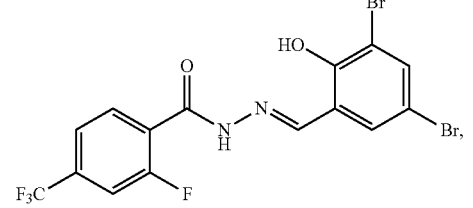

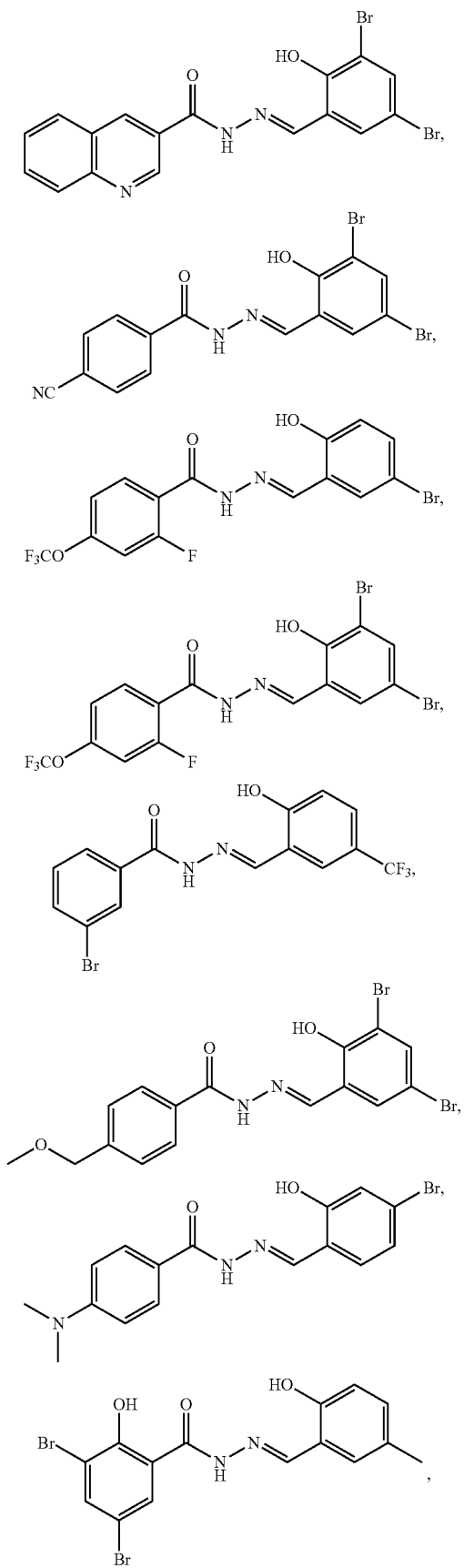
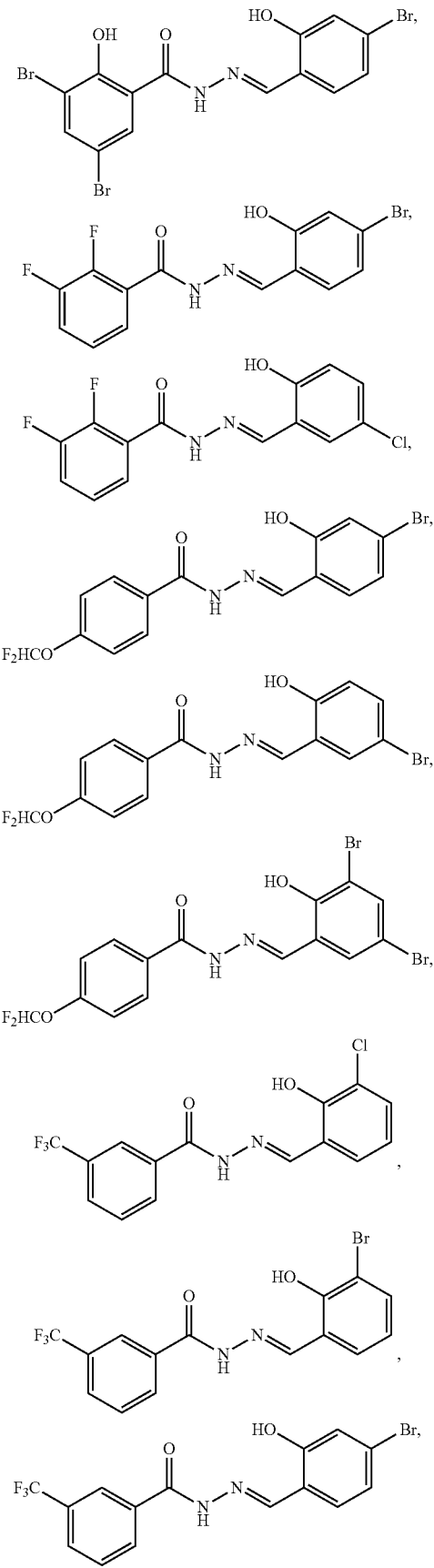

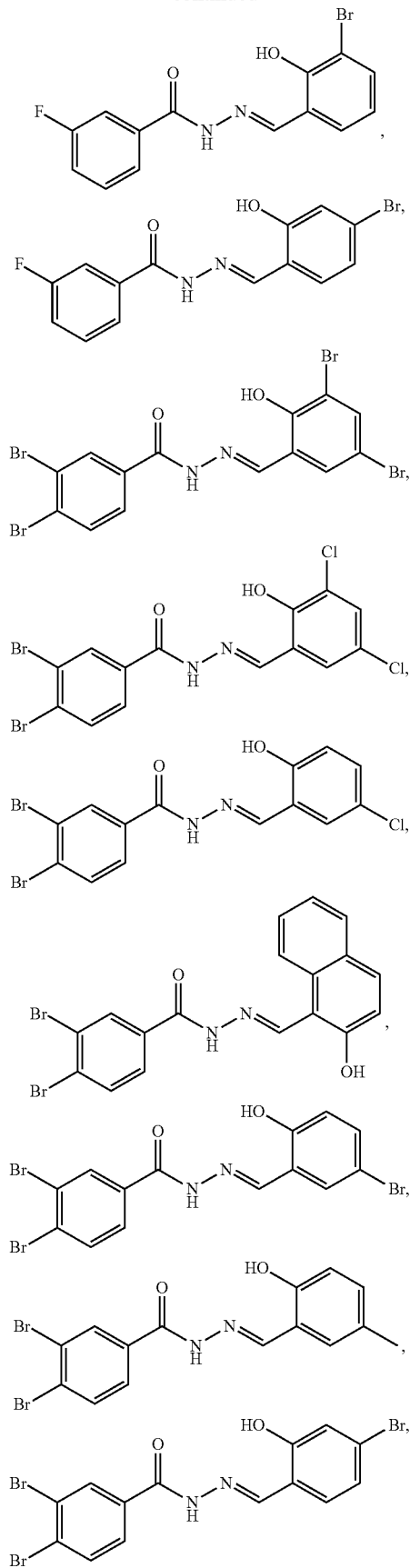
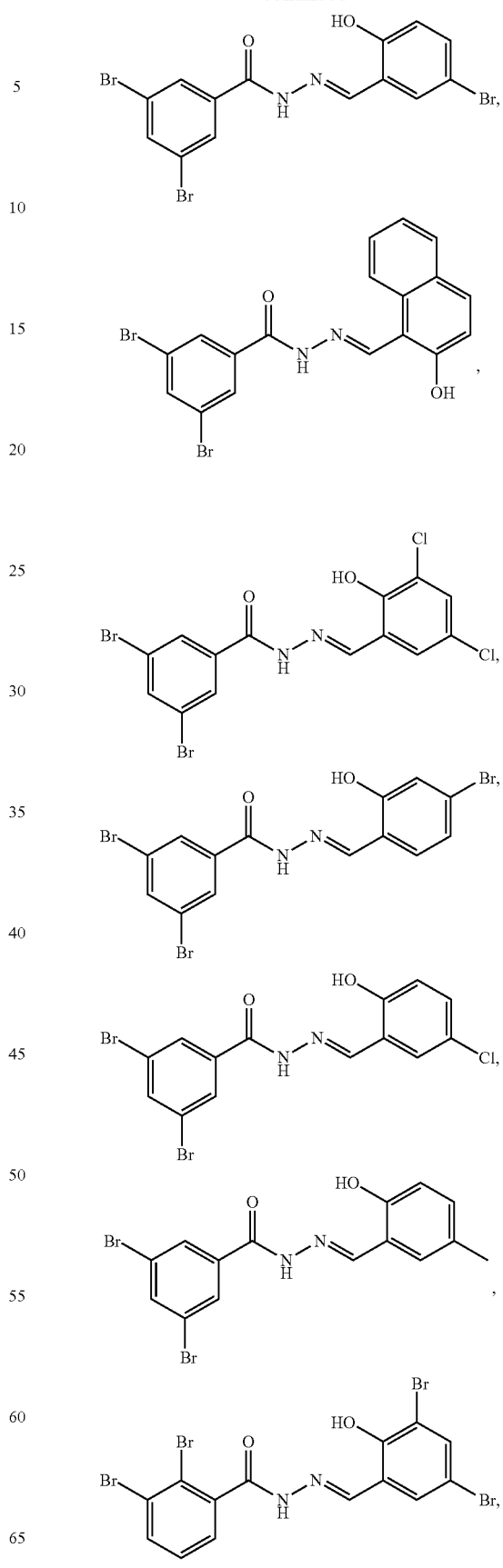

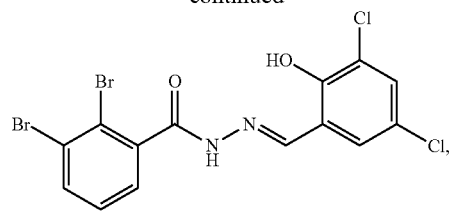
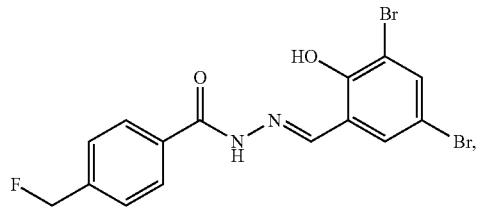
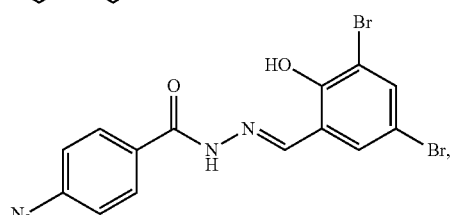
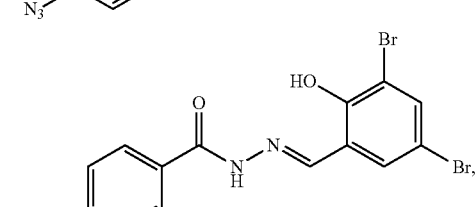
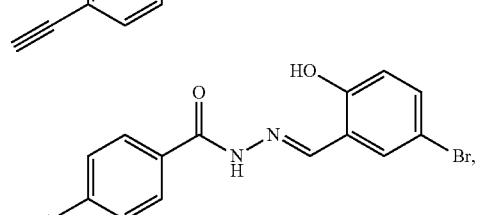
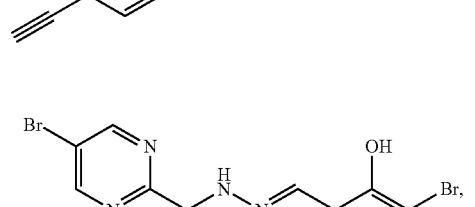
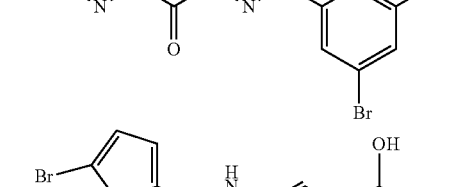
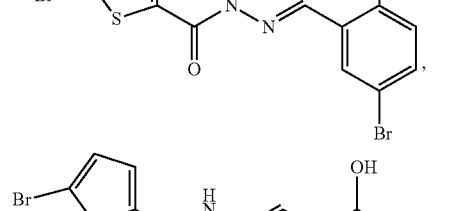
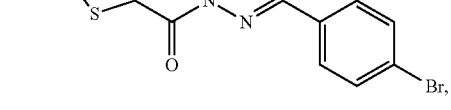
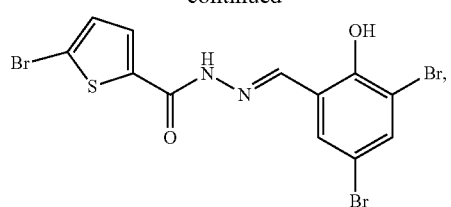
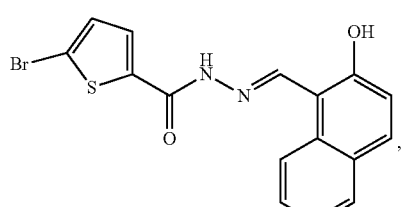
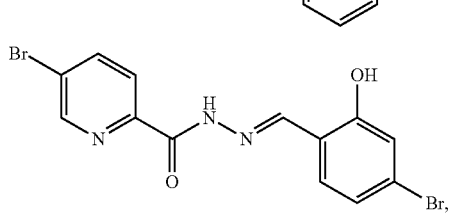
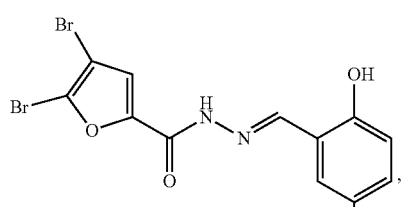
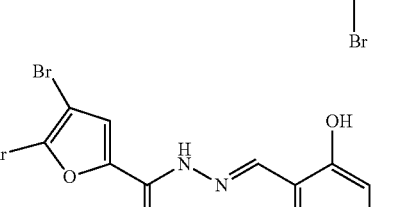
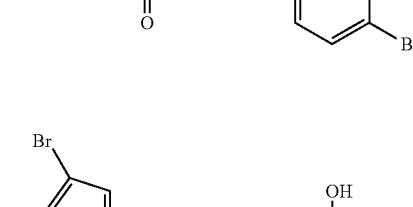
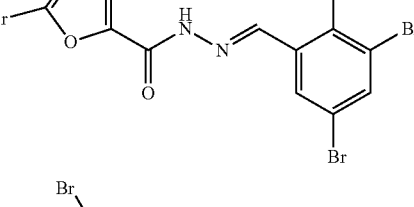
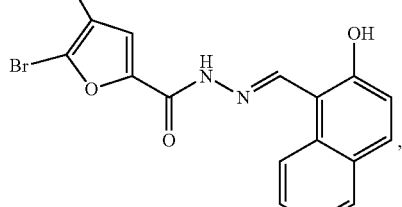

-continued

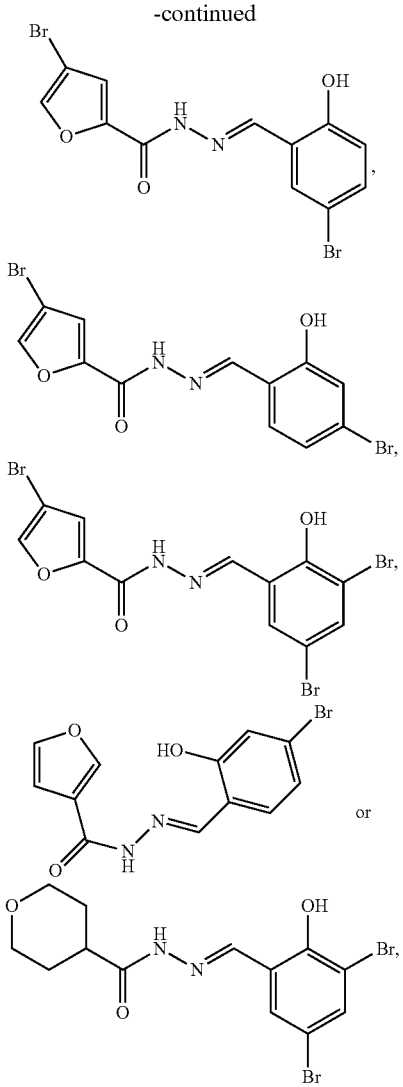

or a pharmaceutically acceptable salt or ester thereof.

In some embodiments, a pharmaceutical composition comprising the compound of the present invention and a pharmaceutically acceptable carrier.

In some embodiments, a pharmaceutical composition comprising the compound of the present invention, an anti-fungal agent and a pharmaceutically acceptable carrier.

In some embodiments, a pharmaceutical composition the anti-fungal agent is fluconazole, amphotericin B, caspofungin, tunicamycin or aureobasidin A.

The present invention provides a method of inhibiting the growth of a fungus comprising contacting the fungus with an effective amount of the compound of the present invention or a pharmaceutically acceptable salt or ester thereof, so as to thereby inhibit the growth of the fungus.

The present invention also provides a method of inhibiting fungal sphingolipid synthesis in a fungus comprising contacting the fungus with an effective amount of the compound of the present invention or a pharmaceutically acceptable salt or ester thereof, so as to thereby inhibit sphingolipid synthesis in the fungus.

The present invention further provides a method of inhibiting fungal sphingolipid synthesis in a fungus in a mammal without substantially inhibiting mammalian sphingolipid synthesis comprising administering to the mammal an effective amount of the compound of the present invention or a pharmaceutically acceptable salt or ester thereof, so as to thereby inhibit fungal sphingolipid synthesis in the fungus in the mammal without substantially inhibiting mammalian sphingolipid synthesis.

In some embodiments of the method, the compound has the structure:

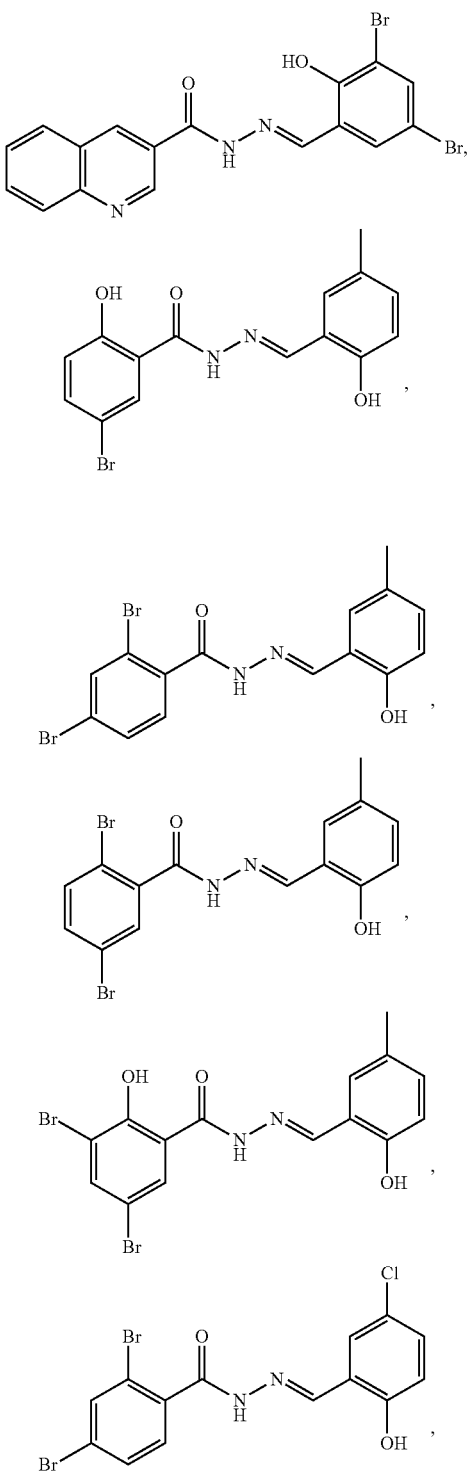

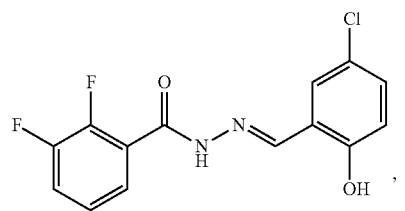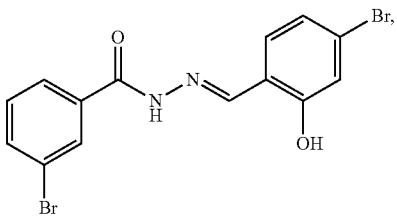

-continued
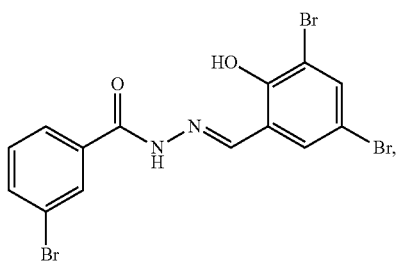
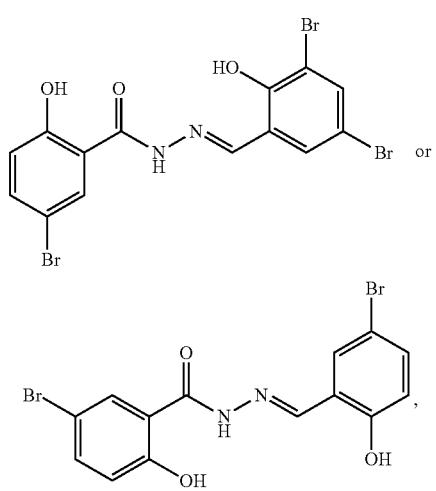
or a pharmaceutically acceptable salt thereof.
In some embodiments of the method, the compound has the structure:
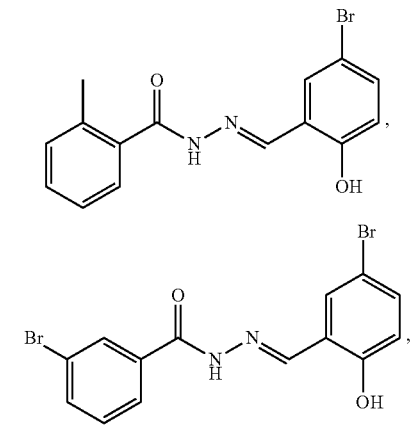
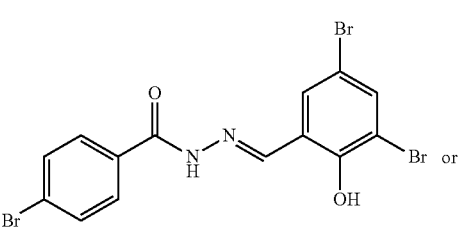
-continued
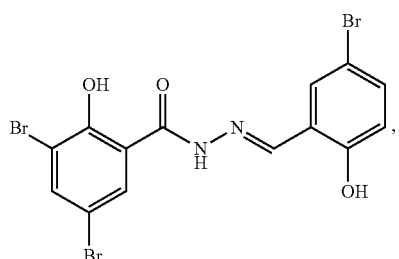
or a pharmaceutically acceptable salt thereof.
In some embodiments of the method, the compound has the structure:
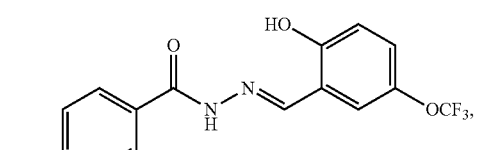
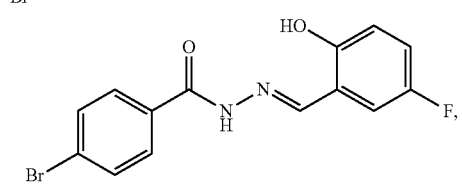
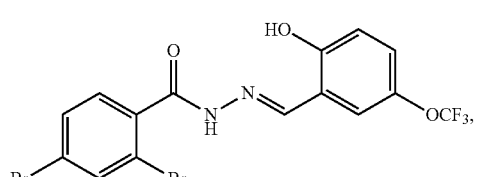
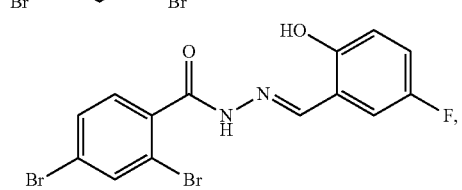
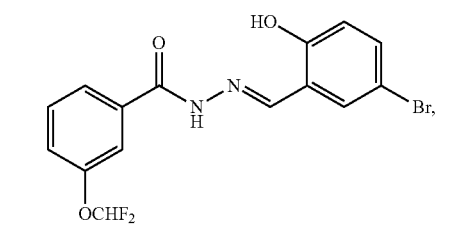
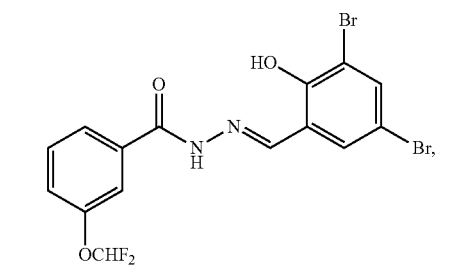

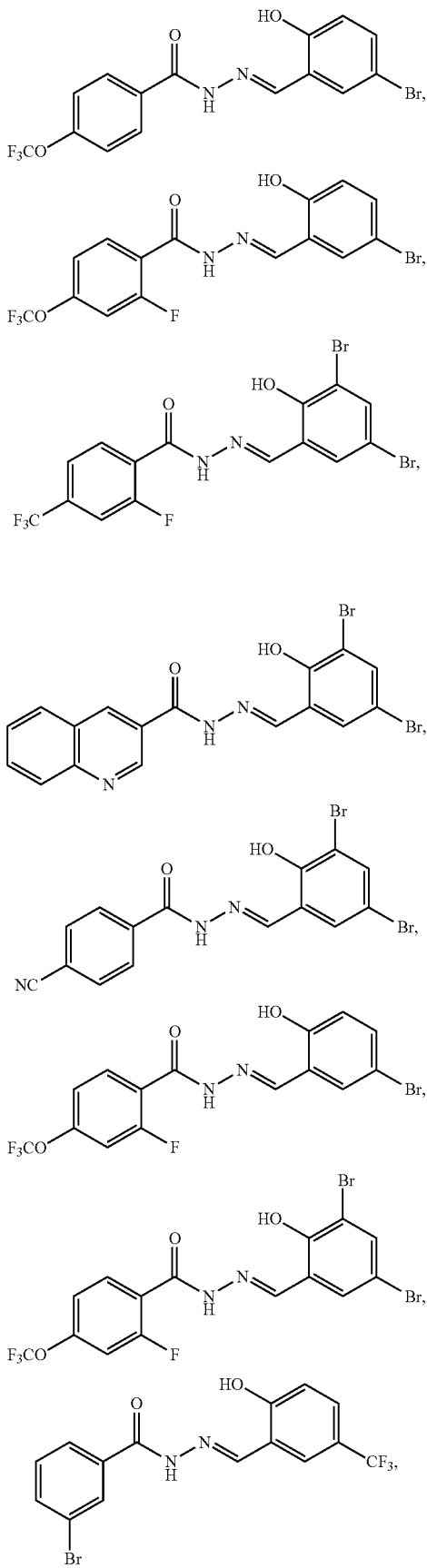
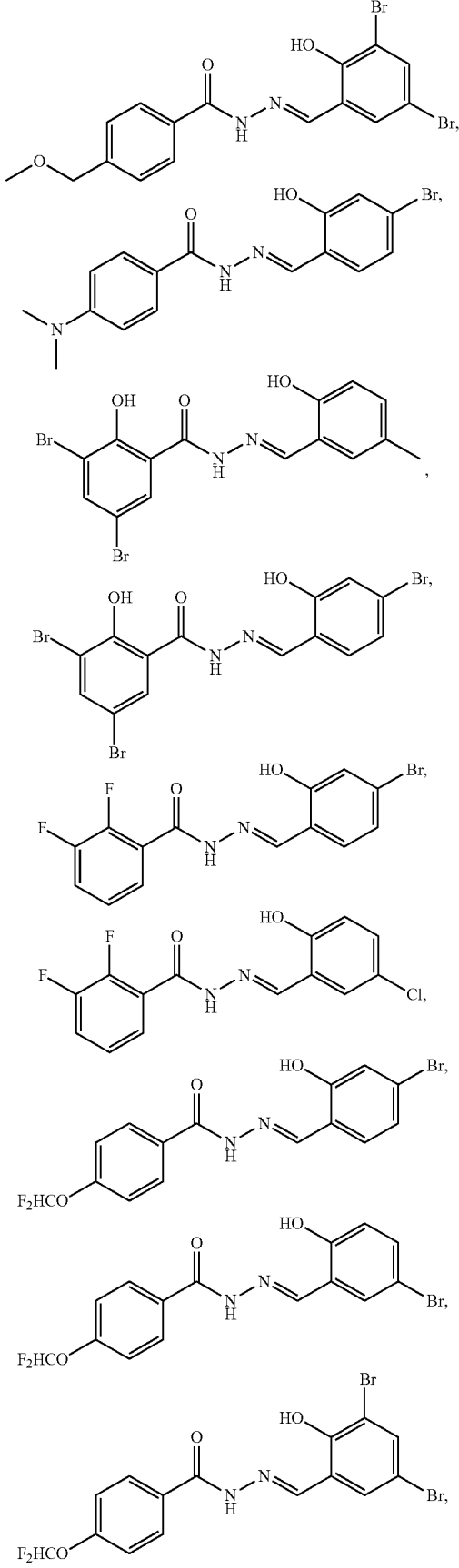

-continued
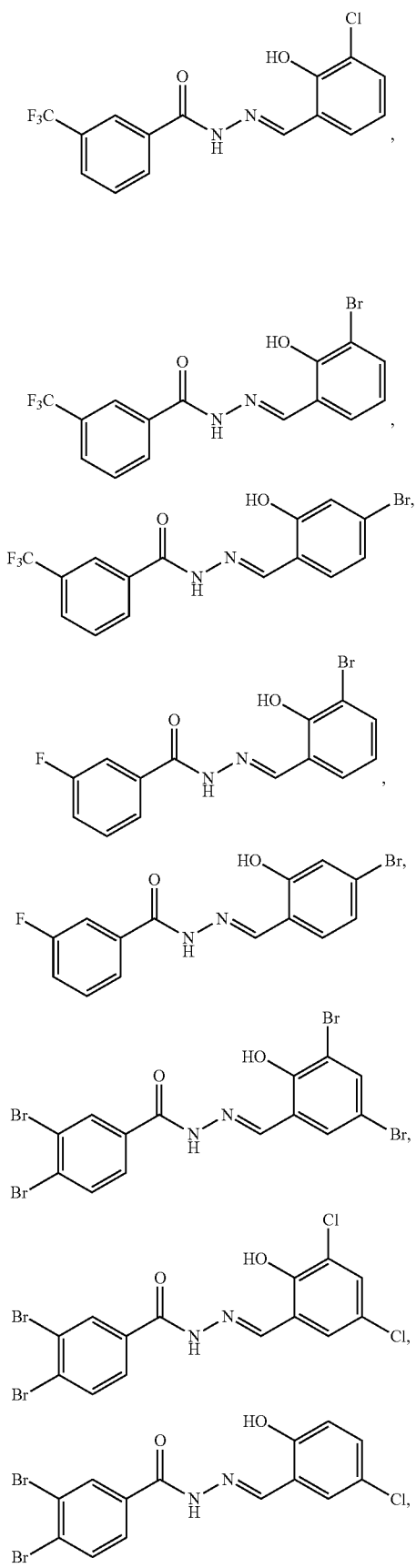
-continued
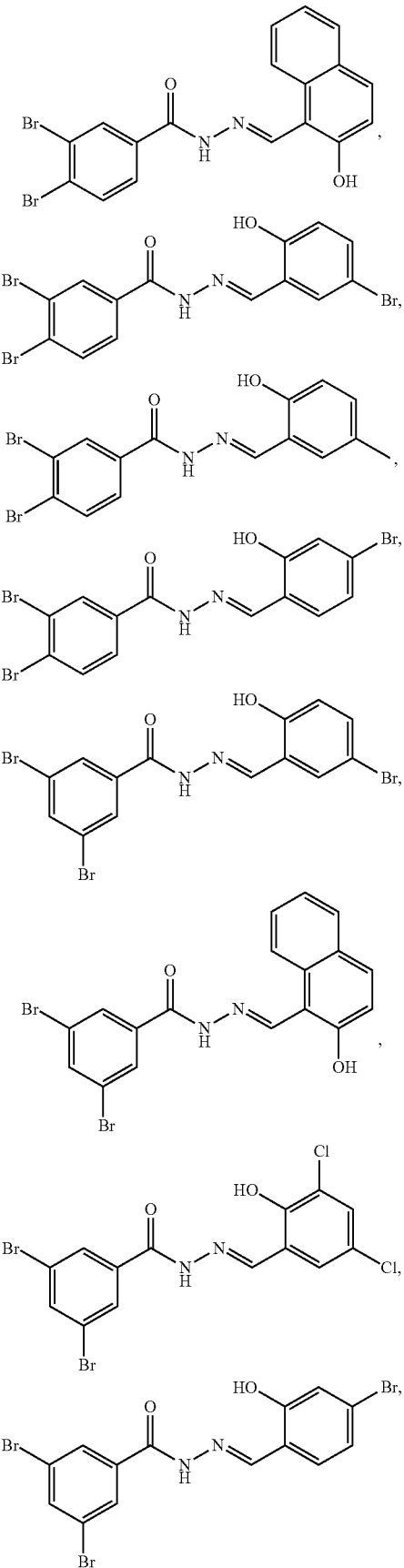

-continued
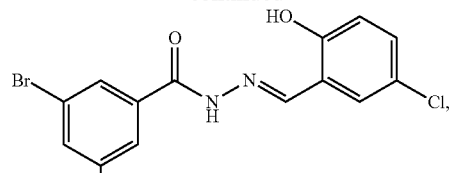
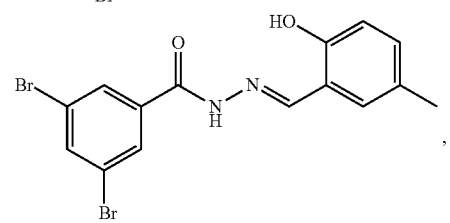
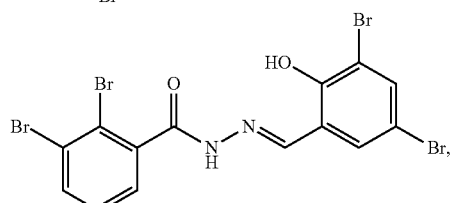
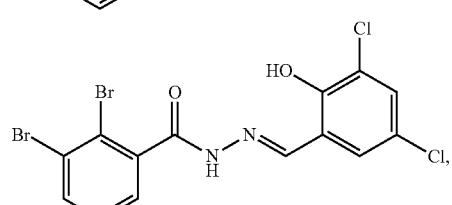
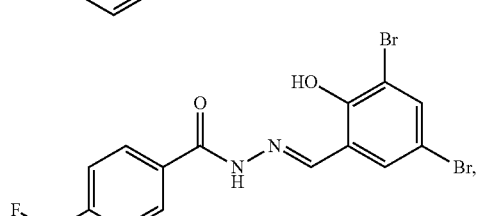
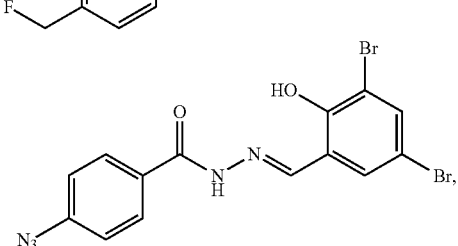
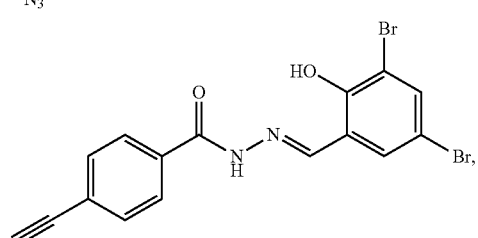
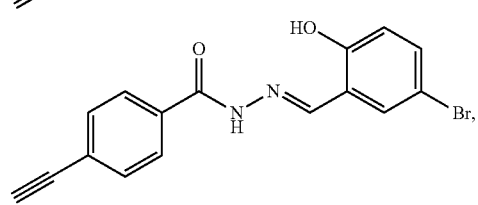
-continued
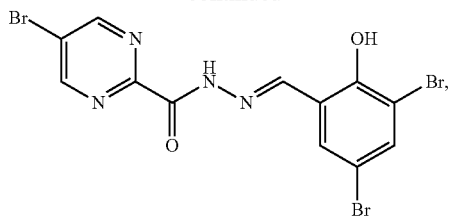
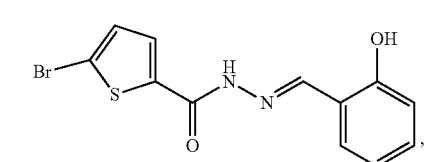
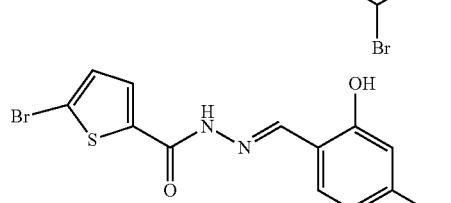
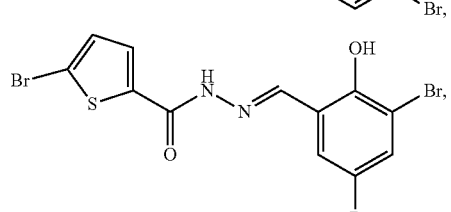
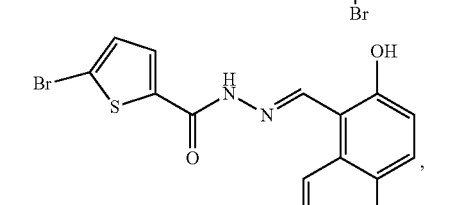
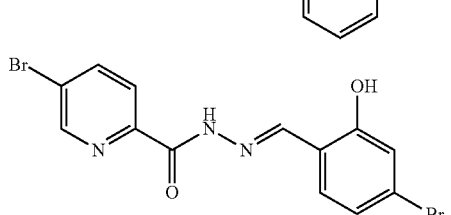
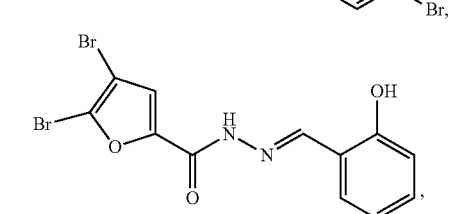
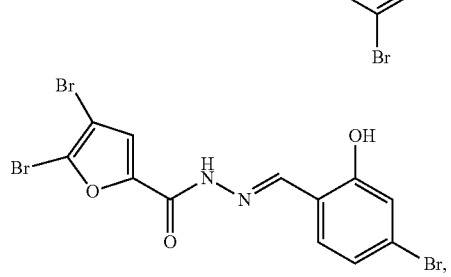

-continued

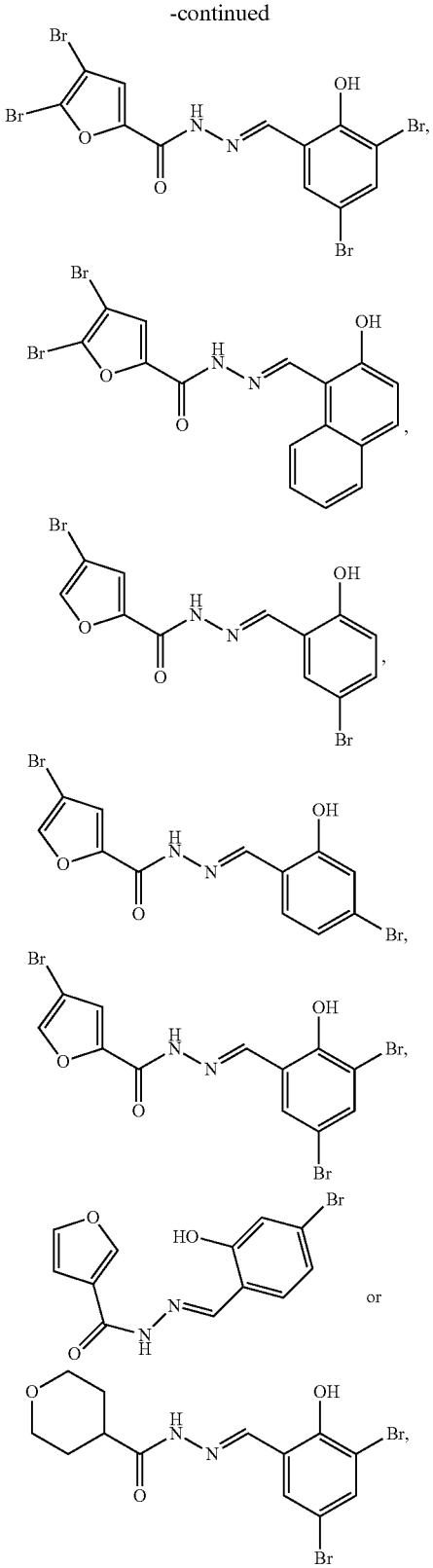

or a pharmaceutically acceptable salt thereof.

In some embodiments of the method, further comprising contacting the fungus with an effective amount of an anti-fungal agent.

In some embodiments of the method, further comprising administering to the mammal an effective amount of an anti-fungal agent.

In some embodiments of the method, wherein the amount of the compound and the amount of the anti-fungal agent when taken together is more effective to inhibit the growth of the fungus than the anti-fungal agent alone, or more effective to inhibit fungal sphingolipid synthesis than the anti-fungal agent alone.

In some embodiments of the method, wherein the amount of the compound and the amount of the anti-fungal agent when taken together is more effective to inhibit fungal sphingolipid synthesis without substantially inhibiting mammalian sphingolipid synthesis in the mammal than the anti-fungal agent alone.

In some embodiments of the method, wherein the anti-fungal agent is fluconazole, amphotericin B, caspofungin, tunicamycin or aureobasidin A.

In some embodiments of the method, wherein the fungus is *Cryptococcus Neoformans, Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum, Aspergillus* spp., dimorphic fungi or mucorales fungi.

In some embodiments of the method, wherein the fungus is other than *Cryptococcus Neoformans.*

In some embodiments of the method, wherein the fungus is *Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum, Aspergillus* spp., dimorphic fungi or mucorales fungi.

In some embodiments of the method, wherein the fungal sphingolipid is glucosylceramide (GlcCer).

The present invention yet further provides a method of inhibiting the growth of or killing a fungus in a subject or treating a subject afflicted with a fungal infection comprising administering to the subject an effective amount of the compound of the present invention, or a pharmaceutically acceptable salt or ester thereof, so as to thereby inhibiting the growth of or kill the fungus in the subject or treat the subject afflicted with the fungal infection.

In some embodiments of the method, further comprising administering an effective amount of an anti-fungal agent.

In some embodiments of the method, wherein the amount of the compound and the amount of the anti-fungal agent when taken together is more effective to treat the subject than when the anti-fungal agent is administered alone.

In some embodiments of the method, wherein the amount of the compound and the amount of the anti-fungal agent when taken together is effective to reduce a clinical symptom of the fungal infection in the subject.

In some embodiments of the method, wherein the anti-fungal agent is fluconazole, amphotericin B, caspofungin, tunicamycin or aureobasidin A.

In some embodiments of the method, wherein the fungal infection caused by *Candida, Aspergillus, Cryptococcus, Histoplasma, Pneumocystis Stachybotrys* or *Mycrorales* fungus.

In some embodiments of the method, wherein the fungal infection is caused by *Cryptococcus Neoformans.*

In some embodiments the method, wherein the fungal infection is *Cryptococcus neoformans* cryptococcosis.

In some embodiments of the method, wherein the fungal infection is caused by a fungus other than *Cryptococcus Neoformans*.

In some embodiments of the method, wherein the fungal infection is a fungal infection other than *Cryptococcus neoformans* cryptococcosis.

In some embodiments of the method, wherein the fungal infection is *Aspergillosis, Blastomycosis, Candidiasis, Coccidioidomycosis, Cryptococcus gattii* cryptococcosis, Fungal Keratitis, Dermatophytes, Histoplasmosis, Mucormycosis, Pneumocystis pneumonia* (PCP), or *Sporotrichosis*.

In some embodiments of the method, wherein the fungal infection is caused by *Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp., *Paecilomyces variotii, Pneumocystis murina, Pneumocystis jiroveci, Histoplasma capsulatum, Aspergillus* spp., or dimorphic fungi.

The present invention yet further provides a compound having the following structure:

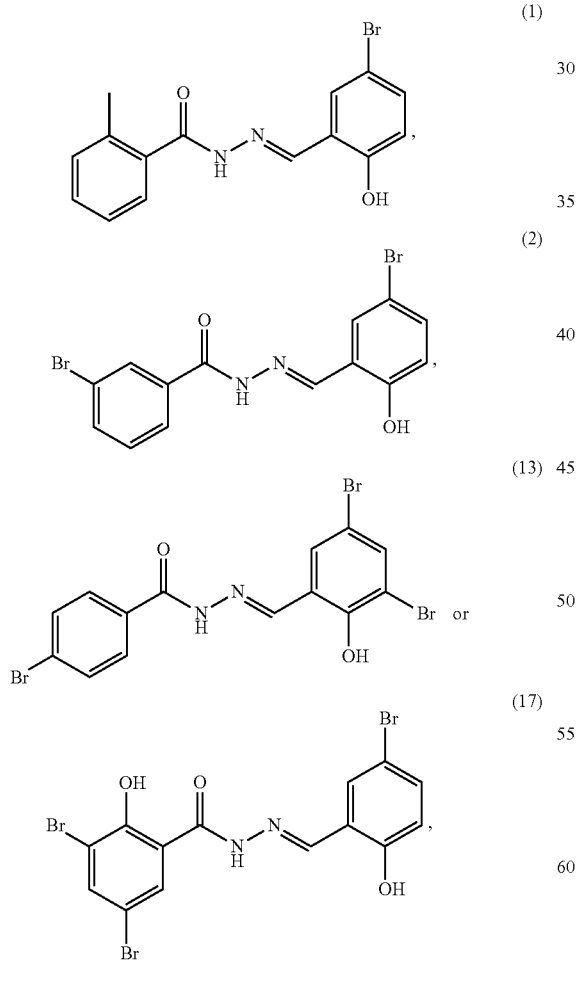

or a pharmaceutically acceptable salt thereof, for use in inhibiting the growth of a fungus.

The present invention yet further provides a compound having the following structure:

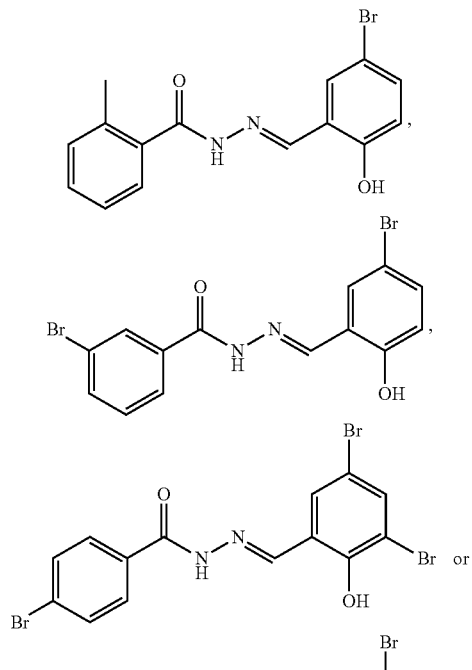

or a pharmaceutically acceptable salt thereof, for use in inhibiting fungal sphingolipid synthesis in a fungus.

The present invention yet further provides a compound having the following structure:

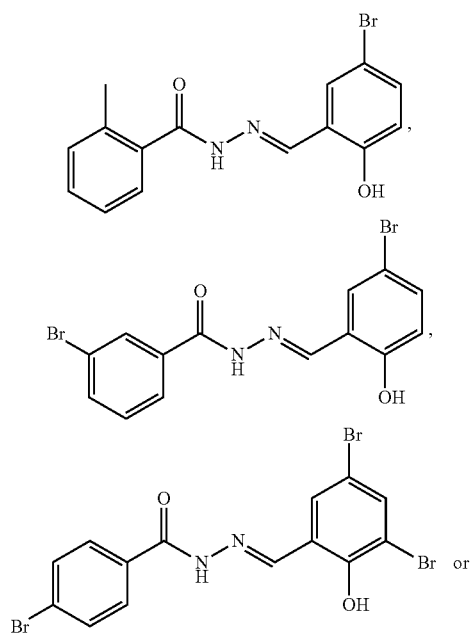

-continued

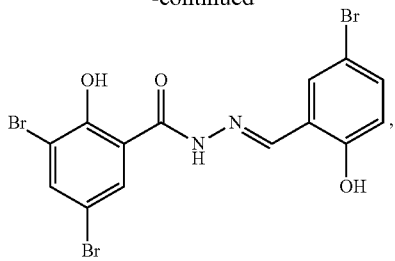

or a pharmaceutically acceptable salt thereof, for use in inhibiting fungal sphingolipid synthesis in a fungus in a mammal.

The present invention yet further provides a compound having the following structure:

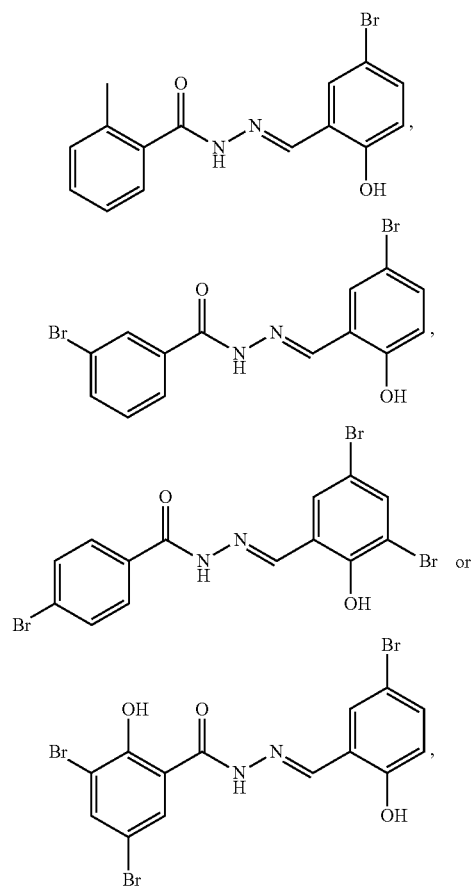

or a pharmaceutically acceptable salt thereof, for use in inhibiting the growth of or killing a fungus in a subject or treating a subject afflicted with a fungal infection caused by the fungus.

In some embodiments the compound for use wherein the fungus is other than *Cryptococcus Neoformans*.

In some embodiments the compound for use wherein the fungal infection is caused by a fungus other than *Cryptococcus Neoformans*.

In some embodiments the compound for use wherein the fungal infection is a fungal infection other than *Cryptococcus neoformans* cryptococcosis.

In some embodiments the compound for use further comprising an anti-fungal agent.

In some embodiments the compound for use wherein the anti-fungal agent is fluconazole, amphotericin B, caspofungin, tunicamycin or aureobasidin A.

The present invention yet further provides a pharmaceutical composition comprising the compound having the following structure:

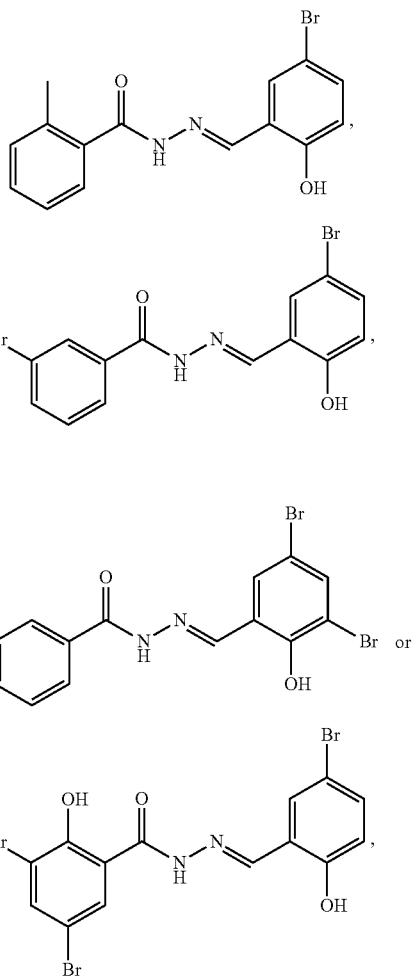

or a pharmaceutically acceptable salt thereof, an anti-fungal agent and a pharmaceutically acceptable carrier.

In some embodiments, the pharmaceutical composition wherein the anti-fungal agent is fluconazole, amphotericin B, caspofungin, tunicamycin or aureobasidin A.

The present invention yet further provides a pharmaceutical composition comprising a compound having the following structure:

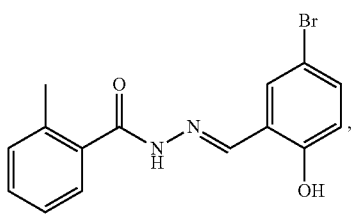

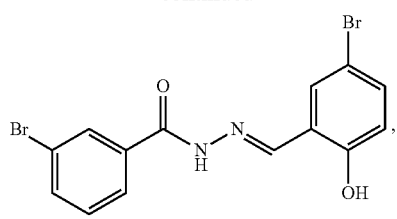

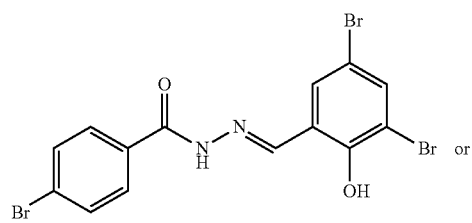

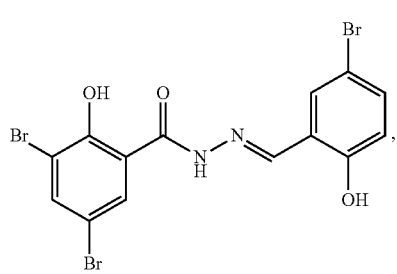

or a pharmaceutically acceptable salt thereof, for use in inhibiting the growth of a fungus.

The present invention yet further provides a pharmaceutical composition comprising a compound having the following structure:

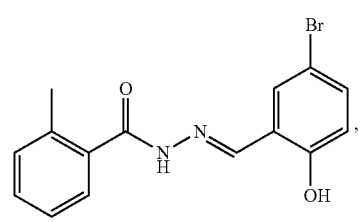

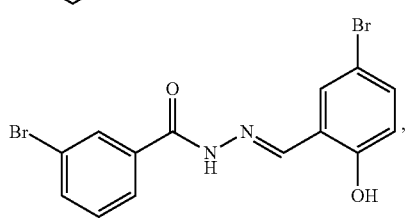

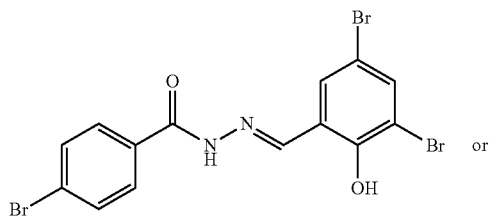

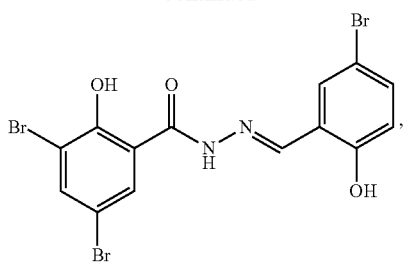

or a pharmaceutically acceptable salt thereof, for use in inhibiting fungal sphingolipid synthesis in a fungus.

The present invention yet further provides a pharmaceutical composition comprising a compound having the following structure:

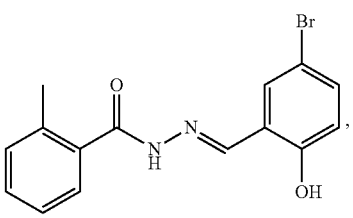

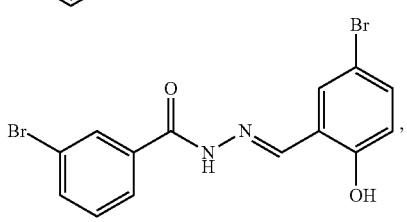

or a pharmaceutically acceptable salt thereof, for use in inhibiting fungal sphingolipid synthesis in a fungus in a mammal.

The present invention yet further provides a pharmaceutical composition comprising a compound having the following structure:

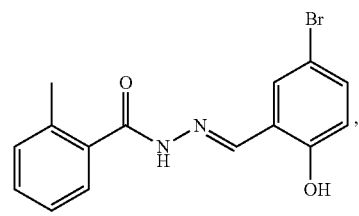

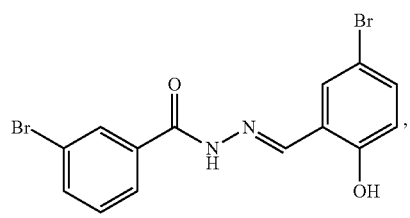

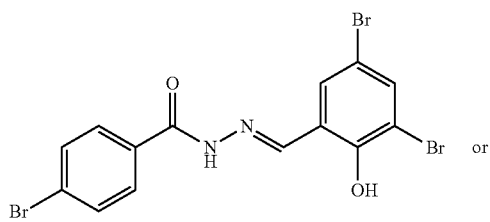

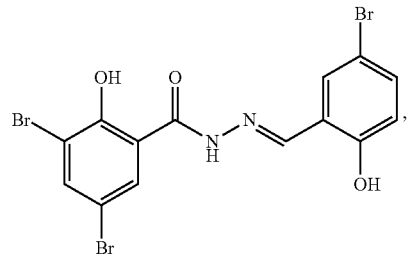

or a pharmaceutically acceptable salt thereof, for use in inhibiting the growth of or killing a fungus in a subject or treating a subject afflicted with a fungal infection caused by the fungus.

The present invention yet further provides a pharmaceutical composition comprising a compound having the following structure:

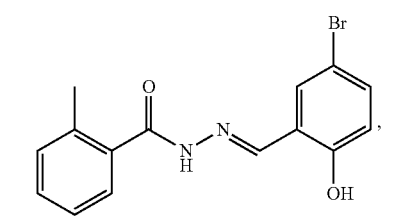

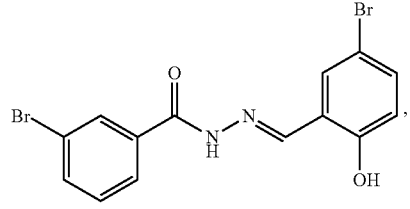

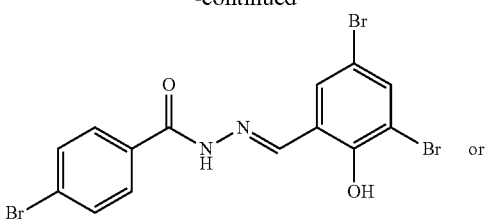

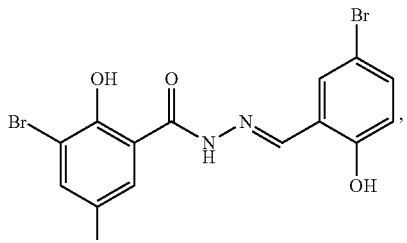

or a pharmaceutically acceptable salt thereof, and an anti-fungal agent for use in inhibiting the growth of a fungus.

The present invention yet further provides a pharmaceutical composition comprising a compound having the following structure:

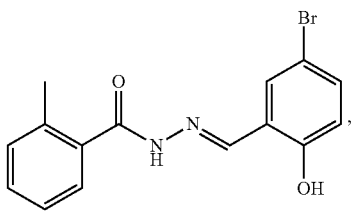

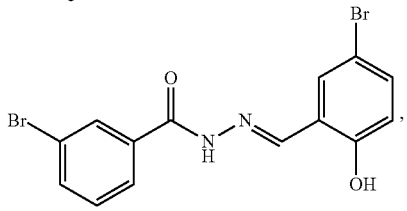

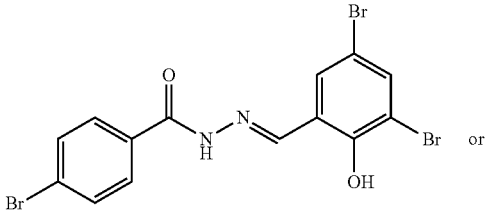

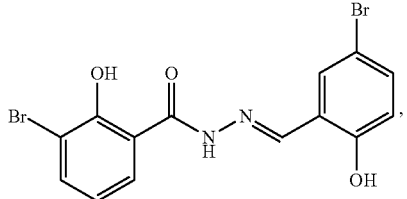

or a pharmaceutically acceptable salt thereof, and an anti-fungal agent for use in inhibiting fungal sphingolipid synthesis in a fungus.

The present invention yet further provides a pharmaceutical composition comprising a compound having the following structure:

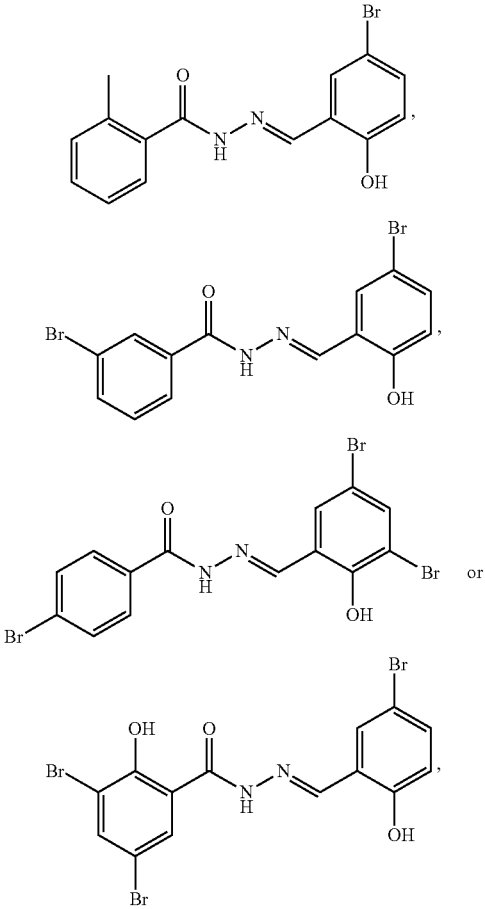

or a pharmaceutically acceptable salt thereof, and an anti-fungal agent for use in inhibiting fungal sphingolipid synthesis in a fungus in a mammal.

The present invention yet further provides a pharmaceutical composition comprising a compound having the following structure:

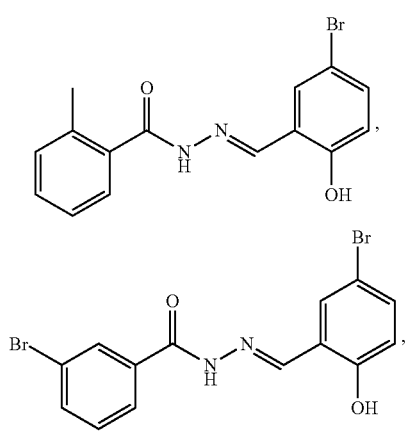

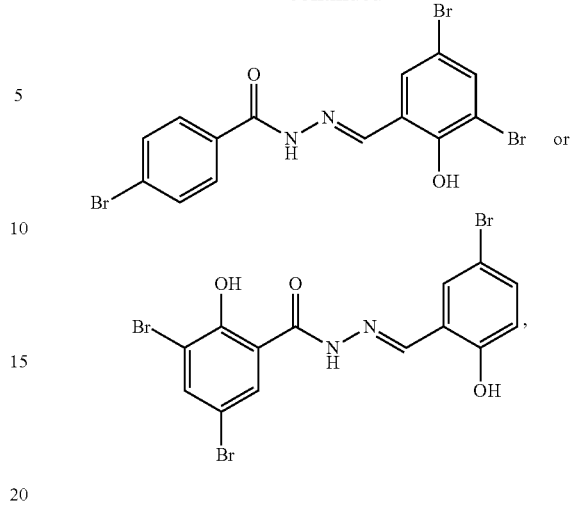

or a pharmaceutically acceptable salt thereof, and an anti-fungal agent for use in inhibiting the growth of or killing a fungus in a subject or treating a subject afflicted with a fungal infection caused by the fungus.

In some embodiments, the method wherein the anti-fungal agent is fluconazole, amphotericin B, caspofungin, tunicamycin or aureobasidin A.

In some embodiments, the method wherein the fungal infection is caused by *Candida, Aspergillus, Cryptococcus, Histoplasma, Pneumocystis, Stachybotrys* or *Mycrorales* fungus.

In some embodiments, the method wherein the fungal infection is Aspergillosis, Blastomycosis, Candidiasis, Coccidioidomycosis, *Cryptococcus gattii* cryptococcosis, Fungal Keratitis, Dermatophytes, Histoplasmosis, Mucormycosis, *Pneumocystis pneumonia* (PCP), or Sporotrichosis.

In some embodiments, the method wherein the fungal infection is caused by *Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces dermatitis, Histoplasma capsulatum, Coccidioides* spp. *Paecilomyces variotii, Pneumocystis murina, Pneumocystis jiroveci, Histoplasma capsulatum*, or dimorphic fungi.

In some embodiments, the fungal infection is an internal fungal infection.

In some embodiments, the fungal infection is an invasive fungal infection.

In some embodiments, the fungal infection is a fungal infection of the skin or lung. In some embodiments, the compound has a fungistatic effect on the fungus. In some embodiments, the compound has a fungicidal effect on the fungus. In some embodiments, the compound is administered orally to the subject. In some embodiments, the compound is administered topically to the subject. In some embodiments, the subject is also afflicted with an immunodeficiency disorder. In some embodiments, the subject is also afflicted with human immunodeficiency virus (HIV).

In some embodiments, the antifungal agent is Amphotericin B, Candicidin, Filipin, Hamycin, Natamycin, Nystatin, Rimocidin, Clotrimazole, Bifonazole, Butoconazole, Clotrimazole, Econazole, Fenticonazole, Isoconazole, Ketoconazole, Luliconazole, Miconazole, Omoconazole, Oxiconazole, Sertaconazole, Sulconazole, Tioconazole, Albaconazole, Fluconazole, Isavuconazole, itraconazole, Posaconazole, Ravuconazole, Terconazole, Voriconazole, Abafungin, Amorolfin, Butenafine, Naftifine, Terbinafine, Anidulafungin, Caspofungin, Micafungin, Ciclopirox, Flucytosine, Griseofulvin, Haloprogin, Tolnaftate, or Undecylenic acid.

In some embodiments, a pharmaceutical composition comprising a compound of the present invention and an antifungal agent, and at least one pharmaceutically acceptable carrier for use in treating a fungal infection.

In some embodiments, a pharmaceutical composition comprising an amount of the compound of the present invention for use in treating a subject afflicted with a fungal infection as an add-on therapy or in combination with, or simultaneously, contemporaneously or concomitantly with an anti-fungal agent.

In some embodiments of any of the above methods or uses, the subject is a human. In some embodiments of any of the above methods or uses, the compound and/or antifungal agent is orally administered to the subject. In some embodiments of any of the above methods or uses, the compound and/or anti-fungal agent is topically administered to the subject.

In some embodiments, the fungus or fungal infection has developed resistance to one or more drugs. For example, a drug resistant fungal infection may have developed drug-resistance to an azole antifungal drug, a polyene antifungal drug and/or an echinocandin antifungal drug.

In some embodiments of any of the above methods or uses, the compound ti targets APL5, COS111, MKK1, and STE2 in the fungus. In some embodiments of any of the above methods or uses, the compound targets at least one of APL5, COS111, MKK1, or STE2 in the fungus. In some embodiments of any of the above methods or uses, the compound disrupts vesicular transport mediate by APL5. In some embodiments of any of the above methods or uses, the fungus carries non-mutated APL5, COS111, MKK2, and STE2. In some embodiments of any of the above methods or uses, the fungus carries at least one of non-mutated APL5, COS111, MKK1, and STE2.

As used herein, a "symptom" associated with a fungal infection includes any clinical or laboratory manifestation associated with the fungal infection and is not limited to what the subject can feel or observe.

As used herein, "treating", e.g. of a fungal infection, encompasses inducing prevention, inhibition, regression, or stasis of the disease or a symptom or condition associated with the infection.

Compound 1 (ID #5271226), Compound 2 (ID #5281029), Compound 13 (ID #5475098), and Compound 17 (ID #5275737), are available from ChemBridge™, San Diego, CA.

The contents of International Application Publication No. WO/2016/094307, published Jun. 16, 2016, are hereby incorporated by reference.

The compounds of the present invention include all hydrates, solvates, and complexes of the compounds used by this invention. If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. The compounds described in the present invention are in racemic form or as individual enantiomers. The enantiomers can be separated using known techniques, such as those described in Pure and Applied Chemistry 69, 1469-1474, (1997) IUPAC. In cases in which compounds have unsaturated carbon-carbon double bonds, both the cis (Z) and trans (H) isomers are within the scope of this invention.

The compounds of the subject invention may have spontaneous tautomeric forms. In cases wherein compounds may exist in tautomeric forms, such as keto-enol tautomers, each tautomeric form is contemplated as being included within this invention whether existing in equilibrium or predominantly in one form.

In the compound structures depicted herein, hydrogen atoms are not shown for carbon atoms having less than four bonds to non-hydrogen atoms. However, it is understood that enough hydrogen atoms exist on said carbon atoms to satisfy the octet rule.

This invention also provides isotopic variants of the compounds disclosed herein, including wherein the isotopic atom is $^2H$ and/or wherein the isotopic atom $^{13}C$. Accordingly, in the compounds provided herein hydrogen can be enriched in the deuterium isotope. It is to be understood that the invention encompasses all such isotopic forms.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

Except where otherwise specified, if the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}C$, $^{13}C$, or $^{14}C$. Furthermore, arty compounds containing $^{13}C$ or $^{14}C$ may specifically have the structure of any of the compounds disclosed herein.

It will also be noted that any notation of a hydrogen in structures throughout this application, when used without further notation, are intended to represent all isotopes of hydrogen, such as $^1H$, $^2H$, or $^3H$. Furthermore, any compounds containing $^2H$ or $^3H$ may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano, carbamoyl and aminocarbonyl and aminothiocarbonyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" is intended to include both branched and straight-chain saturated aliphatic hydrocarbon groups having the specified number of carbon atoms. Thus, $C_1$-$C_n$ as in "$C_1$-$C_n$ alkyl" is defined to include groups having 1, 2 . . . , n–1 or n carbons in a linear or branched arrangement, and specifically includes methyl, ethyl, propyl, butyl, pentyl, hexyl, heptyl, isopropyl, isobutyl, sec-butyl and so on. An embodiment can be $C_1$-$C_{12}$ alkyl, $C_2$-$C_{12}$ alkyl, $C_3$-$C_{12}$ alkyl, $C_4$-$C_{12}$ alkyl and so on. "Alkoxy" represents an alkyl group as described above attached through an oxygen bridge.

The term "alkenyl" refers to a non-aromatic hydrocarbon radical, straight or branched, containing at least 1 carbon to carbon double bond, and up to the maximum possible number of non-aromatic carbon-carbon double bonds may be present. Thus, $C_2$-$C_n$ alkenyl is defined to include groups having 1, 2 . . . , n–1 or n carbons. For example, "$C_2$-$C_6$ alkenyl" means an alkenyl radical having 2, 3, 4, 5, or 6 carbon atoms, and at least 1 carbon-carbon double bond, and up to, for example, 3 carbon-carbon double bonds in the case of a $C_6$ alkenyl, respectively. Alkenyl groups include ethenyl, propenyl, butenyl and cyclohexenyl. As described above, with respect to alkyl, the straight, branched or cyclic portion of the alkenyl group may contain double bonds and may be substituted if a substituted alkenyl group is indicated. An embodiment can be $C_2$-$C_{12}$, alkenyl, $C_3$-$C_{12}$ alkenyl, $C_4$-$C_{12}$ alkenyl and so on.

The term "alkynyl" refers to a hydrocarbon radical straight or branched, containing at least 1 carbon to carbon triple bond, and up to the maximum possible number of non-aromatic carbon-carbon triple bonds may be present. Thus, $C_2$-$C_n$ alkynyl is defined to include groups having 1, 2 . . . , n–1 or n carbons. For example, "$C_2$-$C_6$ alkynyl" means an alkynyl radical having 2 or 3 carbon atoms, and 1 carbon-carbon triple bond, or having 4 or 5 carbon atoms, and up to 2 carbon-carbon triple bonds, or having 6 carbon atoms, and up to 3 carbon-carbon triple bonds. Alkynyl groups include ethynyl, propynyl and butynyl. As described above with respect to alkyl, the straight or branched portion of the alkynyl group may contain triple bonds and may be substituted if a substituted alkynyl group is indicated. An embodiment can be a $C_2$-$C_n$ alkynyl. An embodiment can be $C_2$-$C_{12}$ alkynyl, $C_3$-$C_{12}$ alkynyl, $C_4$-$C_{12}$ alkynyl and so on "Alkylene", "alkenylene" and, "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "heteroalkyl" includes both branched and straight-chain saturated aliphatic hydrocarbon groups having the specified number of carbon atoms and at least 1 heteroatom within the chain or branch.

As used herein, "heterocycle" or "heterocyclyl" as used herein is intended to mean a 5- to 10-membered nonaromatic ring containing from 1 to 4 heteroatoms selected from the group consisting of O, N and S, and includes bicyclic groups. "Heterocyclyl" therefore includes, but is not limited to the following: imidazolyl, piperazinyl, piperidinyl, pyrrolidinyl, morpholinyl, thiomorpholinyl, tetrahydropyranyl, dihydropiperidinyl, tetrahydrothiophenyl and the like. If the heterocycle contains a nitrogen, it is understood that the corresponding N-oxides thereof are also encompassed by this definition.

As herein, "cycloalkyl" shall mean cyclic rings of alkanes of three to eight total carbon atoms, or any number within this range (i.e., cyclopropyl, cyclobutyl, cyclopentyl, cyclohexyl, cycloheptyl or cyclooctyl).

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a)

fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by his definition.

The term "alkylheteroaryl" refers to alkyl groups as described above wherein one or more bonds to hydrogen contained therein are replaced by a bond to an heteroaryl group as described above. It is understood that an "alkylheteroaryl" group is connected to a core molecule through a bond from the alkyl group and that the heteroaryl group acts as substituent on the alkyl group. Examples of alkylheteroaryl moieties include, but are not limited to, —CH$_2$—(C$_5$H$_4$N), —CH$_2$—CH$_2$—(C$_5$H$_4$N) and the like.

The term "heterocycle" or "heterocyclyl" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring (s), heteroaryl ring(s), aryl ring (s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise. In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

The terms "substitution", "substituted" and "substituent" refer to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropryl, n-butyl, tert-butyl, and trifluoromethyl; hydroxyl; alkoxy groups, such as methoxy, ethoxy, n-propoxy, and isopropoxy; aryloxy groups, such as phenoxy; arylalkyloxy, such as benzyloxy (phenylmethoxy) and p-trifluoromethylbenzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethyl amino, and diethylamidino; and carboxyl. Where multiple substituent moieties are disclosed or claimed, the substituted compound can be independently substituted by one or more of the disclosed or claimed substituent moieties, singly or pluraly. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well known in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) 5$^{th}$ Edition (1996), March's Advanced. Organic Chemistry: Reactions, Mechanisms, and Structure, Michael B. Smith, Jerry March, (Wiley-Interscience) 5$^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

In some embodiments, a pharmaceutical composition comprising the compound of the present invention and a pharmaceutically acceptable carrier.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject. Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human. Services, 30$^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", J. Pharm. Sci. 66:1-19).

The compounds of the present invention may also form salts with basic amino acids such a lysine, arginine, etc. and with basic sugars such as N-methylglucamine, 2-amino-2-deoxyglucose, etc. and any other physiologically non-toxic basic substance.

As used herein, "administering" an agent may be performed using any of the various methods or delivery systems well known to those skilled in the art. The administering can be performed, for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, intrathecally, into a cerebral ventricle, intraventricularly, intratumorally, into cerebral parenchyma or intraparenchchymally.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier as are slow-release vehicles.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antitumor agents. The compounds can be administered in oral dosage forms as tablets, capsules, pills, powders, grannies, elixirs, tinctures, suspensions, syrups, and emulsions. The compounds may also be administered in intravenous (bolus or infusion), intraperitoneal, subcutaneous, or intramuscular form, or introduced directly, e.g. by in topical application, or other methods, into or topically onto a site of disease or lesion, all using dosage forms well known to those of ordinary skill in the pharmaceutical arts.

The compounds used in the method of the present invention can be administered in admixture with suitable pharmaceutical diluents, extenders, excipients, or in carriers such as the novel programmable sustained-release multi-compartmental nanospheres (collectively referred to herein as a pharmaceutically acceptable carrier) suitably selected with respect to the intended form of administration and as consistent with conventional pharmaceutical practices. The unit will be in a form suitable for oral, nasal, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form, of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and hulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979) Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1909); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable hinders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present; invention may also be administered in the form of liposome delivery systems, such as small unilamellar vesicles, large unilamellar vesicles, and multilamellar vesicles. Liposomes can be formed from a variety of phospholipids such as lecithin, sphingomyelin, proteolipids, protein-encapsulated vesicles or from cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropylmethacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar-coated or film-coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, asuitable oil, saline, aqueous dextrose (glucose), and related sugar solutions and glycols such as propylene glycol or polyethylene glycols are suitable carriers for parenteral solutions. Solutions for parenteral administration preferably contain a water-soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobactene. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials such as solutol and/or ethanol to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, ail using dosage forms well known to those of ordinary skill in the pharmaceutical arts.

Specific examples of pharmaceutically acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described-in the following references: 7 Modern Pharmaceutics, Chapters 9 and 10 (Banker & Rhodes, Editors, 1979); Pharmaceutical Dosage Forms: Tablets (Lieberman et al., 1931); Ansel, introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989) Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric-coated to prevent release of the active ingredient compounds before they reach the small intestine. Materials that may be used as enteric coatings include, but are not limited to, sugars, fatty acids, proteinaceous substances such as gelatin, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

Variations on those general synthetic methods will be readily apparent to those of ordinary skill in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

Experimental Details

The following materials and methods are used to test the compounds of the present invention.

Strains, Media and Reagents

A series of fungal clinical isolates and reference strains were used in this study. This includes *Cryptococcus neoformans, Cryptococcus gattii, Candida albicans, Candida krusei, Candida glabrata, Candida parapsilosis, Candida guilliermondii, Aspergillus fumigatus, Rhizopus oryzae, Blastomyces dermatitis, Histoplasma capsulatum, Coccidioides* spp. *Paecilomyces variotii, Pneumocystis murina*, and, *Pneumocystis jiroveci. Escherichia coli* DH5-α and *Pseudomonas aeruginosa* were also used. Yeast Peptone Dextrose (YPD), Yeast Nitrogen Base (YNB), Luria Bertani (LB), Roswell Park Memorial Institute (RPMI) or Dulbecco Modified Eagle Medium (DMEM) were purchased from invitrogen Life Technologies and used as described. Fluconazole, Amphotericin B, Dexamethasone, Cyclophosphamide, Tunicamycin were purchased from Sigma-Aldrich, St Louis, MO. Caspofungin. and Posaconazole were obtained from Merck, Rahway, NJ, Voriconazole was obtained from Pfizer, Rey Brook, NY.

In Viva Labeling with Tritiated Palmitate ($^3$H palmitate)

Labeling fungal cells. *C. neoformans* cells were grown in YNB (pH 7.4) at in presence of 5% $CO_2$ for 16 hrs. Cells were centrifuged for 10 min. at 3,000 rpm at room temperature. Supernatant was removed and the cell pellet was suspended and counted. Next, 900 μL, containing 5×10$^8$ *C. neoformans* cells were placed into a 15 ml round bottom Corning centrifuge tube. Then, 100 μL of different concentrations of compound diluted in YNB containing 0.1% DMSO was added resulting in final concentrations of 0.25, 1 and 4 μg/ml, or 0.075, 0.3, 1.2 μg/ml, respectively. Tubes were incubated at in shaker incubator at 225 rpm at 37° C. in the presence of 5% $CO_2$ for 4 hours. Then, 30 μCi/ml of $^3$H palmitate (PerkinElmer Waltham, MA) was added to the culture and incubated for additional 2 hours. Cells without the drug were included as negative control. The cells were then pelleted and washed once with distilled sterile water and suspended in 1.5 ml of Mandala lipid extraction buffer. The lipids were extracted by the methods of Mandala, (Mandala, S. M, et al. 1997) and Bligh and Dyer followed by methanolic based-hydrolysis as previously described (Bligh, E. G. & Dyer, W. J. 1959). The tube was flushed with nitrogen gas and the samples dried in a SPD210 SpeedVac system (Thermofisher Scientific, Waltham, MA. The dried lipids were resuspended in 30 μL of 1:1 methanol:chloroform and loaded on thin layered chromatography (TLC) silica gel 60 (EDM Millipore, Billerica, MA), Glucosylceramide (GlcCer) standard from soybean (Avanti Polar Lipids, Alabaster, AL) was added in a separate lane as control. The sample was resolved in a tank containing a chloroform:

methanol:water (65:25:4) as the mobile phase. The TLC plates were then dried, exposed to iodine fume for the identification of the GlcCer standard band, which was marked. The TLC plate was then enhanced by spraying with ENHENCER (PerkinElmer) exposed to X-Ray film at −80° C. for 72 hours and the film was developed.

Labeling mammalian cells. The murine macrophage cell line J774.16 was maintained in Dulbecco Minimum. Eagle Medium (DMEM) containing 10% Fetal. Bovine Serum (PBS) and 1% Pen-strep by regular seeding. Cell at a density of $5 \times 10^6$ cells/mi of passage 8 were cultured in a 6 well culture plate for 14 hours to achieve adherence. Compound at the same concentrations used for fungal cells (see above) were added to the plate for 4 hours. Then, 30 μCi/mL of $^3$H palmitic acid was added and the plate was further incubated for 2 hrs. Labeled J774.16 but untreated cells were included as control. The cells were harvested by the addition of 0.05% trypsin-EDTA and scraping with cell scrapper and washed once with PBS and dissolved in 2 ml methanol and 1 ml chloroform. Lipids were extracted by the method of Bligh and Dyer followed by base hydrolysis. The samples were flushed with nitrogen and dried in SpeedVac. Dried lipids were suspended in 30 μL of 1:1 methanol:chloroform and loaded on a TLC plate with GlcCer as standard.

In Vitro Susceptibility Testing

Minimal inhibitory concentration (MIC) was determined following the methods of the Clinical Laboratory Standards Institutes (CLSI) with modifications. MIC studies used either RPMI or YNB medium (pH 7.0, 0.2% glucose) buffered with HEPES. HEPES was used instead of MOPS because MOPS totally inhibits the activity of the compound. The compound was serially diluted from 32 to 0.03 μg/ml or 19 to 0.02 μg/ml respectively in a 96 well plate with the respective medium. The yeast inoculum was prepared as described in the CLSI protocol M27-A3 guidelines. Plates were incubated at 37° C. and in the presence of 5% $CO_2$ for 24-96 hours. Against all fungal isolates used in the initial susceptibility screen, the MICs were determined as the lowest concentration of the drug that inhibited 50% of growth compared to the control. MIC80 and MIC100, whose drug concentrations inhibited 30% and 100% growth compared to the control respectively, were also determined. For antibacterial activity, E. coli DH5α and P. aeruginosa PA14 were grown overnight in Luria Bertani (LB) broth at 30° C. The cells were washed with PBS and counted. Then, 300 μL from $2 \times 10^8$ cells/mL was spreaded onto LB agar plate using a hockey stick glass spreader. The plate was dried, and wells were punched out using a cut tip. Fifty microliters of different drug concentration was added to the well. The plate was then incubated at 30° C. for 24 hours.

In Vitro Testing against P. murina and P. jiroveci

Cryopreserved and characterized P. carinii isolated from rat lung tissue (Pc 08-4 #45) was distributed into triplicate wells of 48-well plates with a final volume of 500 μL and a final concentration of $5 \times 10^7$ nuclei/ml. Control dilutions were added and incubated at 37° C. At 24, 48, and 72 hours, 10% of the well volume was removed and the ATP content was measured using Perkin Elmer ATP-liteM luciferin-luciferase assay. The luminescence generated by the ATP content of the samples was measured by a spectrophotometer (PolarStar Optima BMG, Ortenberg, Germany). A sample of each group was examined microscopically on the final assay day of the assay to rule out the presence of bacteria contamination.

In Vitro Killing Assay

From an overnight culture, C. neoformans cells were washed in PBS, resuspended in YNB buffered with HEPES at pH 7.4. Cells were counted and $2 \times 10^4$ cells were incubated with either 1, 2 or 4 μg/ml of compound in a final volume of 10 ml. Tubes were then incubated at 37° C. in the presence of 5% $CO_2$ on a rotary shaker at 200 rpm. At the illustrated time points, aliquots were taken and diluted and 100 μL was plated onto yeast peptone dextrose (YPD) plates. YPD plates were incubated in a 30° C. incubator and, after 72 hours, colony forming units (CFU) were counted and recorded.

Intracellular Effect

To assess whether the compound will be effective against intracellular C. neoformans, we first incubated J774.16 macrophages with C. neoformans cells at a 1:20 ratio in presence of opsonins (complement and antibody mAb 18B7 against the cryptococcal capsular antigen). After 2 hours of incubation, about 60-80% of macrophages have at least one C. neoformans cell internalized. At this time, wells were washed to remove extracellular fungal cells and fresh DMEM medium without serum and without mAb 18B7 but containing different concentrations of compound was added. Plates were incubated at 37° C. and 5% $CO_2$. At selected time points, 0, 6, 12 and 24 hours, extracellular cells were collected by washing and plated onto YPD for CFU counting of extracellular cells. Then, macrophages containing C. neoformans e lysed, collected and serial dilutions were plated onto YPD for CPU counting of intracellular fungal cells.

Synergistic Assay

Synergistic activity was assayed by calculating the fractional inhibitory index (FIC) as previously described (Del Poeta, M. et al. 2000). Briefly, in a 96 well plate, the compound was serially diluted from 16 to 0.015 μg/ml (11 dilutions) whereas drug B (e.g., either Fluconazole, Amphotericin B, Caspofungin, or Tunicamycin) was serially diluted from 12 to 0.19 μg/ml, 5 to 0.078 μg/ml, 70 to 1.09 μg/ml, and 6 to 0.09 μg/ml (7 dilutions), respectively. The FIC was defined as: [MIC combined/MIC Drug A alone]+[MIC combined/MIC Drug B alone].

Resistance Assay

To see whether incubation with the drugs will induce resistance, C. neoformans cells were passaged daily in sub-MIC drug concentrations. Briefly, from an overnight culture, C. neoformans cells were washed with PBS, resuspended in YNB buttered with HEPES at pH 7.4 and counted. Then, $10^6$ cells were incubated with 0.5, 0.25 or 0.125 μg/ml of compound or 0.15, 0.075 and 0.037 μg/ml of compound in 1 ml final volume. Tubes without the drug served as negative control. Tubes with Fluconazole (0.5, 1 and 2 μg/ml) served as positive control. The cells were grown at 37° C. in the presence on 5% $CO_2$ on a rotary shaker at 200 rpm. Every 24 hours, the cells were pelleted by centrifugation, washed with PBS, and resuspended in YNB, and $10^6$ cells were transferred into a fresh drug tube and incubated as above. These daily passages were continued for 15 days. Cell aliquots were collected on day 0 (before any drug exposure), 5, 10, 15, and MIC was determined using the microbroth dilution assay as described above.

Animal Studies for Cryptococcosis

For survival studies, 4-week old CBA/J female mice (Jackson Laboratory, Bar Harbor, ME) were used. Ten mice per treatment or control group were used. Mice were infected by nasal inoculation of 20 μL containing $5 \times 10^5$ cells of C. neoformans H99 strain. Treated mice received an intraperitoneal injection of 1.2 mg/kg/day of compound in 100 μL final volume of PBS containing 0.4% DMSO. Untreated mice, received 100 μL of PBS/0.4% DMSO. Mice were feed ad-libitum and monitored closely for sign of discomfort and meningitis. Nice showing abnormal gait, lethargic, tremor, significant loss of body weight or inability to reach water r food were sacrificed and survival counted from that day. At the end of the survival study, tissue burden culture was performed iii mice that survived the infection. Mice were sacrificed, and their organs were extracted, and homogenized in 10 ml sterile PBS using a homogenizer (Stomacher80, Cole-Farmer, Vernon Hills, IL). Organ homogenates were serially diluted 1:10 in PBS and 100 µL was plated on YPD agar plates and incubated at 30° C. for 72 hours for CFU count. For histopathology, extracted organs were fixed in 10% formalin before paraffin sectioning and staining with either Hematoxylin-Eosin or Mucicarmine. Images were taken 40× in a Zeiss Axle Observer in brightfield mode.

Animal Studies for Pneumocystosis

For survival studies, C3H/HeN mice ordered from the National Cancer Institute (Bethesda, MD) were used. Mice were infected with *P. murina* pneumonia through exposure to mice with a fulminant *P. murina* infection (seed mice). These mice were immune suppressed by the addition of dexamethasone at 4 mg/liter to the drinking water. Sulfuric acid at 1 ml/liter was also added to the drinking water for disinfection. The seed mice are rotated within the cages for 2 weeks and then removed. After the mice had developed a moderate infection level (approximately 5 weeks), they were divided into a negative control group (control steroid), positive control group (trimethoprim/sulfamethoxazole) and treatment groups (compound). Twelve mice were used in each group. Compound was administered intraperitoneally or by oral gavage on a mg/kg/day basis for up to 3 weeks. The dose, route, and frequency of administration varied depending on the agent being tested. At the end of the treatment, mice were sacrificed and processed for analysis. Slides were made from the lung homogenates at different dilutions and stained with Diff-Quik to quantify the trophic forms and Cresyl Echt violet to quantify the asci. Additional group of mice were selectively depleted of their CD4+ lymphocytes by antibody treatment with 300 µg of GK 1.5 antibody (Biovest International, Minneapolis, MN) administered intraperitoneally 3 times on days 1, 3, and 7. After this initial treatment, the mice were infected by exposure *P. murina* infected mice. Mice then were treated with 100 µg of GK 1.5 antibody intraperitoneally once a week for 6 weeks. Mice were then treated with 1.25 or 12.5 mg/kg/day 1 for 14 days while continuing the GK1.5 treatment. Control mice received vehicle.

Animal Studies for Candidiasis

For survival studies, 8-week old CBA/J female mice (Jackson Laboratory) were used. Eight mice per treatment or control group were used. Mice were infected by intravenous inoculation of 100 µL containing $1 \times 10^5$ cells of *Candida albicans* SC-5314 strain. Treated mice received an intraperitoneal injection of 1.2 mg/kg/day of compound in 100 µL final volume of PBS containing 0.4% DMSO. Untreated mice, received. 100 µL of PBS/0.4% DMSO. Mice were feed ad-libitum and monitored closely for sign of discomfort. At the end of the survival study, tissue burden culture was performed in mice that survived the infection. Mice were sacrificed and their organs were extracted and homogenized in 10 ml sterile PBS using homogenizer. Organ homogenates were diluted 10 times in PBS, and 100 µL was plated on YPD agar and incubated at 30° C. for 72 hours for CPU count.

Toxicity

In vitro. The murine macrophage cell line J774.16 was maintained in DMEM containing 10% FBS and 1% Pen-strep. At passage #7, $10^5$ cells/well in DMEM containing 10% FBS was transferred into 96 well plates and cultured for 14 hours for the cells to adhere to the wells. The compound was added to the cells at concentration ranging from 0.1 to 100 µg/ml. The wells without the drug served as control. The plate was incubated at 37° C. the presence of 5% $CO_2$. After 12 or 24 hours, the supernatant was removed and 50 µL of 5 mg/ml of 3-(4,5-dimethylthiazol-2-yl)-2,5-diphenyltetrazolium bromide (MTT) solution in PBS was added to each well and plates incubated for 4 additional 4 hours. The formazan crystal formed inside the cell was dissolved by adding 50 µL of isopropanol containing 0.1N HCL. The optical density was measured at 570 nm.

To determine whether the compound's toxicity was enhanced by corticosteroids, a separate set of J774.16 cells were incubated with 10 or 100 µg/ml of Dexamethasone alone or combined with either 1, 5 and 10 µg/ml of compound. After 24 hours, the MIT assay was performed as described above.

In vivo. Mice toxicity studies were performed using 4-week old CBA/J female mice from. Jackson Laboratory. Five mice received 1.2 mg/kg/day of compound for 60 days. Three control mice received a solvent injection per day. At 60-day, blood was collect in two tubes: one with $K_2$EDTA and the other without $K_2$EDTA to allow blood clotting. The blood clot was then centrifuged at 1500 rpm for 10 min, serum was collected and analyzed for liver and kidney blood tests. The non-coagulated blood was used for hematocrit and blood cells analysis. These tests were done using MASCOT™ HEMAVET 950FS (Drew Scientific Group, Dusseldorf, Germany).

Lipid Mass Spectrometry

For lipid analysis by mass spectrometry, fungal cells (*C. neoformans* or *C. albicans*) were grown in YNB, and incubated with compound as explained for the in vivo labeling (except that tritiated palmitate was not added), for 6 hrs. Samples without drug were included as control. Before lipid extraction, lipid internal standards (C17 ceramide and C17 sphingosine) were added. Lipids were then extracted following the methods of Mandala and Bligh and Dyer and one fourth the sample was aliquoted for determination of the inorganic phosphate. The remainder of the sample was subjected to base hydrolysis and then analyzed using LC/MS. Results were normalized with the inorganic phosphate levels.

In Vitro Activity of Gcs1

For the in vitro Gcs1 assay, *C. neoformans* wild-type (WT) or the Δgcs1 cells were grown in YPD broth overnight at 30° C. in a shaker incubator. Cells were washed with sterile water and then lysed by bead beating in presence of glass bead and protease cocktail inhibitor, as described (Liberto, C. et al. 2001). Next, 800 µg of cell lysate was incubated with 0.3 mM C16 ceramide (C16-R—OH) and in the presence or absence of compound. The mixture was subjected to 3 cycles of sonication (20 sec) and vortexing (5 sec). Next, 8 µM of radiolabelled UDP-$^{14}$C-Glucose (American Radiolabeled Chemical) was added and, after brief vortexing, the tubes were incubated at 37° C. for 45 min. The reaction was stopped by adding 0.9 ml of 0.45% NaCl solution containing chloroform:methanol 2:1. The organic phase was collected in a glass tube and flushed with nitrogen. The sample was dried and resuspended in chloroform:methanol 1:1. Sample was then loaded on a TLC plate using by chloroform:methanol:water as the mobile phase.

Yeast Library Screening

Variomics Library: The screening of the *Saccharomyces cerevisiae* genome-wide variomics libraries for potential compound resistant clones was performed as described previously (Huang, S. et al. 2013) but with slight modifications. About 6×10$^7$ haploid cells was plated on solid SC-Ura medium buffered with HEPES at pH 7.0, which contained compound at a concentration of 20 μM (~7 μg/ml) and incubated at 30° C. for 3 days.

HIP-HOP Library: The yeast deletion collection used here comprises of approximately 5900 individually barcoded heterozygous diploid strains (HaploInsufficiency Prolifing) and ~4800 homozygous diploid strains (HOmozygous deletion Profiling) (Pierce, S. E. et al. 2007). Pools of approximately equal strain abundance were generated by robotically pinning (S and P Robotics, Ontario, Canada) each strain (from frozen stocks) onto YPD agar plates as arrays of 384 strains/plate. After two days of growth at 30° C., colonies were collected from plates by flooding with YPD and aliquoted at optical density of 2 (at 600 nm). The fitness of each strain in each experimental pool was assessed as described (Pierce, S. E. et al. 2007). The dose of compound that resulted in 15% growth inhibition in BY4733 (the parent strain of the yeast deletion collection) was determined by performing a dose response over the course of 16 h of growth at 30° C. Screens of the homozygous deletion collection were performed for 5 generations of growth in compound, and screens of the Heterozygous deletion collection were collected following 20 generations of growth. Cells were processed as described (Proctor, M. et al. 2011). Briefly genomic DNA was extracted from each sample, subjected to PCR to amplify the unique barcode identifiers and the abundance of each barcode was determined by quantifying the microarray signal as described. A ranked list of all genes in the genome was generated for each experiment and then compared using gene set enrichment analysis or GSEA according to Lee (Lee, A Y et al. 2014).

C6-NBD-Ceramide Staining

The Golgi apparatus of C. neoformans and C. albicans was stained with C6-NBD-ceramide using a previously described protocol (Kmetzsch, L. et al. 2011), based on the property that this fluorescent lipid accumulates at the Golgi of either living or fixed cells (Pagano R. E. et al. 1989). Control or compound-treated (4 μg/ml) yeast cells were fixed with 4% paraformaldehyde in PBS. Cell suspensions were then washed with the same buffer and incubated with C6-NBD-ceramide (20 mM) for 16 h at 4° C. The cells were then incubated with bovine serum albumin (BSA, 1%) at 4° C. for 1 h to remove the excess of C6-NBD-ceramide. After washing with PBS, the cells were incubated with 10 μg/ml DAPI (Sigma-Aldrich, St. Louis, USA) for 30 min at room temperature. The cells were washed again with PBS and stained cell suspensions were mounted over glass slides as described above and analyzed under an Axioplan 2 (Zeiss, Germany).

Statistical Analysis

Statistical analysis for survival studies was performed using Student-Newman-Keels t test for multiple comparisons using INSTAT. Statistical analysis for tissue burden and for trophic form and asci counts was performed using the analysis of variance (ANOVA). Additional statistic was performed using Student t test.

Comparison Studies

For survival studies, 4-week old CBA/J female mice (Jackson Laboratory, Bar Harbor, ME) were used. Total of forty mice were infected by tail vein injection of 200 μL containing 10$^5$ cells of C. neoformans H99 and were randomly separated into 5 groups (8 mice per group). Treatment started within 2 hours of infection. The treated mice received an intraperitoneal injection of 1.2 mg/kg/day of compound and amphotermcin B or 10 mg/kg/day of fluconazole in 100 μL final volume of PBS containing 0.4% DMSO. Untreated mice, received 100 μL of PBS/0.4% DMSO. Mice were fed ad-libitum and monitored closely for sign of discomfort and meningitis. Mice showing abnormal gait, lethargy, tremor, significant loss of body weight, or inability to reach water or food were sacrificed and survival was counted until that day.

Sample Preparation for Transmission Electron Microscopy (TEM)

Sample preparation for Transmission electron Microscopy (TEM) was performed similar to the methods of Heung (Heung et al. 2005) with minor modifications. Briefly, C. neoformans (H99) were grown in YNB (pH=7.4) at 37° C. and 5% $CO_2$ and treated for 6 hours with compound (4 μg/mL), non-treated cells were also included as control. The cells were pelleted at 3000 rpm (1700 g) and fixed with 2% EM glutaraldehyde in PBS solution for 1 hour. Samples were then washed in PBS, placed in 1% osmium tetroxide in 0.1M PBS, dehydrated in a graded series of ethyl alcohol and embedded in Embed812 resin. Ultrathin sections of 80 nm were cut with a Leica EM UC7 ultramicrotome (Leica Microsystems Inc., Buffalo Grove, IL) and placed on uncoated mesh copper grids. Sections were then counter-stained with uranyl acetate and lead citrate and viewed with a FEI Tecnail2 BioTwinG2 electron microscope (FEI, Hillsboro, Oregon) Transmission Electron Microscope (TEM). Digital images were acquired with an AMT XR-60 CCD Digital Camera system.

Pre-Screening

For the compound revertant screen, the drug-sensitive RYO0622 haploid strain was used (Suzuki, Y., et al. 2011). To determine the $IC_{100}$ dose of compound (at which yeast cell growth is inhibited at 100% upon drug exposure), 20 ul of RYO0622 cells (at $OD_{600}$ 1$^{-4}$) were plated on solid synthetic complete (SC) media alone, with DMSO, or with a range of compound doses (0.2, 0.4, 0.8, 1.6 and 3.2 mM) in a 46-well plate. The plate was incubated for 2 days at 30° C. in the dark.

Revertant Screening Assay

RYO622 cells were cultured to mid-log phase (~$OD_{600}$ 0.5) in liquid SC media before adjusting the cell density to 1×10$^6$ cells/ml (equivalent to $OD_{600}$~0.1). One ml of cells was plated on solid SC media containing DMSO solvent control (0.26% v/v) or compound (at 0.4 mM IC100 dose) and incubated at 30° C. in the dark. A lawn of cells grew on the solvent control, while only a single compound-resistant colony was identified after 9 days. Longer incubation did not result in the appearance of further resistant clones. To confirm compound resistance, single colonies isolated from the compound containing SC media were plated onto fresh solid SC medium containing 0.4 mM compound and incubated for 2 days at 30° C. in the dark. Robust compound-resistant cells wore seen.

Yeast Genomic DNA Preparation

Genomic DNA was extracted from RYO0622 and compound-resistant cells using the Puregene kit (Qiagen), according to the manufacturer's instructions.

Next-Generation Sequencing of Compound-Resistant RYO0622

Genomic DNA was quantified using Qubit fluorometry (Life Technologies) and diluted for sequencing library preparation using Nextera XT library preparation kit according to the manufacturer's instructions (Illumina). Libraries were pooled and sequenced on a single MiSeq lane, generating paired-end 150 bp reads.

Mapping & Variant Calling

Raw FASTQ paired-end reads for the parent (RYO0622) and the revertant were independently aligned to NCBI sacCer3 (genbank/genomes/Eukaryotes/fungi/Saccharomyces_cerevisiae/SacCer_Apr2011) reference genome using bwa mem v0.7.4-r385 with the -M flag to mark shorter split hits as secondary for compatibility with Picard (Li, H. & Durbin, H. 2009). Resultant SAM files were converted to BAM format using samtools v1.1 and sorted by coordinate using Picard v1.96 (SortSam) (http://picard.sourceforge.net). PCR duplicate reads were filtered out using Picard MarkDuplicates (10.24% estimated duplication) and indexed using Picard BuildBamIndex. To call single nucleotide variants (SNVs), we ran the GATK Unified Genotyper v2.1-8 (McKenna, A., et al. 2010) with the NCBI sacCer3 reference genome, stand_call_conf=30, and stand_emit_conf=10 (DePristo, M. A., et al. 2011). The ploidy parameter was set to 1 since the parent and revertant are in haploid state. Since a database of known indels and known SNPs was not available, we did not perform re-alignment around known indels and quality score recalibration.

TEM. Sample preparation for Transmission electron Microscopy (TEM) was performed similar to the methods of Hueng et al. with minor modifications (Heung, L. J. et al 2005). Briefly, C. neoformans (H99) were grown in YNB (pH-7.4) at 37° C. and 5% $CO_2$ and treated for 6 hours with compound (4 µg/mL), non-treated cells were also included as control. The cells were pelleted at 3000 rpm. (1700 g) and fixed with 2% EM glutaraldehyde in PBS solution for 1 hour. Samples were then washed in PBS, placed in 1% osmium tetroxide in 0.1M PBS, dehydrated in a graded series of ethyl alcohol and embedded in Embed812 resin. Ultrathin sections of 80 nm were cut with a Leica EM UC7 ultramicrotome (Leica Microsystems Inc., Buffalo Grove, IL) and placed on uncoated mesh copper grids. Sections were then counterstained with uranyl acetate and lead citrate and viewed with a FEI Tecnail2 BioTwinG2 electron microscope (FBI, Hillsboro, Oregon) Transmission Electron Microscope (TEM). Digital images were acquired with an AMT XR-60 CCD Digital Camera system.

Generation of compound-resistant strains. For the generation of compound-resistant strains, the drug-sensitive S. cerevisiae RYO0622 haploid strain was used (Suzuki, Y. et al. 2011). Prescreening studies were performed to determine the $IC_{100}$ dose of compound for this strain (the 100% inhibitory concentration. [$IC_{100}$] at which 100% yeast LL growth is inhibited upon drug exposure). For this screening, 20 µl of RYO0622 cells (at an $OD_{600}$ of $10^{-4}$) were plated on solid synthetic complete (SC) medium alone or with DMSO or with various compound concentrations (67, 133, 266, 533, and 1,066 µg/ml) in a 48-well plate. The plates were incubated for 2 days at 30° C. in the dark. These studies revealed an $IC_{100}$ dose of 133 µg/ml. Screening for the compound-resistant mutants was performed by growing the RYO0622 cells to mid-log phase ($OD_{600}$ of ~0.5) in liquid SC medium before adjusting the cell density to $1\times10^6$ cells/ma (equivalent to an $OD_{600}$ of ~0.1). One milliliter of cells was plated on solid SC medium containing DMSO solvent control (0.26% [vol/vol]) or compound (133 µg/ml $IC_{100}$ dose) and incubated at 30° C. in the dark. A lawn of cells grew on the solvent control, while seven compound-resistant colonies were identified after 9 days. Longer incubation did not result in the appearance of further resistant colonies. To confirm compound resistance, single colonies isolated from the compound-containing SC medium were plated onto fresh solid SC medium containing 133 µg/ml compound and incubated for 2 days at 30° C. in the dark. Robust compound-resistant cells were seen.

Next-generation sequencing of compound-resistant strains. Genomic DNA was extracted from RYO0622 and compound-resistant cells using a standard yeast DNA extraction protocol (Hoffman, C. S. et al. 1987). Genomic DNA samples were quantified using Qubit fluorometry (Life Technologies) and diluted for sequencing library preparation using a Nextera XT library preparation kit according to the manufacturer's instructions (Illumina San Diego, CA). For the initial round of sequencing, individual sequencing libraries were prepared for the parent and a single compound-resistant clone. These libraries were pooled and sequenced on a single MiSeq lane (Illumina), generating paired-end 150-bp reads. Further compound-resistant colonies were obtained in a second screen, and their DNAs were pooled at equal concentrations before preparation of a single sequencing library for the pool. This pool was sequenced alongside a new library for the parent strain on a single HiSeq 2500 lane (Illumina), generating paired-end 100-bp reads.

Mapping and variant calling. Raw FASTQ paired-end reads for the parent (RYO0622) and the compound-resistant pool were independently aligned to the NCBI sacCer3 reference genome using bwa mem v0.7.4-r385 (Li, R., Yu, C. et al. 2009) with the -M flag to mark shorter split hits as secondary for compatibility with Picard. Resultant SAM files were converted to BAN format using samtools v1.1 and sorted by coordinate using Picard v1.96 (SortSam). PCR duplicate reads were filtered out using Picard MarkDuplicates and indexed using Picard BuildBamIndex. To call single nucleotide variants (SNVs), the GATK Unified Genotyper v2.1-8 (McKenna, A. et al. 2010) was ran with the NCBI sacCer3 reference genome, stand_call_conf=30, and stand_emit_conf=10 (DePristo, M. A. et al. 2011). The ploidy parameter was set at 1, since the parent and resistant strains are in haploid state. Realignment around known indels and quality score recalibration was not performed, since a database of known indels and known single nucleotide polymorphisms (SNPs) is not available.

Validation of compound-resistant yeast mutants. Four yeast genes (ALP5, COS111, MKK1, and STE2) were selected based on the high-quality variant calls present in the compound-resistant pool. To confirm compound resistance, the individual haploid Δap15, Δcos111, Δmkk1 and Δste2 deletion mutants were assayed for growth fitness after treatment with compound. Unrelated drug controls, including methyl methane sulfonate (MMS) (cytotoxic) and fluconazole (antifungal) were assayed in parallel. Strains were cultured to mid-log phase ($OD_{600}$ of ~0.5) in liquid YPD medium before adjusting the cell density to an $OD_{600}$ of 0.0625 with YPD medium. The cells were transferred to 96-well plates containing 100 µl of YPD with DMSO solvent control (2% [vol/vol]), compound (6 to 733 µg/ml), MMS (10 µg/ml to 625 µg/ml), or fluconazole (2 to 306 µg/ml) and incubated at 30° C. for 24 h. The fitness of individual strains was measured, using a spectrophotometer plate reader (Tecan GENios, Chapel Hill, NC) to read $OD_{600}$ over 24 h as a proxy for cell growth. Relative growth inhibition was calculated by the average rate after normalizing the $OD_{600}$ values in drug wells against the DMSO control wells on each assay plate.

Example 1

Synthesis

General Synthesis of Compounds

The benzaldehyde (1 mmol, 2 ml ethanol) and the benzohydrazide (1 mmol in 2 ml hot ethano) were combined. The product generally crystallize within seconds. After 30 minutes at room temperature the product was collected by filtration (Yield: 80 to 95%). Homogeneity of the product was confirmed by thin layer chromatography (TLC) on silicagel $F_{254}$ (Merck KGaA, Darmstadt, Germany) in two different solvent systems benzene/acetic acid 9:1 v/v and hexane/ethylacetate 1:3 v/v. If impurities were present the product was recrystallized from ethanol. Alternatively, the reaction proceeds for 24 h at 4° C. and the solvent was completely evaporated and the product crystallized from ethyl acetate. Products were analyzed by TLC as described above.

Synthesis of 1

To a solution of 2-methylbenzoic hydrazide (0.66 mmol), 2-hydroxy-5-bromobenzaldehyde (0.72 mmol) in methanol (3 mL) was added 3 drops of glacial acetic acid. The reaction mixture was stirred at room temperature overnight. Addition of water to the reaction mixture resulted in precipitation of the product, which was filtered, washed with water and dried to give pure product as white solid. (95% yield); $^1$H NMR (500 MHz, DMSO-d6) δ 2.38 (s, 3H), 6.90 (d, 1H, J=8.8 Hz), 7.28-7.32 (m, 3H), 7.37-7.43 (m, 2H), 7.47 (d, 1H, J=7.5 Hz), 7.78 (s, 1H), 8.47 (s, 1H), 11.19 (s, 1H), 12.05 (s, 1H). Compound 2, 13 and 17 were synthesized by an analogous method using the appropriate starting materials for each.

Example 2

PK/PD: Killing Curve Versus MIC $K_{app}$ Coefficient Analysis

| Compound | MIC | $K_{app}$* | A549 | $SI_{MIC}$ |
|---|---|---|---|---|
| 1 | 1 | 0.024 | 32 | 32 |
| 2 | 0.25 | −0.142 | 64 | 64 |
| 13 | 0.06 | −0.428 | >128 | 4266.6 |
| 17 | 0.5 | 0.077 | 16 | 32 |

*$K_{app} = K_0 - K_i(C - C_i)$

Example 3

Kill Characteristics of 1 and 2

Figure 1B:
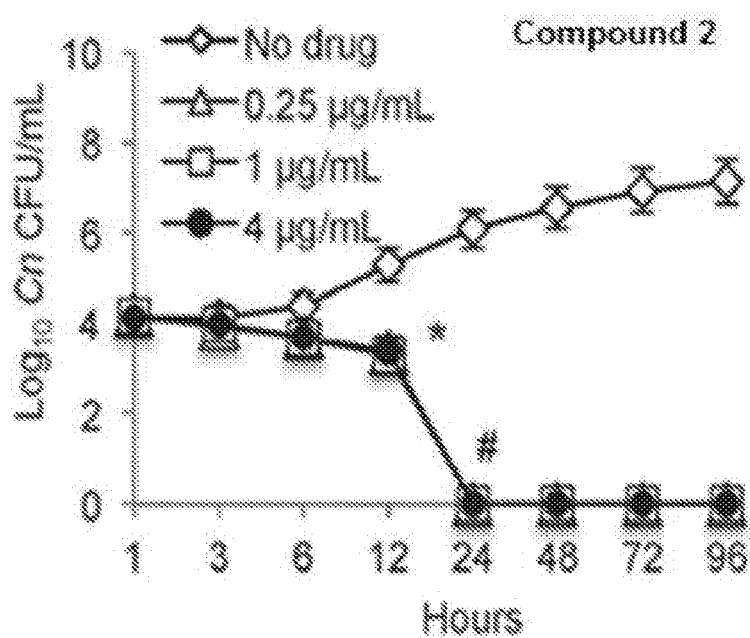
FIG. 1B. Compound 2 killed *C. neoformans* in a time dependent manner.

Compound 1 killed *C. neoformans* in a concentration dependent manner (see FIG. 1A). Compound 2 also killed *C. neoformans* in a time dependent manner (see FIG. 1B).

Example 4

Fungicidal Data

TABLE 1

| Structure | IC$_{80}$ (μg/mL) | Killing assay 48 H (μg/mL) | A549 | HepG2 | SI-A549/ MIC | SI-HepG2/ MIC |
|---|---|---|---|---|---|---|
| (quinoline-carbohydrazide with 2-hydroxy-3,5-dibromobenzylidene) | 0.25 | Fungistatic | 32 | 32 | 128 | 128 |
| (2-hydroxy-5-bromobenzoyl hydrazone with 2-hydroxy-5-methylbenzaldehyde) | 0.25 | 0.5 | 16 | 16 | 64 | 64 |
| (2,4-dibromobenzoyl hydrazone with 2-hydroxy-5-methylbenzaldehyde) | 1 | 1 | 32 | 16 | 32 | 16 |

TABLE 1-continued

| Structure | IC$_{80}$ (μg/mL) | Killing assay 48 H (μg/mL) | A549 | HepG2 | SI-A549/ MIC | SI-HepG2/ MIC |
|---|---|---|---|---|---|---|
| (2,5-dibromo-benzoyl hydrazone with 2-hydroxy-5-methylbenzaldehyde) | 1 | 0.5 | 32 | 32 | 32 | 32 |
| (3,5-dibromo-2-hydroxy-benzoyl hydrazone with 2-hydroxy-5-methylbenzaldehyde) | 0.25 | 0.25 | 4 | 8 | 16 | 32 |
| (2,4-dibromo-benzoyl hydrazone with 5-chloro-2-hydroxybenzaldehyde) | 0.25 | 1 | 64 | 64 | 256 | 256 |
| (2,3-difluoro-benzoyl hydrazone with 5-chloro-2-hydroxybenzaldehyde) | 1 | 0.5 | 72 | 32 | 72 | 32 |

*Units are μg/ml for A549, HepG2, SI-A549/MIC and SI-HepG2/MIC.

TABLE 2

| Structure | IC$_{80}$ (μg/mL) | Killing assay 48 H (μg/mL) | A549 | HepG2 | SI-A549/ MIC | SI-HepG2/ MIC |
|---|---|---|---|---|---|---|
| (2,5-dibromo-benzoyl hydrazone with 5-chloro-2-hydroxybenzaldehyde) | 0.25 | 0.12 | 59 | 32 | 236 | |

TABLE 2-continued
| Structure | IC$_{80}$ (μg/mL) | Killing assay 48 H (μg/mL) | A549 | HepG2 | SI-A549/ MIC | SI-HepG2/ MIC |
|---|---|---|---|---|---|---|
| 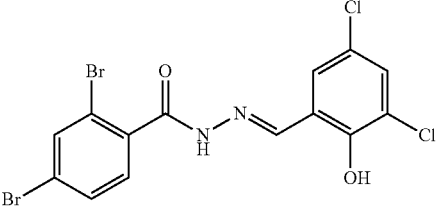 [SMILES: O=C(N/N=C/c1cc(Cl)cc(Cl)c1O)c1ccc(Br)cc1Br] | 1 | 0.5 | >64 | 64 | 128 | 64 |
| 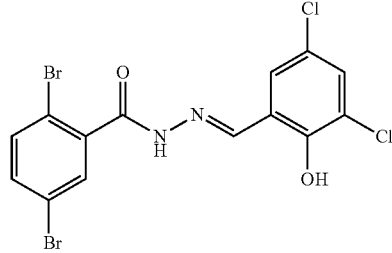 [SMILES: O=C(N/N=C/c1cc(Cl)cc(Cl)c1O)c1cc(Br)ccc1Br] | 0.5 | 0.25 | 32 | 32 | 64 | 64 |
| 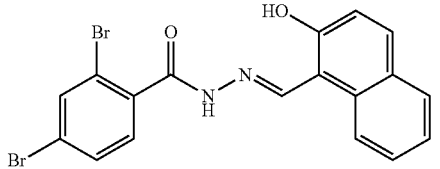 [SMILES: O=C(N/N=C/c1c(O)ccc2ccccc12)c1ccc(Br)cc1Br] | 0.12 | 0.5 | 16 | >32 | 133.3 | 533.3 |
| 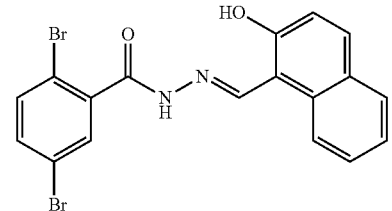 [SMILES: O=C(N/N=C/c1c(O)ccc2ccccc12)c1cc(Br)ccc1Br] | 0.25 | 0.25 | 32 | 16 | 128 | 64 |
| 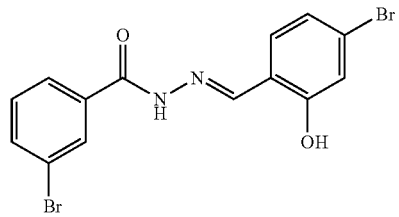 [SMILES: O=C(N/N=C/c1ccc(Br)cc1O)c1cccc(Br)c1] | 0.5 | 0.25 | >32 | 9 | 128 | 18 |
| 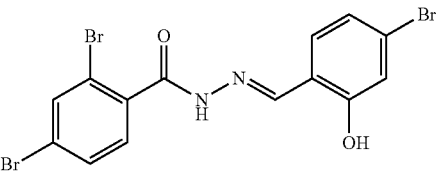 [SMILES: O=C(N/N=C/c1ccc(Br)cc1O)c1ccc(Br)cc1Br] | 0.06 | 0.12 | >32 | >64 | 1066 | 2133.3 |
*Units are μg/ml for A549, HepG2, SI-A549/MIC and SI-HepG2/MIC.

TABLE 3

| Structure | IC$_{80}$ (µg/mL) | Killing assay 48 H (µg/mL) | A549 | HepG2 | SI-A549/ MIC | SI-HepG2/ MIC |
|---|---|---|---|---|---|---|
| (2,3-difluoro-benzoyl, 4-Br-2-OH-benzylidene hydrazide) | 0.5 | 0.25 | 16 | 16 | 32 | 32 |
| (4-Br-benzoyl, 4-Br-2-OH-benzylidene hydrazide) | 0.06 | Fungistatic | 16 | 32 | 266.6 | 533.3 |
| (2,5-diBr-benzoyl, 4-Br-2-OH-benzylidene hydrazide) | 0.12 | 0.25 | 32 | 16 | 266.6 | 133.3 |
| (3,5-diBr-2-OH-benzoyl, 4-Br-2-OH-benzylidene hydrazide) | 0.06 | Fungistatic | 32 | 32 | 533.3 | 533.3 |
| (2,4-diBr-benzoyl, 5-Br-2-OH-benzylidene hydrazide) | 0.12 | 0.12 | >32 | 59 | 533.3 | 491.66 |
| (2,5-diBr-benzoyl, 5-Br-2-OH-benzylidene hydrazide) | 0.25 | 1 | 16 | 32 | 64 | 128 |

*Units are µg/ml for A549, HepG2, SI-A549/MIC and SI-HepG2/MIC.

Example 5

Administration of the Compound

An amount of the compound of the present invention is administered to a subject afflicted with a fungal infection. The amount of the compound is effective to treat the subject.

An amount of the compound of the present invention is administered to a subject afflicted with a fungal infection. The amount of the compound is effective to treat the subject by inhibiting sphingolipid synthesis in the fungus without substantially inhibiting sphingolipid synthesis in the subject.

An amount of the compound of the present invention in combination with an anti-fungal agent are administered to a subject afflicted with a fungal infection. The amount of the compound and the agent are effective to treat the subject.

Example 6

Assessment of Efficacy of Compound as Add-On Therapy to Anti-Fungal Agents

The add-on therapy provides a synergistic effect, and allows for lower doses with reduced side effects and resistance.

Periodic administration of the compound of the present invention as an add-on therapy for a subject afflicted with a fungal infection who is already receiving treatment with an anti-fungal agent provides a clinically meaningful advantage and is more effective (provides at least an additive effect or more than an additive effect) in treating the subject than when the anti-fungal agent is administered alone (at the same dose).

Periodic administration an anti-fungal agent as an add-on therapy for a human patient afflicted with a fungal infection who is already receiving a compound of the present invention provides a clinically meaningful advantage and is more effective (provides at least an additive effect or more than an additive effect) in treating the subject than when the compound is administered alone (at the same dose).

The add-on therapies also provide efficacy (provides at least an additive effect or more than an additive effect) in treating the subject without undue adverse side effects or affecting the safety of the treatment. As compared to when each agent is administered alone:

1. The add-on therapy is more effective (provides an additive effect or more than an additive effect) in killing the fungus; and/or 2. The add-on therapy is more effective (provides an additive effect or more than an additive effect) in slowing the growth of the fungus.

Example 7

Synthesis and Characterization

Chemical Synthesis and Characterization of Aromatic Acylhydrazones of this Invention 4-Bromo-N'-(2-hydroxy-5-trifluoromethoxybenzylidene)benzohydrazide (A1)

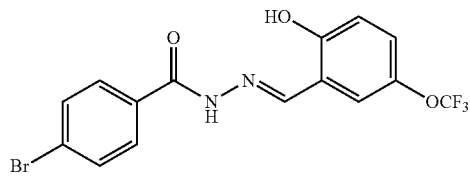 [SMILES: O=C(N/N=C/c1cc(OC(F)(F)F)ccc1O)c1ccc(Br)cc1]

To a solution of 4-bromobenzoic hydrazide (100 mg, 0.47 mmol), 5-trifluoromethoxysalicylaldehyde (102 mg, 0.49 mmol) in methanol (2 mL) was added 3 drops of glacial acetic acid. The reaction mixture was stirred at room temperature overnight. Addition of water to the reaction mixture resulted in precipitation of the product, which was filtered, washed with water and dried, to give pure product as white solid (93% yield); m.p. 213-214° C.; 1H NMR (500 MHz DMSO-$d_6$) δ 7.02 (d, 1H, J=9 Hz), 7.30 (dd, 1H, J=8.9, 2.6 Hz), 7.64 (s, 1H), 7.77 (d, 2H, J=8.5 Hz), 7.89 (d, 2H, J=8.5 Hz), 8.67 (s, 1H), 11.25 (s, 1H), 12.23 (s, 1H); $^{13}$C NMR (125 MHz DMSO-$d_6$) δ 117.73, 119.19, 120.21, 120.37, 121.22, 123.25, 124.34, 125.83, 129.77, 131.60, 131.07, 140.67, 145.61, 156.06, 162.06; $^{19}$F NMR (376 MHz DMSO-$d_6$) δ 57.30 (s, 3F); HRMS (ESI) m/z calcd for $C_{15}H_{10}BrF_3N_2O_3H^+$: 402.99, Found: 402.991 (Δ=−2.47 ppm).

The same procedure was followed for the rest of the compounds.

4-Bromo-N'-(5-fluoro-2-hydroxybenzylidene)benzohydrazide (A2)

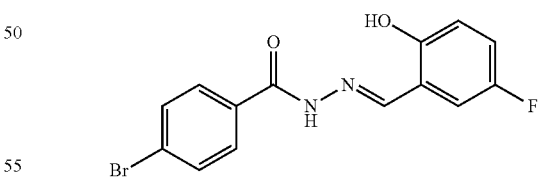

White solid (88% yield); m.p.>220° C.; $^1$H NMR (500 MHz DMSO-$d_6$) δ 6.92-6.94 (m, 1H), 7.15 (td, 1H, J=8.6, 3.2 Hz), 7.44 (dd, 1H, J=9.4 3.1 Hz), 7.76 (d, 2H, J=8.5 Hz), 7.09 (d, 2H, J=0.5 Hz), 8.63 (s, 1H), 10.94 (s, 1H), 12.20 (s, 1H); $^{13}$C NMR (125 MHz DMSO-$d_6$) δ 113.61, 113.80, 117.58, 117.64, 118.01, 119.74, 119.80, 125.80, 129.74, 131.58, 131.86, 146.34, 153.57, 154.39, 156.26, 161.97; $^{19}$F NMR (376 MHz DMSO-dd 3-125.06 (s, 1F); HRMS (ESI) m/z calcd for $C_{14}H_{10}BrFN_2O_2H^+$: 336.9982, Found: 336.9996 (Δ=−3.95 ppm).

2,4-Dibromo-N'-(2-hydroxy-5-trifluoromethoxybenzylidene)benzohydrazide (A3)

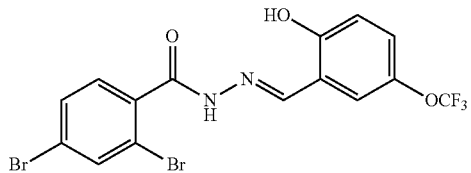 [SMILES: O=C(N/N=C/c1cc(OC(F)(F)F)ccc1O)c1ccc(Br)cc1Br]

White solid (99% yield); m.p. 170-172° C.; $^1$H NMR (500 MHz DMSO-$d_6$) δ 6.91 (d, 1H, 40%, J=8.8 Hz), 7.01 (d, 1H, 60%, J=8.9 Hz), 7.16-7.17 (m, 1H, 50%), 7.19-7.20 (1H, m, 20%), 7.30 (dd, 1H, 60%, J=9, 2.8 Hz), 7.40 (d, 1H, 40%, J=8.2 Hz), 7.54 (d, 1H, 60%, J=8.2 Hz), 7.64 (s, 1H, 60%), 7.69 (dd, 1H, 40%, J=8.2, 1.8 Hz), 7.74 (dd, 1H, 60%, J=8.2, 1.8 Hz), 7.97 (s, 1H, 35%), 8.02 (s, 1H, 40%), 8.50 (s, 1H, 60%), 10.28 (s, 1H, 40%), 11.03 (s, 1H, 60%), 12.18 (s, 1H, 63%), 12.20 (s, 1H, 34%); $^{13}$C NMR (125 MHz DMSO-$d_6$) δ 117.54, 117.73, 113.54, 119.06, 119.17, 119.86, 119.94, 120.19, 120.61, 120.63, 121.09, 121.21, 123.78, 123.86, 124.56, 130.15, 130.57, 130.80, 130.87, 134.01, 134.84, 136.08, 137.20, 140.69, 140.70, 140.85, 145.36, 155.16, 155.96, 162.52, 168.45; $^{19}$F NMR (376 MHz DMSO-$d_6$) δ −57.31, −57.40; HRMS (ESI) m/z calcd for $C_{15}H_9Br_2F_3N_2O_3H^+$: 480.9005, Found: 480.9013 (Δ=−1.74 ppm).

2,4-Dibromo-N'(5-fluoro-2-hydroxybenzylidene)benzohydrazide (A4)

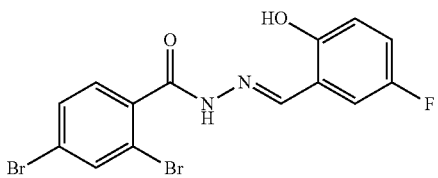 [SMILES: O=C(N/N=C/c1cc(F)ccc1O)c1ccc(Br)cc1Br]

White solid (96% yield); m.p. 182-183° C.; $^1$H NMR (500 MHz DMSO-$d_6$) δ 6.83 (dd, 1H, 40%, J=9, 4.7 Hz), 6.94 (dd, 1H, 60%, J=9, 4.7 Hz), 6.98 (dd, 1H, 40%, J=9.4, 3.2 Hz), 7.06 (td, 1H, 40%, J=8.5, 3.3 Hz), 7.16 (td, 1H, 60%, J=8.5, 3.3 Hz), 7.41 (d, 1H, 40%, J=8.2 Hz), 7.44 (dd, 1H, 60%, J=9.4, 3.2), 7.54 (d, 1H, 60%, J=8.2 Hz), 7.70 (dd, 1H, 40%, J=8.2, 1.9 Hz), 7.74 (dd, 1H, 60%, J=8.2, 1.9 Hz), 8.00 (s, 1H, 35%), 8.02 (s, 1H, 55%), 8.27 (s, 1H, 40%), 8.47 (s, 1H, 60%), 9.90 (s, 1H, 40%), 10.71 (s, 1H, 60%), 12.15 (s, 1H, 66%), 12.17 (s, 1H, 33%); $^{13}$C NMR (125 MHz DMSO-$d_6$) δ 111.98, 112.18, 113.20, 113.39, 117.44, 117.50, 117.58, 117.65, 117.78, 117.97, 118.25, 118.43, 119.75, 119.81, 120.18, 120.24, 120.63, 122.66, 123.76, 130.16, 130.66, 130.78, 130.86, 134.13, 134.82, 136.08, 137.16, 141.81, 146.09, 152.80, 153.48, 154.32, 154.41, 156.18, 156.27, 162.45, 168.29; $^{19}$F NMR (376 MHz DMSO-$d_6$) δ −124.76 (s, 1F), −124.91 (s, 1F); HRMS (ESI) m/z calcd for $C_{14}H_9Br_2FN_2O_2H^+$: 414.9088, Found: 414.9095 (Δ=−1.7 ppm).

3-Difluoromethoxy-N'-(5-bromo-2-hydroxybenzylidene)benzohydrazide (A5)

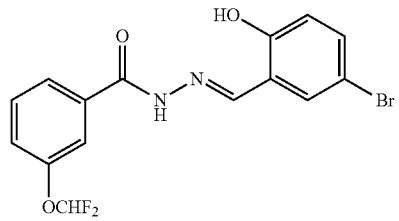 [SMILES: O=C(N/N=C/c1cc(Br)ccc1O)c1cccc(OC(F)F)c1]

Yellow solid (90% yield); m.p. 166-168° C.; $^1$H NMR (500 MHz DMSO-$d_6$) δ 6.91 (d, 1H, 90%, J=8.8 Hz), 6.95 (d, 1H, 10%, J=8.8 Hz), 7.18 (s, 1H, 25%), 7.33 (s, 1H, 50%), 7.42-7.44 (m, 2H, 90%), 7.48 (s, 1H, 25%), 7.54-7.56 (m, 2H, 10%), 7.61 (t, 1H, 100%, J=8 Hz), 7.72 (s, 1H, 90%), 7.81-7.83 (m, 2H, 100%, 90%), 7.90 (s, 1H, 10%), 8.63 (s, 1H, 90%), 8.93 (s, 1H, 10%), 11.13 (s, 1H, 10%), 11.20 (s, 1H, 90%), 12.22 (s, 1H, 90%); $^{13}$C NMR (125 MHz DMSO-$d_6$) δ 110.48, 110.56, 114.26, 117.94, 118.36, 118.68, 118.91, 120.57, 121.33, 122.26, 124.45, 130.23, 130.41, 131.57, 133.70, 134.65, 135.49, 145.84, 150.94, 150.96, 156.41, 157.66, 160.76, 161.83; $^{19}$F NMR (376 MHz DMSO-$d_6$) δ −82.16 (s, 2F); HRMS (ESI) m/z calcd for $C_{15}H_{11}BrF_2N_2O_3H^+$: 384.9994, Found: 384.9996 (Δ=−0.49 ppm).

3-Difluoromethoxy-N'-(3,5-dibromo-2-hydroxybenzylidene)benzohydrazide (A6)

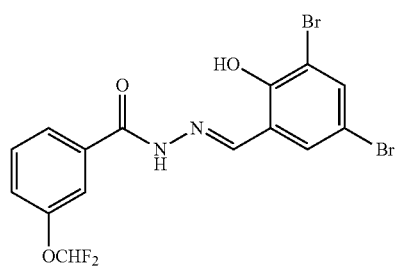 [SMILES: O=C(N/N=C/c1cc(Br)cc(Br)c1O)c1cccc(OC(F)F)c1]

Yellow solid (99% yield); m.p. 143-147° C.; $^1$H NMR (500 MHz DMSO-$d_6$) δ 7.19 (s, 1H, 25%), 7.34 (s, 1H, 50%), 7.46 (d, 1H, 90%, J=8 Hz), 7.49 (s, 1H, 25%), 7.63 (t, 1H, 100%, J=8 Hz), 7.73 (s, 1H, 100%), 7.83-7.96 (m, 3H, 100%), 8.54 (s, 1H, 90%), 9.06 (s, 1H, 10%), 10.08 (s, 1H, 5%), 11.99 (s, 1H, 10%), 12.60 (s, 1H, 90%), 12.64 (s, 1H, 95%); $^{13}$C NMR (125 MHz DMSO-$d_6$) δ 110.44, 110.80, 111.25, 111.64, 114.22, 116.28, 118.05, 118.34, 120.35, 120.92, 122.55, 124.53, 130.50, 132.14, 133.47, 134.02, 135.69, 137.77, 147.49, 150.90, 151.00, 153.65, 154.71, 161.94, 163.98; $^{19}$F NMS. (376 MHz DMSO-$d_6$) δ −82.22 (s, 2F); HRMS (ESI) m/z calcd for $C_{15}H_{10}Br_2F_2N_2O_3H^+$: 462.9099, Found: 462.91 (Δ=−0.2 ppm).

4-Trifluoromethoxy-N'-(5-bromo-2-hydroxybenzylidene)benzohydrazide (A7)

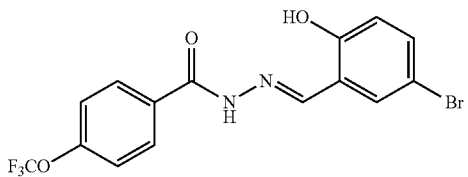 [SMILES: O=C(N/N=C/c1cc(Br)ccc1O)c1ccc(OC(F)(F)F)cc1]

Beige solid (88% yield); m.p. 199-201° C.; $^1$H NMR (500 MHz DMSO-$d_6$) δ 6.91 (d, 1H, J=8.8 Hz), 7.42-7.44 (m, 1H), 7.54 (d, 2H, J=8.3 Hz), 7.81 (s, 1H), 8.07 (d, 2H, J=8.3 Hz), 3.61 (s, 1H), 11.21 (s, 1H), 12.25 (s, 1H); $^{13}$C NMR (125 MHz DMSO-$d_6$) δ 110.47, 116.88, 118.68, 118.92, 120.83, 120.97, 121.31, 123.02, 130.10, 130.28, 131.88, 133.69, 145.81, 150.74, 156.42, 161.77; $^{19}$F NMR (376 MHz DMSO-$d_6$) δ −56.64; HRMS (ESI) m/z calcd for $C_{15}H_{10}BrF_3N_2O_3H^+$: 402.99, Found: 402.9902 (Δ=−0.63 ppm).

2-Fluoro-4-trifluoromethyl-N'-(5-bromo-2-hydroxybenzylidene)benzohydrazide (A8)

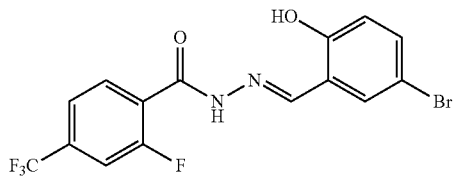 [SMILES: O=C(N/N=C/c1cc(Br)ccc1O)c1ccc(C(F)(F)F)cc1F]

Yellow solid (61% yield); m.p. 179-182° C.; $^1$H NMR (400 MHz DMSO-$d_6$) δ 6.80 (d, 1H, 30%, J=8.6 Hz), 6.90 (d, 1H, J=8.7 Hz), 7.29-7.31 (m, 2H, 25%), 7.33-7.34 (m, 1H, 17%), 7.44 (dd, 1H, 80%, J=8.8, 2.6 Hz), 7.72-7.76 (m, 2H, 75%), 7.81-7.93 (m, 2H, 100%), 8.29 (s, 1H, 33%), 8.51 (s, 1H, 77%), 10.26 (s, 1H, 30%), 11.00 (s, 1H, 70%), 12.25 (s, 1H, 30%), 12.27 (s, 1H, 70%); $^{13}$C NMR (100 MHz DMSO-$d_6$) δ 110.55, 113.87, 114.12, 118.46, 118.68, 121.24, 121.64, 123.87, 126.70, 128.19, 129.99, 131.54, 133.52, 133.96, 140.99, 145.93, 155.63, 156.38, 157.70, 159.21, 160.21, 165.61; $^{19}$F NMR (376 MHz DMSO-$d_6$) 3-61.33 (s, 3F), −61.46 (s, 3F), −111.26 (s, 1F), −111.49 (s, 1F); HRMS (ESI) m/z calcd for $C_{15}H_9BrF_4N_2O_2H^+$: 404.9856, Found: 404.9864 (Δ=−1.84 ppm).

2-Fluoro-4-trifluoromethyl-N'-(3,5-dibromo-2-hydroxybenzylidene)benzohydrazide (A9)

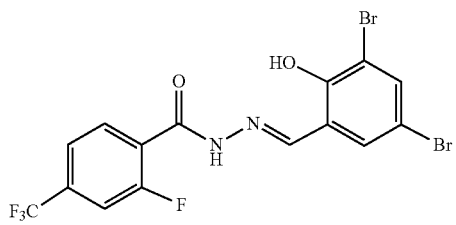 [SMILES: O=C(N/N=C/c1cc(Br)cc(Br)c1O)c1ccc(C(F)(F)F)cc1F]

Yellow solid (74% yield); m.p. 192-195° C.; $^1$H NMR (400 MHz DMSO-$d_6$) δ 7.52 (s, 1H, 15%), 7.74 7.97 (m, 1H, 85%, 4H, 100%), 8.27 (s, 1H, 20%), 8.46 (s, 1H, 80%), 10.2 (s, 1H, 25%), 12.34 (s, 1H, 75%), 12.53 (s, 1H, 15%), 12.67 (s, 1H, 80%); $^{13}$C NMR (100 MHz DMSO-$d_6$) δ 110.57, 171.17, 111.92, 113.96, 114.21, 120.89, 121.58, 121.69, 121.73, 122.27, 126.01, 126.17, 130.49, 130.65, 131.66, 131.69, 132.84, 132.92, 133.16, 133.25, 135.68, 135.96, 143.57, 148.06, 152.33, 153.62, 157.78, 159.35, 160.29, 165.41; $^{19}$F NMR (376 MHz DMSO-$d_6$) δ −61.34 (s, 3F), −61.50 (s, 3F), −111.16 (s, 1F), −111-93 (s, 1F); HRMS (ESI) m/z calcd for $C_{15}H_8Br_2F_4N_2O_2H^+$: 482.8961, Found: 482.8958 (Δ=0.69 ppm).

N'-(3,5-dibromo-2-hydroxybenzylidene)quinolinylhydrazide (A10)

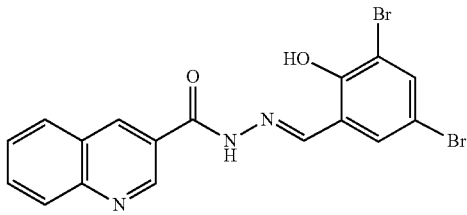 [SMILES: O=C(N/N=C/c1cc(Br)cc(Br)c1O)c1cnc2ccccc2c1]

Beige solid (99% yield); m.p.>215° C.; $^1$H NMR (700 MHz DMSO-$d_6$) δ 7.33 (t, 1H, J=7.9 Hz), 7.85 (dd, 2H, J=13.4, 2.4 Hz), 7.91 (t, 1H, J=7.7 Hz), 8.12 (d, 1H, J=8.5 Hz), 8.16 (d, 1H, J=7.8 Hz), 8.57 (s, 1H), 8.95 (s, 1H), 9.34 (s, 1H), 12.63 (s, 1H), 12.85 (s, 1H); $^{13}$C NMR (175 MHz DMSO-$d_6$) δ 110.50, 111.33, 120.96, 125.11, 126.36, 127.72, 128.86, 129.29, 131.80, 132.19, 135.77, 136.54, 147.50, 148.79, 153.70, 161.75.

4-Cyano-N'-(3,5-dibromo-2-hydroxybenzylidene)benzohydrazide (A11)

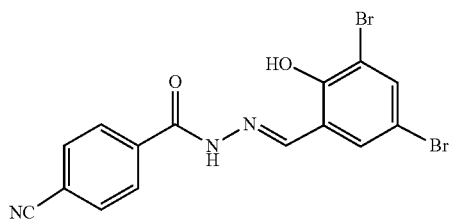 [SMILES: N#Cc1ccc(C(=O)N/N=C/c2cc(Br)cc(Br)c2O)cc1]

White solid (47% yield); m.p.>215° C.; $^1$H NMR (500 MHz DMSO-$d_6$) δ 7.83 (s, 2H), 8.05 (d, 2H, J=8.6 Hz), 8.09 (d, 2H, J=8.6 Hz), 8.53 (s, 1H), 12.64 (s, 2H); $^{13}$C NMR (125 MHz DMSO-$d_6$) δ 110.47, 111.32, 114.50, 118.17, 120.90, 128.62, 132.20, 132.65, 135.82, 136.20, 147.89, 153.70, 161.76; HRMS (ESI) m/z calcd for $C_{15}H_9Br_2N_3O_2H^+$: 421.9134, Found: 421.915 (Δ=−3.67 ppm).

2-Fluoro-4-trifluoromethoxy-N'-(5-bromo-2-hydroxybenzylidene)benzohydrazide (A12)

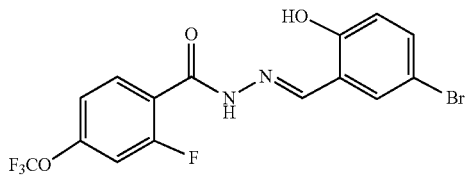 [SMILES: O=C(N/N=C/c1cc(Br)ccc1O)c1ccc(OC(F)(F)F)cc1F]

Yellow solid (57% yield); m.p. 151-152° C.; $^1$H NMR (500 MHz DMSO-$d_6$) δ 6.62 (d, 1H, 30%, J=8.8 Hz), 6.39 (d, 1H, 73%, J=3.8 Hz), 7.31-7.33 (m, 2H, 52%), 7.35 (d, 1H, 30%, J=8.8 Hz), 7.38-7.40 (m, 1H, 70%), 7.43 (dd, 1H, 67%, J=8.8, 2.6 Hz), 7.52-7.54 (m, 1H, 30%), 7.57-7.60 (m, 1H, 70%), 7.67 (t, 1H, 30%, J=8 Hz), 7.30 (s, 1H, 70%), 7.84 (t, 1H, 70%, J=8.2 Hz), 8.27 (s, 1H, 28%), 8.49 (s, 1 C, 72%), 10.27 (s, 1H, 30%), 11.03 (s, 1H, 70%), 12.15 (s, 1H, 35%), 12.19 (s, 1H, 65%); $^{13}$C NMR (125 MHz DMSO-$d_6$) δ 109.89, 110.10, 110.53, 117.17, 118.68, 121.25, 121.99, 122.01, 122.13, 128.17, 130.08, 131.01, 131.05, 131.92, 131.95, 133.45, 133.89, 140.53, 145.79, 150.32, 150.41, 155.60, 156.38, 158.48, 159.29, 160.49, 165.78; $^{19}$F NMR (376 MHz DMSO-$d_6$) δ −56.95 (s, 3F), −57.01 (s, 3F), −109.09 (s, 1F), 109.47 (s, 11F); HRMS (ESI) m/z calcd for $C_{15}H_9BrF_4N_2O_3H^+$: 420.9805, Found: 420.982 (Δ=−3.47 ppm).

2-Fluoro-4-trifluoromethoxy-N'-(3,5-dibromo-2-hydroxybenzylidene)-benzohydrazide (A13)

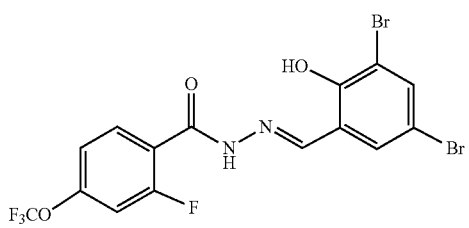 [SMILES: O=C(N/N=C/c1cc(Br)cc(Br)c1O)c1ccc(OC(F)(F)F)cc1F]

Yellow solid (62% yield); m.p. 206-207° C.; $^1$H NMR (500 MHz DMSO-$d_6$) δ 7.41 (d, 1H, J=8.6 Hz), 7.61 (d, 1H, J=8.8 Hz), 7.83 (dd, 2H, J=7.3, 2.4 Hz), 7.87 (t, 1H, J=8.3 Hz), 8.45 (s, 1H), 12.39 (s, 1H), 12.57 (s, 1H); $^{13}$C NMR (125 MHz DMSO-$d_6$) δ 109.92, 110.13, 110.52, 111.10, 111.32, 111.84, 117.18, 117.42, 118.77, 120.88, 121.31, 121.43, 122.21, 122.88, 130.60, 130.93, 132.07, 132.10, 132.19, 135.60, 135.87, 143.31, 147.78, 150.58, 150.67, 153.62, 158.57, 159.41, 160.59; 165.56; $^{19}$F NMR (376 MHz DMSO-$d_6$) δ −56.94 (s, 3F), −57.02 (s, 3F), −109.09 (s, 1F), −109.94 (s, 1F); HRMS (ESI) m/z calcd for $C_{15}H_8Br_2F_4N_2O_3H^+$: 498.8911, Found: 498.8923 (Δ=−2.57 ppm).

3-Bromo-N'-(2-hydroxy-5-trifluoromethylbenzylidene)benzohydrazide (A14)

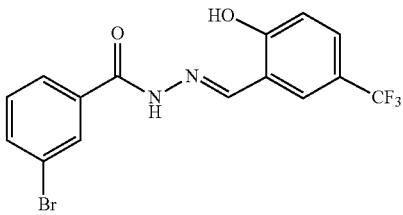 [SMILES: O=C(N/N=C/c1cc(C(F)(F)F)ccc1O)c1cccc(Br)c1]

White solid (92% yield); m.p. 175-176° C.; $^1$H NMR (400 MHz DMSO-$d_6$) δ 7.10 (d, 1H, 90%, J=8.6 Hz), 7.15 (d, 1H, 10%, J=8.5 Hz), 7.51 (t, 1H, 100%, J=7.9 Hz), 7.62 (dd, 1H, 90%, J=8.6, 1.5 Hz), 7.73 (m, 1H, 10%), 7.81 (d, 1H, 100%, J=7.8 Hz), 7.93 (d, 1H, 100%, J=7.9 Hz), 8.00 (s, 1H, 95%), 8.09 (s, 1H, 5%), 8.12 (s, 1H, 100%), 8.71 (s, 1H, 90%), 9.06 (s, 1H, 10%), 11.64 (s, 1H, 10%), 11.71 (s, 1H, 90%), 12.27 (s, 1H, 90%); $^{13}$C NMR (100 MHz DMSO-$d_6$) δ 117.19, 119.69, 119.92, 120.24, 120.57, 121.77, 123.06, 125.24, 125.75, 126.93, 128.02, 130.18, 130.82, 134.74, 134.94, 145.73, 160.00, 161.52; $^{19}$F NMR (376 MHz DMSO-$d_6$) δ −56.92 (s, 3F), −60.12 (s, 3F); HRMS (ESI) m/z calcd for $C_{15}H_{10}F_3N_2O_2H^+$: 386.9951, Found: 386.9957 (Δ=−1.78 ppm).

4-Methoxymethyl-N'-(3,5-dibromo-2-hydroxybenzylidene)benzohydrazide (A15)

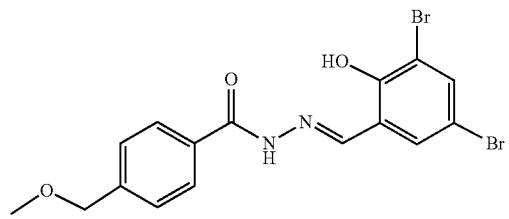 [SMILES: COCc1ccc(C(=O)N/N=C/c2cc(Br)cc(Br)c2O)cc1]

Yellow solid (84% yield); m.p.>215° C. $^1$H NMR (500 MHz DMSO-$d_6$) δ 3.31 (s, 1H), 3.32 (s, 2H), 4.49 (s, 2H), 7.48 (d, 2H, J=8.1 Hz), 7.81 (d, 2H, J=5.3 Hz), 7.94 (d, 2H, J=8.1 Hz), 8.52 (s, 1H), 12.52 (s, 1H), 12.74 (s, 1H); $^{13}$C NMR (125 MHz DMSO-$d_6$) δ 57.77, 72.95, 110.36, 111.19, 120.96, 127.25, 127.82, 131.07, 132.11, 135.52, 142.97, 146.97, 153.65, 162.75; HRMS (ESI) m/z calcd for $C_{16}H_{14}Br_2N_2O_3H^+$: 440.9444, Found: 440.9448 (Δ=−0.88 ppm).

4-Dimethylamino-N'-(4-dibromo-2-hydroxybenzylidene)benzohydrazide (A16)

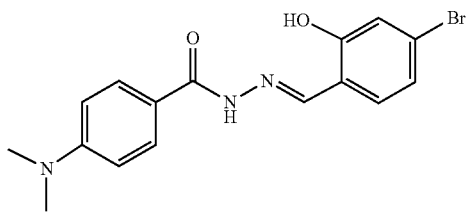 [SMILES: CN(C)c1ccc(C(=O)N/N=C/c2ccc(Br)cc2O)cc1]

Yellow solid (93% yield); m.p. 195-196° C.; $^1$H NMR (400 MHz DMSO-$d_6$) δ 2.99 (s, 6H), 6.75 (d, 2H, J=9 Hz), 7.09 (dd, 1H, J=8.24, 1.8 Hz), 7.12 (s, 1 h), 7.47 (d, 1H, J=8.3 Hz), 7.81 (d, 2H, J=9 Hz), 8.55 (s, 1H), 11.76 (s, 1H), 11.85 (s, 1H); $^{13}$C NMR (100 MHz DMSO-$d_6$) δ 110.84, 118.55, 119.04, 122.27, 123.38, 129.14, 130.65, 145.41, 152.62, 158.03, 162.57; HRMS (ESI) m/z calcd for $C_{16}H_{16}BrN_3O_2H^+$: 362.0499, Found: 362.0504 (Δ=−1.37 ppm).

3,5-Dibromo-2-hydroxy-N'-(5-methyl-2-hydroxyphenylmethylidene)benzohydrazide (A17)

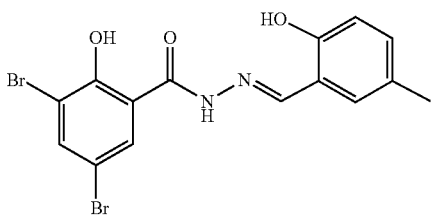 [SMILES: Cc1ccc(O)c(/C=N/NC(=O)c2cc(Br)cc(Br)c2O)c1]

Yellow solid (88% Yield), m.p 148-153° C.; $^1$H NMR (700 MHz. DMSO-d) δ 2.23 (s, 3H), 6.83 (d, 1H, J=8.3 Hz), 7.12 (dd, 1H, J=8.3, 1.9 Hz), 7.43 (s, 1H), 8.01 (s, 1H), 8.19 (s, 1H), 8.67 (s, 1H), (s, 1H), 12.37 (s, 1H), 13.09 (s, 1H); $^{13}$C NMR (175 MHz DMSO-$d_6$) δ 19.96, 109.81, 112.41, 116.32, 116.57, 118.35, 128.08, 128.48, 129.119, 132.84, 138.74, 149.52, 155.39, 156.82, 164.17; MS (ESI) m/z 426.9 (M+1)$^+$ 3,5-Dibromo-2-hydroxy-N'-(4-bromo-2-hydroxybenzylidene)benzohydrazide (A18)

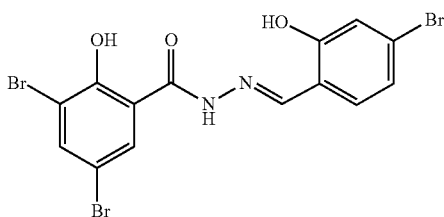 [SMILES: O=C(N/N=C/c1ccc(Br)cc1O)c1cc(Br)cc(Br)c1O]

Yellow solid (95% Yield); m.p>230° C.; $^1$H NMR (700 MHz DMSO-$d_6$) δ 7.10 (dd, 1H, J=8.3, 1.8 Hz), 7.12 (s, 1H), 7.62 (d, 1H, J=8.3 Hz), 8.00 (s, 1H), 8.17 (s, 1H), 8.68 (s, 1H), 11.17 (s, 1H), 12.41 (s, 1H); $^{13}$C NMR (175 MHz DMSO-$d_6$) δ 109.79, 112.46, 116.61, 118.59, 119.07, 122.61, 124.62, 129.22, 129.54, 138.76, 147.78, 156.83, 158.06, 164.24; MS (ESI) m/z 488.7 (M−1)$^-$ 3,5-Difluoro-N'-(4-bromo-2-hydroxybenzylidene)benzohydrazide (A19)

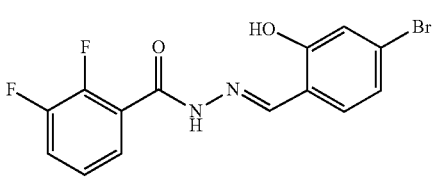 [SMILES: O=C(N/N=C/c1ccc(Br)cc1O)c1cccc(F)c1F]

White solid (87% yield); m.p. 222-228° C.; $^1$H NMR (400 MHz DMSO-$d_6$) δ 6.97 (d, 1H, 25%, J=8.3 Hz), 7.03 (s, 1H, 25%), 7.11 (d, 1H, 75%, 8.3 Hz), 7.19 (d, 1H, 25%, J=8.4 Hz), 7.30-7.37 (m, 2H, 25%, 100%), 7.49-7.51 (m, 1H, 75%), 7.58 (d, 1H, 75%, J=8.3 Hz), 7.60-7.66 (m, 2H, 100%, 75%), 8.30 (s, 1H, 26%), 8.52 (s, 1H, 74%), 10.41 (s, 1H, 30%), 11.22 (s, 1H, 70%), 12.16 (s, 1H, 100%); $^{13}$C NMR (100 MHz DMSO-$d_6$) δ 118.55, 118.80, 118.88, 119.05, 119.17, 119.87, 120.04, 122.52, 123.69, 124.23, 124.59, 124.81, 124.93, 125.27, 125.31, 127.94, 129.95, 141.79, 145.94, 146.09, 149.39, 148.52, 148.58, 150.97, 157.19, 157.96, 159.07, 165.38; $^{19}$F NMR. (376 MHz DMSO-$d_6$) δ −137.95 (d, 1F, J=23 Hz), −138.74 (d, 1F, J=23 Hz), −139.00 (d, 1F, 23 Hz), −139.94 (d, 1F, J=23 Hz); MS (ESI) m/z 352.9 (M−1)$^-$ 3,5-Difluoro-N'-(5-chloro-2-hydroxybenzylidene)benzohydrazide (A20)

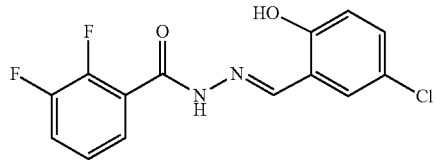 [SMILES: O=C(N/N=C/c1cc(Cl)ccc1O)c1cccc(F)c1F]

Brown solid (56% yield); m.p. 171-173° C.; $^1$H NMR (400 MHz DMSO-$d_6$) δ 6.85 (D, 1H, 25%, J=8.6 HZ), 6.94 (D, 1H, 75%, J=8.8 HZ), 7.20 (S, 1H, 15%), 7.21 (s, 1H, 40%), 7.30-7.37 (m, 3H, 100%, 25%, 60%), 7.48-7.52 (m, 1H, 75%), 7.55-7.58 (m, 1H, 15%), 7.60-7.64 (m, 1H, 85%), 7.67 (s, 1H, 85%), 8.29 (s, 1H, 25%), 8.51 (s, 1H, 75%), 10.25 (s, 1H, 20%), 11.01 (s, 1H, 80%), 12.22 (s, 1H, 100%); $^{13}$C NMR (100 MHz DMSO-$d_6$) δ 118.06, 118.24, 118.94, 119.12, 119.91, 120.08, 121.35, 123.03, 123.07, 124.64, 124.79, 124.90, 125.28, 125.38, 127.20, 130.68, 131.11, 141.07, 146.05, 155.25, 155.99, 159.16, 159.18; $^{19}$F NMR (376 MHz DMSO-$d_6$) δ −137.95 (d, 1F, J=23 Hz), −138.73 (d, 1F, J=23 Hz), −139.07 (d, 1F, J=23 Hz), −139.92 (d, 1F, J=23 Hz); MS (ESI) m/z 309.0 (M−1)$^-$ 4-Difluoromethoxy-N'-(4-bromo-2-hydroxybenzylidene)benzohydrazide (A21)

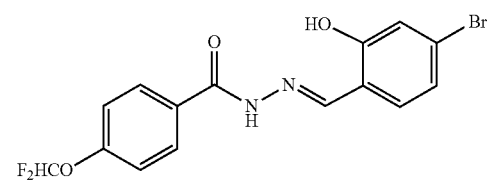 [SMILES: O=C(N/N=C/c1ccc(Br)cc1O)c1ccc(OC(F)F)cc1]

Yellow solid (96% yield); m.p. 195-200° C.; $^1$H NMR (400 MHz DMSO-$d_6$) δ 7.10-7.14 (m, 2H, 100%), 7.20 (s, 1H, 25%), 7.33 (d, 2H, J=0.5 Hz), 7.39, (s, 1H, 50%), 7.56 (d, 2H, 25%, 100%, J=7.4 Hz), 8.01 (d, 2H, 100% J=8.5 Hz), 8.62 (s, 1H, 100%), 11.49 (s, 1H, 100%), 12.14 (s, 1H, 100%); $^{13}$C NMR (100 MHz, DMSO-$d_6$) δ 113.46, 116.02, 118.07, 110.56, 118.59, 119.07, 122.43, 123.92, 129.31, 129.86, 130.31, 146.51, 158.03, 161.84; $^{19}$F NMR (376 MHz DMSO-$d_6$) δ −82.94 (s, 1F); HRMS (ESI) m/z calcd for $C_{10}H_{11}BrF_2N_2O_3H^-$: 384.9994, Found: 385.0007 (Δ=−3.49 ppm).

4-Difluoromethoxy-N'-(5-bromo-2-hydroxyben-
zylidene)benzohydrazide (A22)

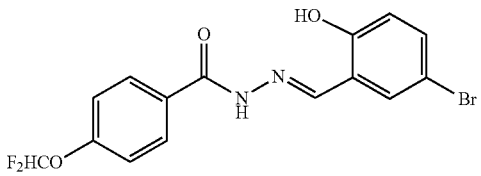 [SMILES: O=C(N/N=C/c1cc(Br)ccc1O)c1ccc(OC(F)F)cc1]

Beige solid (94% yield); m.p. 194-196° C.; $^1$H NMR (400 MHz DMSO 6) δ 6.90 (d, 1H, 100%, J=8.8 Hz), 7.20 (s, 1H, 25%), 7.33 (d, 2H, 100%, J=8.6), 7.39 (s, 1H, 50%), 7.43 (dd, 1H, 100%, J=8.8, 2.2 Hz), 7.57 (s, 1H, 25%), 7.80 (s, 1H, 100%), 8.01 (d, 2H, 100%, J=8.6 Hz), 8.61 (s, 1H, 100%), 11.26 (s, 1H, 100%), 12.19 (s, 1H, 100%); $^{13}$C NMR (100 MHz, DMSO-d$_6$) δ 110.45, 113.46, 116.03, 118.07, 110.60, 118.68, 121.32, 129.28, 129.90, 130.36, 133.60, 145.62, 153.68, 156.41, 161.94; $^{19}$F NMR (376 MHz DMSO-d$_6$) δ -82.94 (s, 1F) HRMS (ESI) m/z calcd for C$_{15}$H$_{11}$BrF$_2$N$_2$O$_3$H$^+$: 384.9994, Found: 305.0019 (Δ=-6.65 ppm).

4-Difluoromethoxy-N'-(3,5-dibromo-2-hydroxyben-
zylidene)benzohydrazide (A23)

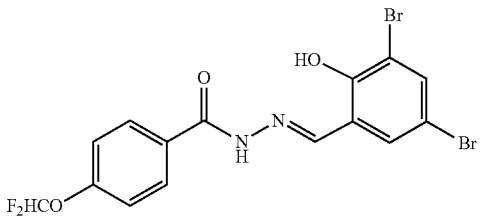 [SMILES: O=C(N/N=C/c1cc(Br)cc(Br)c1O)c1ccc(OC(F)F)cc1]

Beige solid (89% yield); m.p.>220° C.; $^1$H NMR (400 MHz DMSO-d$_6$) δ 7.21 (s, 1H, 25%), 7.35 (d, 2H, 100%, J=8.6 Hz), 7.40 (s, 1H, 50%), 7.58 (s, 1H, 25%), 7.83 (s, 2H, 100%), 8.03 (d, 2H, 100% J=8.7 Hz), 8.53 (s, 1H, 100%), 12.56 (s, 1H, 100%), 12.70 (s, 1H, 100%); $^{13}$C NMR (100 MHz, DMSO-d$_6$) δ 110.38, 111.21, 113.42, 115.99, 118.09, 120.95, 128.65, 130.04, 132.12, 135.58, 147.09, 153.66, 162.02; $^{19}$F NMR (376 MHz DMSO-d$_6$) δ -83.03 (s, 1F); HRMS (ESI) m/z calcd for C$_{15}$H$_{10}$Br$_2$F$_2$N$_2$O$_3$H$^+$: 462.9099, Found: 462.9103 (Δ=-0.92 ppm).

3-Trifluoromethyl-N'-(3-chloro-2-hydroxyben-
zylidene)benzohydrazide (A24)

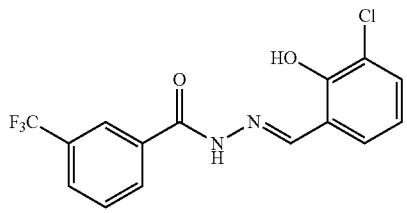

White solid (68% yield); $^1$H NMR (500 MHz, DMSO-d$_6$) δ 6.98 (t, J=7.8 Hz, 1H), 7.51 (m, 1H), 7.82 (t, J=7.0 Hz, 1H), 8.01 (d, J=7.0 Hz, 1H), 8.26 (d, J=7.9 Hz, 1H), 8.29 (s, 1H), 12.28 (s, 1H), 12.55 (s, 1H). $^{13}$C NMR (125 MHz, DMSO-d$_6$) δ 119.6, 120.1, 120.4, 124.2, 128.7, 129.2, 129.5, 130.0, 131.5, 131.9, 133.3, 149.2, 153.3, 161.5. $^{19}$F NMR (376 MHz, DMSO-d$_6$) δ -61.14 (s, 3H). MP>220° C. HRMS [M+H]$^+$ calcd for C$_{15}$H$_{11}$ClF$_3$N$_2$O$_2$$^+$: 343.0456, found: 343.0459 (Δ=-0.9 ppm). 3-Trifluoromethyl-N'-(3-bromo-2-hydroxybenzylidene)benzohydrazide (A25)

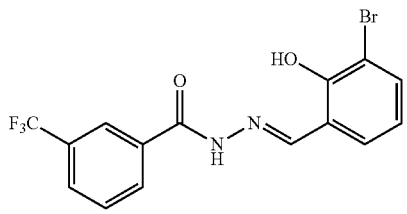 [SMILES: O=C(N/N=C/c1cccc(Cl)c1O)c1cccc(C(F)(F)F)c1]

White solid (72% yield); $^1$H NMR (400 MHz, DMSO-d$_6$) δ 6.93 (t, J=7.8 Hz, 1H), 7.55 (dd, J=7.7 Hz, J=1.4 Hz, 1H), 7.65 (dd, J=7.9 Hz, J=1.4 Hz, 1H), 7.82 (t, J=7.9 Hz, 1H), 8.02 (d, J=7.9 Hz, 1H), 8.26 (d, J=8.0 Hz, 1H), 8.29 (s, 1H), 8.60 (s, 1H), 12.49 (br s, 1H), 12.55 (br s, 1H). $^{13}$C NMR (125 MHz, DMSO-d$_6$) δ 110.0, 119.3, 120.6, 124.3, 125.3, 128.8, 130.0, 130.4, 132.0, 133.3, 134.5, 149.3, 154.2, 161.5. $^{19}$F NMR (376 MHz, DMSO-d$_6$) δ -61.14 (s, 3H). MP>220° C. HRMS [M+H]$^+$ calcd for C$_{15}$H$_{11}$BrF$_3$N$_2$O$_2$$^+$: 386.9951, found: 386.9946 (Δ=1.3 ppm).

3-Trifluoromethyl-N'-(4-bromo-2-hydroxyben-
zylidene)benzohydrazide (A26)

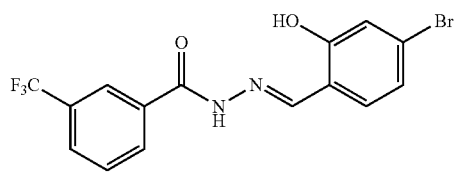 [SMILES: O=C(N/N=C/c1ccc(Br)cc1O)c1cccc(C(F)(F)F)c1]

White solid (73% yield); $^1$H NMR (400 MHz, DMSO-d$_6$) δ 7.13 (m, 2H), 7.60 (d, J=8.3 Hz, 1H), 7.80 (t, J=7.7 Hz, 1H), 7.99 (d, J=7.7 Hz, 1H), 8.24 (d, J=8.0 Hz, 1H), 8.28 (s, 1H), 8.66 (s, 1H), 11.37 (s, 1H), 12.28 (s, 1H). $^{13}$C NMR (125 MHz, DMSO-d$_6$) δ 110.6, 119.1, 122.5, 124.1, 120.5, 129.1, 129.9, 130.0, 131.9, 133.7, 146.7, 158.0, 161.4. $^{19}$F NMR (376 MHz, DMSO-d$_6$) δ -61.12 (s, 3H). MP>220° C. HRMS [M+H]$^+$ calcd for C$_{15}$H$_{11}$BrF$_3$N$_2$O$_2$$^+$: 386.9951, found: 306.9957 (Δ=-1.6 ppm).

3-Fluoro-N'-(3-bromo-2-hydroxybenzylidene)benzo-
hydrazide (A27)

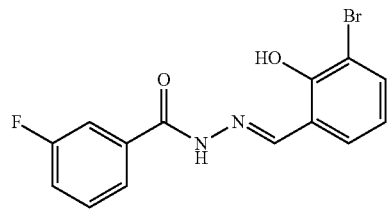 [SMILES: O=C(N/N=C/c1cccc(Br)c1O)c1cccc(F)c1]

White solid (73% yield); $^1$H NMR (700 MHz, DMSO-d$_6$) δ 6.92 (t, 1H, 75%, J=7.8 Hz), 6.99 (t, 1H, 25%, J=7.8 Hz), 7.50 (td, 1H, 75%, J=8.5 Hz, J=2.2 Hz), 7.54 (d, 1H, 75%, J=7.6 Hz), 7.61-7.65 (m, 2H, 75%, 100%), 7.75-7.77 (m, 2H, 25%, 75%), 7.81 (d, 1H, 75%, J=7.7 Hz), 8.58 (s, 1H, 75%), 9.13 (s, 1H, 25%), 12.08 (br s, 1H, 25%), 12.45 (br s, 1H, 75%), 12.50 (s, 1H, 100%). $^{13}$C NMR (175 MHz, DMSO-d$_6$) δ 110.1, 110.1, 114.5, 114.6, 118.8, 119.1, 119.3, 119.3, 120.6, 121.1, 124.0, 124.0, 130.5, 130.9, 132.1, 134.5, 134.6, 134.7, 136.4, 149.1, 154.2, 155.3, 161.3, 161.6, 162.7, 165.1. $^{19}$F NMR (376 MHz, DMSO-d$_6$) δ −112.26 (td, J=5.6 Hz, J=, 9.2 Hz, 1F). MP=192-193° C. HRMS [M+H]$^+$ calcd for C$_{14}$H$_{11}$BrFN$_2$O$_2{}^+$: 386.9982, found: 386.9986 (Δ=−0.9 ppm).

3-Fluoro-N'-(4-bromo-2-hydroxybenzylidene)benzohydrazide (A28)

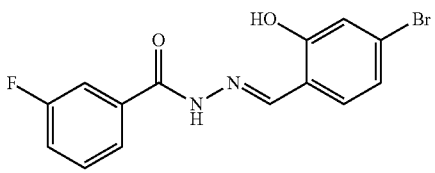 [SMILES: O=C(N/N=C/c1ccc(Br)cc1O)c1cccc(F)c1]

White solid (61% yield); $^1$H NMR (700 MHz, DMSO-d$_6$) δ 7.12 (d, 1H, 78%, J=7.8 Hz), 7.14-7.17 (m, 2H, 78%, 24%), 7.19 (s, 1H, 19%), 7.47 (td, 1H, 79%, J=2.0 Hz, J=8.5 Hz), 7.58-7.62 (m, 2H, 100%, 78%), 7.67 (d, 1H, 20%, J=8.3 Hz), 7.74 (d, 1H, 79%, J=9.7 Hz), 7.79 (d, 1H, 79%, J=7.7 Hz), 8.63 (s, 1H, 81%), 9.0 (s, 1H, 21%), 11.42 (s, 1H, 100%), 12.17 (s, 1H, 100%). $^{13}$C NMR (175 MHz, DMSO-d$_6$) δ 114.4, 114.5, 118.0, 118.6, 118.9, 119.0, 119.1, 119.3, 122.5, 121.8, 123.9, 123.9, 124.1, 126.1, 130.2, 130.8, 131.5, 135.1, 135.1, 136.7, 158.0, 159.2, 161.3, 161.3, 161.6, 162.6. $^{19}$F NMR (376 MHz, DMSO-d$_6$) δ −112.41 (td, J=6.0 Hz, J=9.4 Hz, 1F). MP=201-202° C. HRMS [M+H]$^+$ calcd for C$_{14}$H$_{11}$BrFN$_2$O$_2{}^+$: 386.9982, found: 386.9985 (Δ=−0.8 ppm).

3,4-Dibromo-N'-(3,5-dibromo-2-hydroxybenzylidene)benzohydrazide (A29)

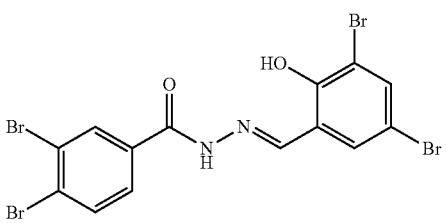 [SMILES: O=C(N/N=C/c1cc(Br)cc(Br)c1O)c1ccc(Br)c(Br)c1]

Yellow solid (78% yield); m.p. 225-230° C.; $^1$H NMR (400 MHz, DMSO-d$_6$) δ 7.91-7.85 (m, 3H, 100%), 7.93-7.95 (m, 2H, 100%, 20%), 8.27 (s, 1H, 80%), 8.50 (s, 1H, 80%), 9.03 (s, 1H, 20%), 12.53 (s, 2H, 100%, 50%); $^{13}$C NMR (100 MHz, DMSO-d6) δ 110.48, 110.76, 111.30, 111.68, 120.37, 120.91, 124.28, 128.58, 132.53, 133.45, 135.77, 137.77, 147.64, 153.65, 154.75, 160.86, 163.95; HRMS (ESI) m/z calcd for C$_{14}$H$_8$Br$_4$N$_2$O$_2$: 552.7391, Found: 552.7392 (Δ=0.18 ppm).

3,4-Dibromo-N'-(3,5-dichloro-2-hydroxybenzylidene)benzohydrazide (A30)

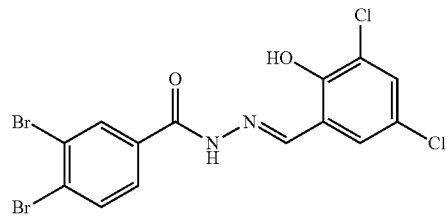 [SMILES: O=C(N/N=C/c1cc(Cl)cc(Cl)c1O)c1ccc(Br)c(Br)c1]

Yellow solid (64% yield); m.p. 210-215° C.; $^1$H NMR (400 MHz, DMSO-d$_6$) δ 7.63 (d, 1H) 7.69 (d, 1H) 7.84 (dd, 1H) 7.97 (d, 1H) 8.29 (s, 1H) 8.55 (s, 1H) 12.35 (d, 2H) $^{13}$C NMR (125 MHz, DMSO-d6) δ 120.77, 121.99, 123.03, 124.29, 128.36, 128.58, 130.47, 133.05, 134.16, 147.48, 152.24, 160.86, 163.54; HRMS (ESI) m/z calcd for C$_{14}$H$_8$Br$_2$Cl$_2$N$_2$O$_2$: 464.8404, Found: 464.8402 (Δ=−0.32 ppm).

3,4-Dibromo-N'-(5-chloro-2-hydroxybenzylidene)benzohydrazide (A31)

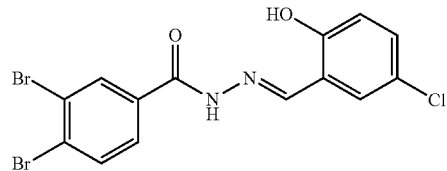

Light yellow solid (35% yield); m.p.>230° C.; $^1$H NMR (400 MHz, DMSO-d$_6$) δ 6.95 (d, 1H, 60%, J=8.8 Hz), 7.00 (d, 1H, 40%, J=8.8 Hz), 7.32 (dd, 1H, 60%, J=8.8, 2.6 Hz), 7.41 (dd, 1H, J=8.8, 2.6 Hz), 7.68 (d, 1H, 60%, J=2.5 Hz), 7.77 (d, 1H, 40%, J=2.6 Hz), 7.85 (dd, 1H, 65%, J=8.3, 1.7 Hz), 7.95 (d, 1H, 60%, J=8.3 Hz), 8.29 (s, 1H, 65%), 8.62 (s, 1H, 60%), 8.94 (s, 1H, 40%), 11.13 (s, 1H, 100%), 12.25 (s, 1H, 60%); $^{13}$C NMR (125 MHz, DMSO-d$_6$) δ 118.21, 118.47, 119.94, 120.70, 123.11, 124.19, 127.22, 128.01, 128.51, 131.00, 132.44, 133.59, 134.06, 146.06, 155.98, 157.24, 160.83; HRMS (ESI) m/z calcd for C$_{14}$H$_9$Br$_2$ClN$_2$O$_2$: 430.8812, Found: 430.8792 (Δ=−4.51 ppm).

3,4-Dibromo-N'-(2-hydroxy-1-naphthylidene)benzohydrazide (A32)

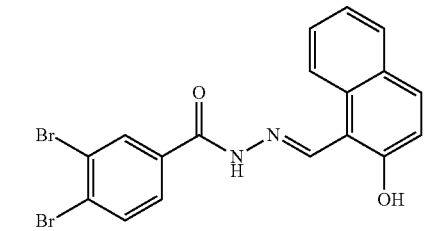 [SMILES: O=C(N/N=C/c1c(O)ccc2ccccc12)c1ccc(Br)c(Br)c1]

Dark yellow solid (66% yield); m.p.>230° C.; $^1$H NMR (400 MHz, DMSO-d$_6$) δ 7.22 (d, 1H, 85%, J=9 Hz), 7.7.27

(d, 1H, 15%, J=9 Hz), 7.40 (t, 1H, 100%, J=7.5 Hz), 7.60 (t, 1H, 100%, J=7.6 Hz), 7.87-7.89 (m, 2H, 85%, 85%), 7.93 (d, 1H, 100%, J=9 Hz), 7.98 (d, 1H, 85%, J=8.3 Hz), 8.02 (d, 1H, 15%, J=8.3 Hz), 8.28 (d, 1H, 85%, J=8.6 Hz), 8.32 (s, 1H, 85%), 8.63 (d, 1H, 15%, J=8.6 Hz), 9.44 (s, 1H, 85%), 9.97 (s, 1H, 15%), 12.28 (s, 1H, 85%), 12.55 (s, 1H, 85%), 12.86 (s, 1H, 10%); $^{13}$C NMR (100 MHz, DMSO-$d_6$) δ 108.55, 118.85, 120.91, 123.64, 124.33, 127.89, 128.12, 129.01, 131.60, 132.39, 133.05, 134.23, 147.57, 158.12, 160.35; HRMS (ESI) m/z calcd for $C_{18}H_{11}Br_2N_2O_2$: 446.934, Found: 446.9338 (Δ=−0.46 ppm).

3,4-Dibromo-N'-(5-bromo-2-hydroxybenzylidene) benzohydrazide (A33)

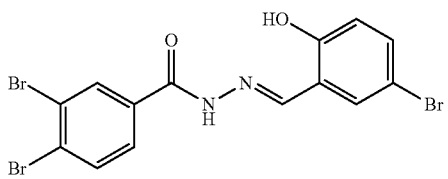

Light yellow, cream solid (53% yield); m.p.>230° C.; $^1$H NMR (400 MHz, DMSO-$d_6$) δ 6.89 (d, 1H, 65%, J=8.8 Hz), 6.94 (d, 1H, 35%, J=8.8 Hz), 7.42 (dd, 1H, 65%, J=8.7, 2.3 Hz), 7.52 (dd, 1H, 35%, J=8.8, 2.4 Hz), 7.80 (s, 1H, 65%), 7.83 (d, 1H, 70%, J=8.3 Hz), 7.88 (s, 1H, 35%), 7.94 (d, 1H, 70%, J=8.3 Hz), 8.28 (s, 1H, 70%), 8.60 (s, 1H, 65%), 8.92 (s, 1H, 35%), 11.13 (s, 1H, 100%), 12.23 (s, 1H, 60%); $^{13}$C NMR (100 MHz, DMSO-$d_6$) δ 110.38, 118.73, 121.15, 124.02, 128.35, 129.91, 132.28, 133.44, 133.61, 145.72, 156.23, 157.48, 160.56; HRMS (ESI) m/z calcd for $C_{14}H_9Br_3N_2O_2$: 474.8288, Found: 474.8287 (Δ=−0.19 ppm).

3,4-Dibromo-N'-(2-hydroxy-5-methylbenzylidene) benzohydrazide (A34)

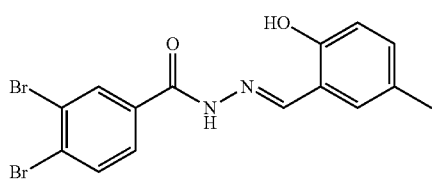 [SMILES: Cc1ccc(O)c(/C=N/NC(=O)c2ccc(Br)c(Br)c2)c1]

White solid (94% yield); m.p. 212-216° C.; $^1$H NMR (400 MHz DMSO-$d_6$) δ 2.24 (s, 3H), 6.82 (d, 1H, 55%, J=8.3 Hz), 6.86 (d, 1H, J=8.3 Hz), 7.10 (d, 1H, 55%, J=8.2 Hz), 7.19 (d, 1H, 45%, J=8.3 Hz), 7.36 (s, 1H, 55%), 7.47 (s, 1H, 45%), 7.83 (d, 1H, 60%, J=8.3 Hz), 7.94 (d, 2H, 30%, 30%, J=8.3 Hz), 8.27 (s, 1H, 60%), 8.58 (s, 1H, 55%), 8.91 (s, 1H, 45%), 10.84 (s, 1H, 60%), 10.90 (s, 1H, 40%), 12.15 (s, 1H, 50%); $^{13}$C NMR (100 MHz, DMSO-$d_6$) δ 116.38, 118.36, 124.19, 128.14, 128.49, 132.42, 148.46, 155.28, 156.49, 160.54, 162.47; HRMS (ESI) m/z calcd $C_{15}H_{11}Br_2N_2O_2$: 410.9343, Found: 410,9338 (Δ=−1.25 ppm).

3,4-Dibromo-N'-(4-bromo-2-hydroxybenzylidene) benzohydrazide (A35)

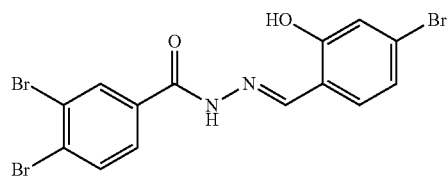 [SMILES: O=C(N/N=C/c1ccc(Br)cc1O)c1ccc(Br)c(Br)c1]

Off-white solid (63% yield); m.p.>230° C.; $^1$H NMR (400 MHz, DMSO-$d_6$) δ 7.08-7.18 (m, 2H, 100%, 100%), 7.57 (d, 1H, 80%, J=8.3 Hz), 7.65 (d, 2H, 20%, 20%, J=8.3 Hz), 7.83 (dd, 1H, 80%, J=8.3, 1.9 Hz), 7.94 (d, 1H, 80%, J=8.3 Hz), 8.27 (s, 1H, 80%), 8.61 (s, 1H, 75%), 8.94 (s, 1H, 25%), 11.33 9 s, 1H, 100%), 12.18 (s, 1H, 75%); $^{13}$C NMR (100 MHz, DMSO-$d_6$) δ 118.60, 122.49, 124.11, 126.08, 128.48, 130.02, 132.42, 146.74, 157.99, 160.61; HRMS (ESI) m/z calcd for $C_{14}Br_4N_2O_2$: 474.8286, Found: 474.8287 (Δ=0.16 ppm).

3,5-Dibromo-N'-(5-bromo-2-hydroxybenzylidene) benzohydrazide (A36)

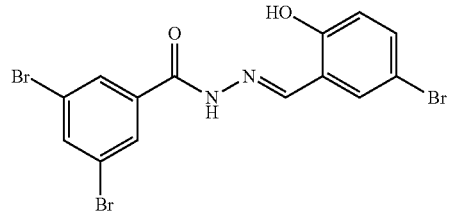

White solid (58% yield); m.p.>230° C.; $^1$H NMR (400 MHz, DMSO-$d_6$) δ 6.90 (d, 1H, J=8.8 Hz), 7.43 (dd, 1H, J=8.8, 2.6 Hz), 7.82 (d, 1H, J=2.5 Hz), 8.11 (s, 3H), 8.61 (s, 1H), 11.10 (s, 1H), 12.25 (s, 1H); $^{13}$C NMR (100 MHz, DMSO-$d_6$) δ 110.52, 118.67, 121.33, 122.72, 129.60, 129.95, 136.40, 136.59, 145.99, 156.39; HRMS (ESI) m/z calcd for $C_{14}H_9Br_3N_2O_2$: 474.8288, Found: 474.8287 (Δ=−0.32 ppm).

3,5-Dibromo-N'-(2-hydroxy-1-naphthylidene)benzohydrazide (A37)

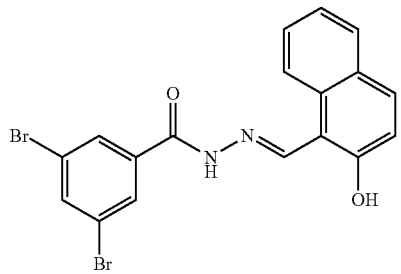 [SMILES: O=C(N/N=C/c1c(O)ccc2ccccc12)c1cc(Br)cc(Br)c1]

Yellow solid (42% yield); m.p.>230° C.; $^1$H NMR (700 MHz, DMSO-$d_6$) δ 7.24 (d, 1H, J=8.9 Hz), 7.42 (t, 1H, J=7.4 Hz), 7.62 (t, 1H, J=7.6 Hz), 7.90 (d, 1H, J=8 Hz), 7.95 (d, 1H, J=8.9 Hz), 8.14 (s, 1H), 8.16 (s, 2H), 8.32 (d, 1H, J=8.6 Hz), 9.44 (s, 1H), 12.31 (s, 1H), 12.50 (s, 1H); $^{13}$C NMR (175 MHz, DMSO-$d_6$) δ 108.54, 118.82, 120.99, 122.85, 123.63, 127.86, 127.90, 129.00, 129.56, 131.58, 133.12, 136.84, 136.69, 147.79, 158.15, 159.66; HRMS (ESI) m/z calcd for $C_{14}H_9Br_3N_2O_2$: 446.934, Found: 446.9338 (Δ=−0.34 ppm).

3,5-Dibromo-N'-(3,5-dichloro-2-hydroxybenzylidene)benzohydrazide (A38)

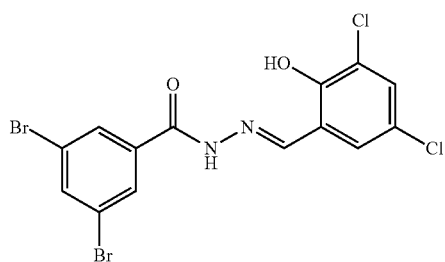 [SMILES: O=C(N/N=C/c1cc(Cl)cc(Cl)c1O)c1cc(Br)cc(Br)c1]

Tan solid (Quantitative yield); m.p.>230° C.; $^1$H NMR (400 MHz, DMSO-$d_6$) δ 7.63 (s, 1H), 7.69 (s, 2H), 8.11 (s, 2H), 8.12 (s, 1H), 8.56 (s, 1H), 12.25 (s, 1H), 12.61 (s, 1H); $^{13}$C NMR (100 MHz, DMSO-$d_6$) δ 120.78, 121.62, 122.81, 123.08, 128.34, 129.70, 130.55, 135.85, 136.91, 147.67, 152.23, 160.24; HRMS (ESI) m/z calcd for $C_{14}H_8Br_2Cl_2N_2O_2$: 446.9339, Found: 446.9338 (Δ=−0.19 ppm).

3,5-Dibromo-N'-(4-bromo-2-hydroxybenzylidene)benzohydrazide (A39)

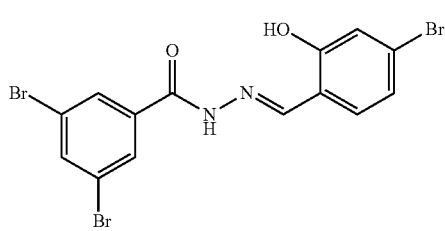 [SMILES: O=C(N/N=C/c1ccc(Br)cc1O)c1cc(Br)cc(Br)c1]

White solid (84% yield); m.p.>230° C.; $^1$H NMR (700 MHz, DMSO-$d_6$) δ 7.15 (d, 1H, J=8.3 Hz), 7.14 (s, 1H), 7.59 (d, 1H, J=8.3 Hz), 8.10 (s, 3H), 8.62 (s, 1H), 11.30 (s, 1H), 12.20 (s, 1H); $^{13}$C NMR (175 MHz, DMSO-$d_6$) δ 118.64, 119.06, 122.53, 122.76, 124.21, 129.60, 129.89, 136.46, 136.60, 146.81, 157.99, 159.98; HRMS (ESI) m/z calcd for $C_{14}H_9Br_3N_2O_2$: 474.8289, Found: 474.8287 (Δ=−0.42 ppm).

3,5-Dibromo-N'-(5-chloro-2-hydroxybenzylidene)benzohydrazide (A40)

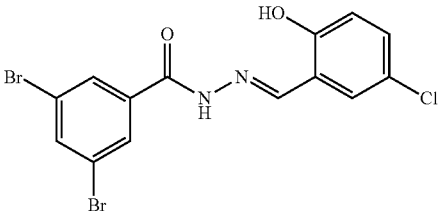 [SMILES: O=C(N/N=C/c1cc(Cl)ccc1O)c1cc(Br)cc(Br)c1]

White solid (92% yield); m.p.>230° C.; $^1$H NMR (700 MHz, DMSO-$d_6$) δ 6.95 (d, 1H, J=8.8 Hz), 7.33 (dd, 1H, J=8.8, 2.7 Hz), 7.69 (s, 1H), 8.11 (s, 3H), 8.62 (s, 1H), 11.09 (s, 1H), 12.25 (s, 1H); $^{13}$C NMR (175 MHz, DMSO-$d_6$) δ 118.24, 120.74, 122.76, 127.09, 129.62, 131.09, 136.41, 146.15, 156.00, 160.09; HRMS (ESI) calcd for $C_{14}H_9Br_2ClN_2O_2$: 430.8902, Found: 430.8792 (Δ=−2.34 ppm).

3,5-Dibromo-N'-(2-hydroxy-5-methylbenzylidene)benzohydrazide (A41)

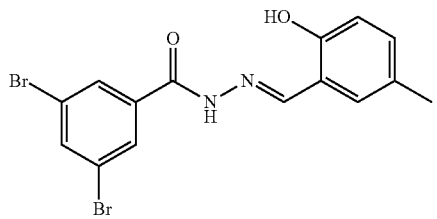 [SMILES: Cc1ccc(O)c(/C=N/NC(=O)c2cc(Br)cc(Br)c2)c1]

White solid (92% yield); m.p.>230° C.; $^1$H NMR (400 KHz, DMSO-$d_6$) δ 2.25 (s, 3H), 6.82 (d, 1H, J=8.2 Hz), 7.10 (dd, 1H, J=8.3, 1.8 Hz), 7.38 (s, 1H), 8.09 (s, 3H), 8.91 (s, 1H), 10.78 (s, 1H), 12.15 (s, 1H); $^{13}$C NMR (175 MHz, DMSO-$d_6$) δ 19.96, 116.29, 116.41, 117.88, 122.76, 128.00, 128.87, 129.64, 130.45, 131.22, 132.45, 133.95, 136.55, 148.56, 155.30, 156.52, 159.90, 162.50; HRMS (ESI) m/z calcd for $C_{15}H_{12}Br_2N_2O_2$: 410.9345, Found: 410.9338 (Δ=−1.65 ppm).

2,3-Dibromo-N'-(3,5-dibromo-2-hydroxybenzylidene)benzohydrazide (A42)

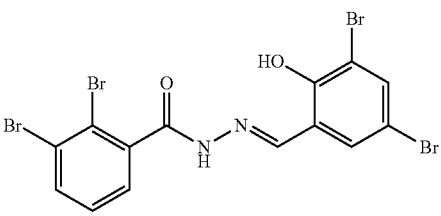 [SMILES: O=C(N/N=C/c1cc(Br)cc(Br)c1O)c1cccc(Br)c1Br]

White solid (98% yield); m.p. 227-230° C.; $^1$H NMR (400 MHz, DMSO-$d_6$) δ 7.42-7.46 (m, 2H, 30%, 100%), 7.56-7.58 (m, 2H, 70%, 30%), 7.74 (s, 1H, 25%), 7.82 (s, 1H, 75%), 7.84 (s, 1H, 70%), 7.88 (d, 1H, 20%), 7.90 (dd, 1H, 80%, J=7.9, 1.4 Hz), 8.21 (s, 1H, 25%), 8.38 (s, 1H, 75%), 10.30 (s, 1H, 25%), 12.32 (s, 1H, 75%), 12.47 (s, 1H, 35%), 12.60 (s, 1H, 65%); $^{13}$C, NMR (175 MHz, DMSO-d$_6$) δ 110.57, 111.54, 120.77, 120.93, 121.54, 121.83, 125.15, 125.45, 127.18, 128.14, 129.52, 129.74, 131.33, 132.14, 134.45, 135.17, 135.68, 135.93, 139.15, 139.70, 144.00, 147.75, 152.57, 153.63, 163.06, 168.31; HRMS (ESI) m/z calcd for C$_{15}$H$_8$Br$_4$N$_2$O$_2$: 552.7393, Found: 552.7392 (Δ=−0.19 ppm).

2,3-Dibromo-N'-(3,5-dichloro-2-hydroxybenzylidene)benzohydrazide (A43)

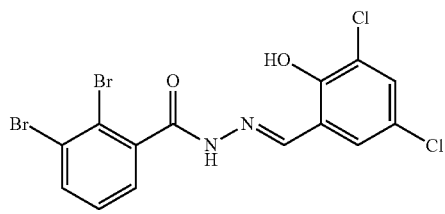 [SMILES: O=C(N/N=C/c1cc(Cl)cc(Cl)c1O)c1cccc(Br)c1Br]

Product washed with water and ~1 mL ethyl acetate, filtered, and washed with DCM and hexanes. Tan solid. (43% yield); m.p. 227-230 $^1$H NMR (500 MHz DMSO-d$_6$) δ 7.37 (d, 1H, 30%, 2.6 Hz), 7.42-7.46 (m, 3H, 30%, 70%, 30%), 7.53 (d, 1H, 30%, J=2.6 Hz), 7.57 (dd, 1H, 70%, J=7.6, 1.5 Hz), 7.64 (d, 1H, J=2.6 Hz), 7.68 (d, 1H, 70%, J=2.6 Hz), 7.89 (dd, 1H, 40%, J=6.7, 2.9 Hz), 7.91 (dd, 1H, 60%, J=8. 1.5 Hz), 8.25 (s, 1H, 30%), 8.42 (s, 1H, 70%), 10.27 (s, 1H, 30%), 12.08 (s, 1H, 70%), 12.45 (s, 1H, 30%), 12.56 (s, 70%); $^{13}$C NMR (125 MHz, DMSO-d$_6$) δ 120.84, 121.80, 123.15, 123.41, 125.03, 127.15, 128.28, 129.51, 130.61, 134.32, 135.07, 139.19, 139.87, 143.35, 147.30, 151.07, 152.16, 163.00, 168.35; MS (ESI) m/z 462.8 (M−1)$^-$ 4-Fluromethyl-N'-(3,5-dibromo-2-hydroxybenzylidene)benzohydrazide (A44)

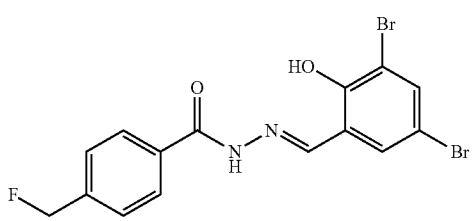 [SMILES: O=C(N/N=C/c1cc(Br)cc(Br)c1O)c1ccc(CF)cc1]

White solid (46% yield); m.p.>230° C.; $^1$H NMR (400 MHz DMSO-d$_6$) δ 5.46 (s, 1H), 5.58 (s, 1H), 7.57 (d, 2H, J=7.6 Hz), 7.80-7.82 (m, 2H), 7.99 (d, 2H, J=7.9 Hz), 8.53 (s, 1H), 12.56 (s, 1H), 12.71 (s, 1H); $^{13}$C NMR (100 MHz, DMSO-d$_6$) δ 82.71, 84.33, 110.39, 111.21, 120.95, 127.27, 127.33, 128.05, 132.13, 135.58, 140.40, 140.57, 147.17, 153.66, 162.61; $^{19}$F NMR (376 MHz DMSO-d$_6$) δ 209.61 (t, 1F, J=47.2 Hz); MS (ESI) m/z 428.9 (M+1)$^+$ 4-Azido-N'-(5-dibromo-2-hydroxybenzylidene)benzohydrazide (A45)

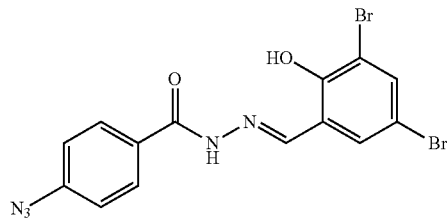 [SMILES: [N-]=[N+]=Nc1ccc(C(=O)N/N=C/c2cc(Br)cc(Br)c2O)cc1]

White solid (64% yield); m.p. 193-197° C.; $^1$H NMR (400 MHz DMSO-d$_6$) δ 7.28 (d, 2H, J=8.6 Hz), 7.79-7.81 (m, 2H), 8.00 (d, 2H, J=8.6 Hz), 8.51 (s, 1H), 12.53 (s, 1H), 12.71 (s, 1H); $^{13}$C NMR (100 MHz, DMSO-d$_6$). δ 110.39, 111.21, 119.26, 120.98, 128.45, 129.74, 132.11, 135.55, 143.53, 146.99, 153.65, 162.05.

4-Ethynyl-N'-(3,5-dibromo-2-hydroxybenzylidene)benzohydrazide (A46)

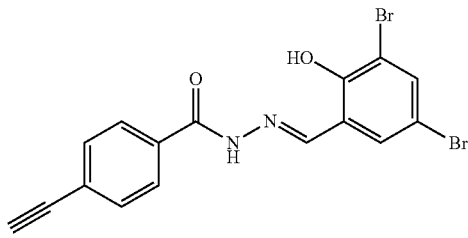 [SMILES: C#Cc1ccc(C(=O)N/N=C/c2cc(Br)cc(Br)c2O)cc1]

Yellow solid (55% yield); m.p.>230° C.; $^1$H NMR (300 MHz DMSO-d$_6$) δ 4.46 (s, 1H), 7.39 (d, 1H, J=7.9 Hz), 7.65 (d, 1H, J=8.4 Hz), 7.80-7.96 (m, 4H), 8.52 (s, 1H), 12.48-12.66 (m, 2H) MS (ESI) m/z 418.9 (M−1)$^-$ 4-Ethynyl-N'-(3,5-dibromo-2-hydroxybenzylidene)benzohydrazide (A47)

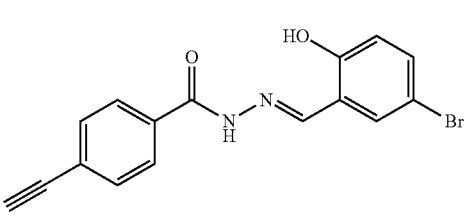 [SMILES: C#Cc1ccc(C(=O)N/N=C/c2cc(Br)ccc2O)cc1]

Yellow solid (75% yield); m.p.>230° C.; $^1$H NMR (300 MHz DMSO-d$_6$) δ 4.44 (s, 1H), 6.89 (d, 1H, J=3.7 Hz), 7.35-7.44 (m, 2H), 7.63 (d, 1H, J=8 Hz), 7.78-7.95 (m, 2H), 8.60 (s, 1H), 11.23-11.32)m, 1H), 12.13-12.24 (m, 1H); MS (ESI) m/z 340.9 (M−1$^-$ Chemical Synthesis and Characterization of Heteroaromatic Acylhydrazones of this Invention 5-Bromo-N'-(3,5-dibromo-2-hydroxybenzylidene)pyrimidine-2-carbohydrazide (H1)

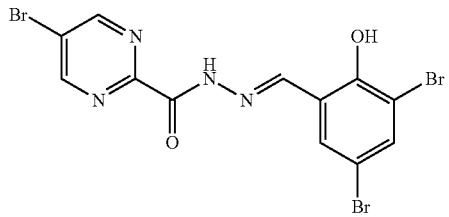 [SMILES: O=C(N/N=C/c1cc(Br)cc(Br)c1O)c1ncc(Br)cn1]

To a solution of 5-bromopyrimidine-2-carbohydrazide (50 mg, 0.23 mmol), 3,5-dibromo-2-hydroxybenzaldehyde (67 mg, 0.24 mmol) in methanol (5 mL) was added 1 drop of glacial acetic acid. The reaction mixture was stirred at room temperature overnight. Addition of water to the reaction mixture resulted in precipitation of the product, which was filtered, washed with water and dried under vacuum, to give pure product as white solid (95 mg, 86% yield: $^1$H NMR (700 MHz, DMSO-$d_6$) δ 7.73 (d, J=8.3, 2.2 Hz, 1H), 7.84 (t, J=3.1 Hz, 1H), 8.73 (s, 1H), 9.23 (s, 2H), 12.63 (br s, 1H), 13.06 (s, 1H). $^{13}$C NMR (175 MHz, DMSO-$d_6$) δ 110.5, 110.7, 111.3, 111.7, 120.4, 120.9, 122.9, 132.2, 133.4, 135.9, 137.8, 149.0, 153.8, 154.8, 154.9, 158.4, 158.5, 164.0. MP>220° C. HRMS [M+H]$^+$ calcd for $C_{12}H_8Br_3N_4O_2^+$ 476.8192, found 476.8183 (Δ=1.9 ppm).

The procedure detailed in the example above can be used for the synthesis of the following compounds.

5-Bromo-N'-(5-bromo-2-hydroxybenzylidene)thiophene-2-carbohydrazide (H2)

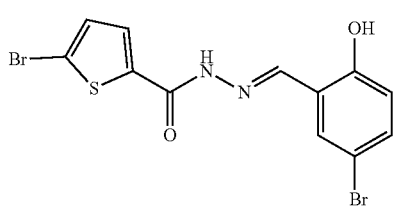 [SMILES: O=C(N/N=C/c1cc(Br)ccc1O)c1ccc(Br)s1]

White solid (85% yield); $^1$H NMR (500 MHz, DMSO-$d_6$) δ 6.90 (d, J=8.8 Hz, 1H), 7.43 (dd, J=8.8 Hz, J=2.4 Hz, 1H), 7.69 (d, J=1.1 Hz, 1H), 7.80 (d, J=2.4 Hz, 1H), 8.31 (d, J=1.1 Hz, 1H), 8.57 (s, 1H), 11.15 (s, 1H), 12.01 (s, 1H). $^{13}$C NMR (125 MHz, DMSO-$d_6$) δ 110.5, 112.5, 118.6, 121.4, 129.4, 130.1, 132.6, 133.6, 135.8, 145.2, 156.3, 157.2. MP: 210-211° C. HRMS [M+H]$^+$ calcd for $C_{12}H_9Br_2N_2O_2S^+$ 402.8746, found 402.0755 (Δ=-2.1 ppm).

5-Bromo-N'-(4-bromo-2-hydroxybenzylidene)thiophene-2-carbohydrazide (H3)

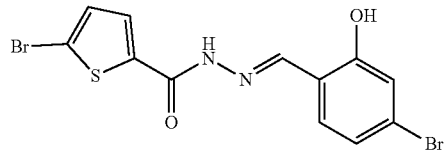 [SMILES: O=C(N/N=C/c1ccc(Br)cc1O)c1ccc(Br)s1]

White solid. (89 yield); $^1$H NMR (400 MHz, DMSO-$d_6$) δ 7.11 (m, 2H), 7.57 (d, J=8.2 Hz, 1H), 7.68 (d, J=1.2 Hz, 1H), 8.30 J=1.2 Hz, 1H), 8.58 (s, 1H), 11.35 (s, 1H), 11.95 (s, 1H). $^{13}$C NMR (100 MHz, DMSO-$d_6$) δ 112.5, 118.6, 119.0, 122.4, 123.9, 129.4, 130.0, 132.5, 135.8, 146.1, 157.2, 157.9. MP: 217-219° C. HRMS [M+H]$^+$ calcd for $C_{12}H_9Br_2N_2O_2S^+$ 402.8746, found 402.8757 (Δ=-2.9 ppm).

5-Bromo-N'-(3,5-dibromo-2-hydroxybenzylidene)thiophene-2-carbohydrazide (H4)

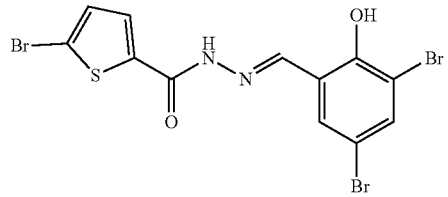 [SMILES: O=C(N/N=C/c1cc(Br)cc(Br)c1O)c1ccc(Br)s1]

White solid (91% yield); $^1$H NMR (500 MHz, DMSO-$d_6$) δ 7.69 (d, J=1.2 Hz, 1H), 7.83 (s, 2H), 8.34 (d, J=1.4 Hz, 1H), 8.48 (s, 1H), 12.40 (s, 1H), 12.56 (s, 1H). $^{13}$C NMR (125 MHz, DMSO-$d_6$) δ 110.4, 111.2, 112.8, 121.0, 129.4, 132.1, 133.2, 135.1, 135.6, 146.9, 153.6, 157.3. MP>220° C. HRMS [M+H]$^+$ calcd for. $C_{12}H_8Br_3N_2S^+$ 480.7851, found 480.7856 (Δ=-1.0 ppm).

5-Bromo-N'-((2-hydroxynaphthalen-1-yl)methylene)thiophene-2-carbohydrazide (H5)

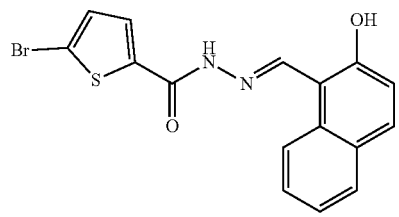 [SMILES: O=C(N/N=C/c1c(O)ccc2ccccc12)c1ccc(Br)s1]

White solid (78% yield); $^1$H NMR (700 MHz, DMSO-$d_6$) δ 7.23 (d, J=8.9 Hz, 1H), 7.41 (t, J=7.4 Hz, 1H), 7.61 (t, J=7.5 Hz, 1H), 7.71 (d, J=1.5 Hz, 1H), 7.90 (d, J=8.0 Hz, 1H), 7.94 (d, J=9.0 Hz, 1H), 8.28 (d, J=8.6 Hz, 1H), 8.33 (d, J=1.4 Hz, 1H), 9.40 (s, 1H), 12.07 (s, 1H), 12.57 (s, 1H). $^{13}$C NMR (125 MHz, DMSO-$d_6$) δ 108.6, 112.8, 118.9, 120.9, 123.6, 127.9, 129.0, 129.3, 131.6, 132.6, 132.9, 135.7, 146.7, 156.9, 158.0. MP: 197-198° C. HRMS [M+H]$^+$ calcd for $C_{16}H_{12}BrN_2O_2S^+$ 374.9797, found 374.9809 (Δ=-3.2 ppm).

5-Bromo-N'-(4-bromo-2-hydroxybenzylidene) nicotinohydrazide (H6)

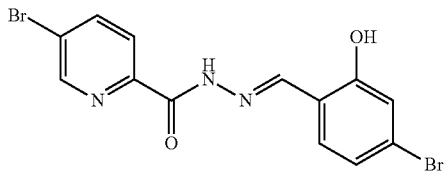 [SMILES: O=C(N/N=C/c1ccc(Br)cc1O)c1ccc(Br)cn1]

White solid (83% yield); $^1$H NMR (700 MHz, DMSO-$d_6$) δ 7.12 (dd, J=8.3 Hz, J=1.8 Hz, 1H), 7.14 (d, J=1.8 Hz, 1H), 7.61 (d, J=8.3 Hz, 1H), 8.51 (t, J=2.1 Hz, 1H), 8.62 (S, 1H), 8.92 (d, J=2.2 Hz, 1H), 9.04 (d, J=1.8 Hz, 1H), 11.28 (s, 1H), 12.27 (s, 1H). $^{13}$C NMR (175 MHz, DMSO-$d_6$) δ 118.6, 119.1, 120.1, 122.5, 124.3, 129.8, 130.3, 137.7, 146.8, 147.3, 153.1, 158.0, 160.0. MP>220° C. HRMS [M+H]$^+$ calcd for $C_{13}H_{10}Br_2N_3O_2^+$ 397.9134, found 397.9147 (Δ=−3.3 ppm).

4,5-Dibromo-N'-(5-bromo-2-hydroxybenzylidene)furan-2-carbohydrazide (H7)

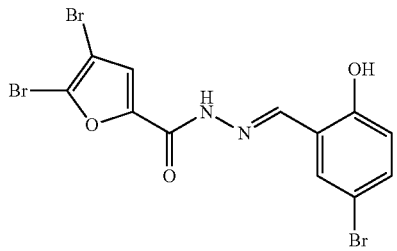 [SMILES: O=C(N/N=C/c1cc(Br)ccc1O)c1cc(Br)c(Br)o1]

White solid (67 yield); $^1$H NMR (700 MHz, DMSO-$d_6$) δ 6.89 (d, J=8.8 Hz, 1H), 7.43 (dd, J=8.7 Hz, J=2.4 Hz, 1H), 7.56 (s, 1H), 8.79 (d, J=2.2 Hz, 1H), 8.61 (s, 1H), 11.01 (s, 1H), 12.23 (s, 1H). $^{13}$C NMR (175 MHz, DMSO-$d_6$) δ 103.6, 110.5, 118.7, 119.2, 121.4, 127.2, 129.8, 133.8, 145.8, 148.1, 152.4, 156.3. MP>220° C. HRMS [M+H]$^+$ calcd for $C_{12}H_8Br_3N_2O_3^+$ 464.8080, found 464.8092 (Δ=−2.6 ppm).

4,5-Dibromo-N'-(4-bromo-2-hydroxybenzylidene)furan-2-carbohydrazide (H8)

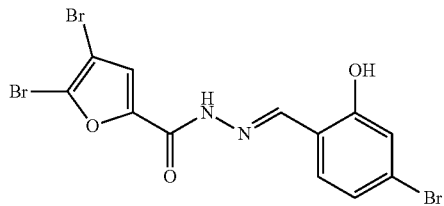 [SMILES: O=C(N/N=C/c1ccc(Br)cc1O)c1cc(Br)c(Br)o1]

White solid 73% yield); $^1$H NMR (400 MHz, DMSO-$d_6$) δ 7.10 (dd, J=8.2 Hz, J=1.8 Hz, 1H), 7.12 (d, J=1.7 Hz, 1H), 7.55 (s, 1H), 7.57 (d, J=8.3 Hz, 1H), 3.62 (s, 1H), 11.21 (s, 1H), 12.18 (s, 1H). $^{13}$C NMR (100 MHz, DMSO-$d_6$) δ 103.6, 118.7, 119.0, 119.1, 122.5, 124.1, 127.0, 129.7, 146.6, 148.1, 152.3, 157.9. MP>220° C. HRMS [M+H]$^+$ calcd for $C_{12}H_8Br_3N_2O_3^+$ 464.8080, found 464.8073 (Δ=1.5 ppm).

4,5-Dibromo-N'-(3,5-dibromo-2-hydroxybenzylidene)furan-2-carbohydrazide (H9)

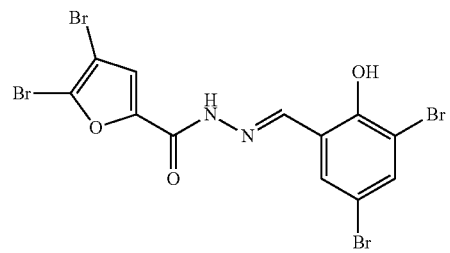 [SMILES: O=C(N/N=C/c1cc(Br)cc(Br)c1O)c1cc(Br)c(Br)o1]

White solid (79% yield); $^1$H NMR (700 MHz, DMSO-$d_6$) δ 7.60 (s, 1H), 7.81 (d, J=2.3 Hz, 1H), 7.84 (d, J=2.3 Hz, 1H), 8.53 (s, 1H), 12.38 (s, 1H), 12.66 (s, 1H). $^{13}$C NMR (125 MHz, DMSO-$d_6$) δ 103.8, 110.5, 111.4, 119.8, 121.0, 127.6, 132.0, 135.8, 147.6, 147.8, 152.4, 153.5, MP>220° C. HRMS [M+H]$^+$ calcd for $C_{12}H_7Br_4N_2O_3^+$ 542.7185, found 542.7190 (Δ=−0.9 ppm).

4,5-Dibromo-N'-(2-hydroxynaphthalen-1-yl)methylenefuran-2-carbohydrazide (H10)

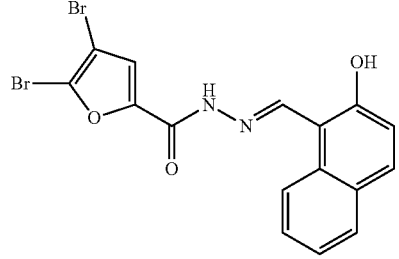 [SMILES: O=C(N/N=C/c1c(O)ccc2ccccc12)c1cc(Br)c(Br)o1]

White solid (77% yield); $^1$H NMR (400 MHz, DMSO-$d_6$) δ 7.23 (d, J=9.0 Hz, 1H), 7.41 (t, J=7.4 Hz, 1H), 7.59 (s, 1H), 7.61 (t, J=7.3 Hz, 1H), 7.90 (d, J=8.0 Hz, 1H), 7.94 (d, J=8.9 Hz, 1H), 8.29 (d, J=8.6 Hz, 1H), 9.48 (s, 1H), 12.30 (s, 1H), 12.41 (s, 1H). $^{13}$C NMR (100 MHz, DMSO-$d_6$) δ 103.9, 108.6, 118.8, 119.3, 121.0, 123.6, 127.0, 127.8, 128.9, 131.6, 133.1, 147.9, 148.1, 152.0, 158.0. MP>220° C. HRMS [M+H]$^+$ calcd for $C_{16}H_{11}Br_2N_2O_3^+$ 436.9131, found 436.9148 (Δ=−3.9 ppm).

4-Bromo-N'-(5-bromo-2-hydroxybenzylidene)furan-2-carbohydrazide (H11)

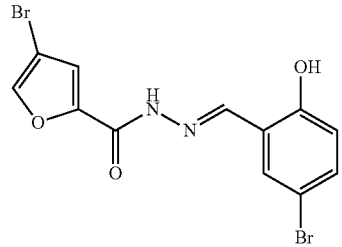 [SMILES: O=C(N/N=C/c1cc(Br)ccc1O)c1cc(Br)co1]

White solid. (67 yield); $^1$H NMR (700 MHz, DMSO-$d_6$) δ 6.90 (d, J=8.8 Hz, 1H), 7.43 (dd, J=8.7 Hz, J=2.1 Hz, 1H), 7.48 (s, 1H), 7.78 (s, 1H), 8.23 (s, 1H), 8.61 (s, 1H), 11.05 (s, 1H), 12.21 (s, 1H). $^{13}$C NMR (175 MHz, DMSO-$d_6$) δ 100.6, 110.5, 117.3, 118.6, 121.4, 130.0, 133.7, 144.4, 145.7, 146.9, 153.1, 156.3. MP: 203-205° C. HRMS [M+H]$^+$ calcd for $C_{22}H_9Br_2O_3^+$ 386.8974, found 386.8977 (Δ=−0.8 ppm).

4-Bromo-N'-(4-bromo-2-hydroxybenzylidene)furan-2-carbohydrazide (H12)

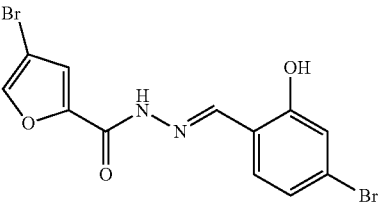 [SMILES: O=C(N/N=C/c1ccc(Br)cc1O)c1cc(Br)co1]

White solid (69% yield); $^1$H NMR (500 MHz, DMSO-$d_6$) δ 7.11 (m, 2H), 7.47 (s, 1H), 7.57 (d, J=8.3 Hz, 1H), 8.23 (d, J=0.6 Hz, 1H), 8.62 (s, 1H), 11.26 (s, 1H), 12.17 (s, 1H). $^{13}$C NMR (125 MHz, DMSO-$d_6$) δ 100.7, 117.3, 118.7, 119.0, 122.5, 124.1, 129.9, 144.4, 146.5, 146.9, 153.1, 157.9. MP>220° C. HRMS [M+H]$^+$ calcd for $C_{12}H_9Br_2N_2O_3^+$ 386.8974, found 386.8975 (Δ=−0.2 ppm).

4-bromo-N'-(3,5-dibromo-2-hydroxybenzylidene)furan-2-carbohydrazide (H13)

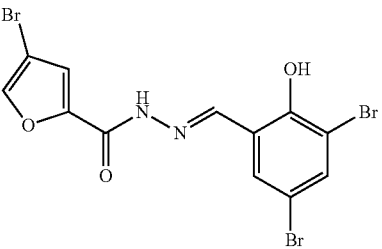 [SMILES: O=C(N/N=C/c1cc(Br)cc(Br)c1O)c1cc(Br)co1]

White solid (72% yield); $^1$H NMR (700 MHz, DMSO-$d_6$) δ 7.52 (s, H), 7.81 (d, J=2.0 Hz, 1H), 7.84 (d, J=2.4 Hz, 1H), 8.27 (s, 1H), 8.53 (s, 1H), 12.44 (s, 1H), 12.63 (s, 1H). $^{13}$C NMR (175 MHz, DMSO-$d_6$) δ 100.9, 110.5, 111.3, 118.0, 121.0, 132.1, 135.7, 144.8, 146.5, 147.6, 153.2, 153.6. MP=214-215° C. HRMS [M+H]$^+$ calcd for $C_{12}H_8Br_3N_2O_3^+$ 464.8080, found 463.8086 (Δ=−1.3 ppm).

N'-(4-bromo-2-hydroxybenzylidene)furan-3-carbohydrazide (H14)

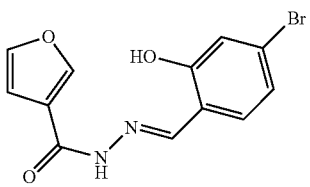 [SMILES: O=C(N/N=C/c1ccc(Br)cc1O)c1ccoc1]

White solid. (82% yield); $^1$H NMR (700 MHz, DMSO-$d_6$) δ 7.11 (dd, J=8.2 Hz, J=1.6 Hz, 1H), 7.14 (d, J=1.7 Hz, 1H), 7.56 (d, J=8.3 Hz, 1H), 7.60 (dd, J=5.0 Hz, J=1.0 Hz, 1H), 7.68 (dd, J=5.0 Hz, J=3.0 Hz, 1H), 8.32 (d, J=1.8 Hz, 1H), 8.59 (s, 1H), 11.48 (s, 1H), 11.97 (s, 1H). $^{13}$C NMR (175 MHz, DMSO-$d_6$) δ 118.6, 119.0, 122.4, 123.8, 126.8, 127.3, 130.2, 135.5, 145.8, 157.9, 158.4. MP>220° C. HRMS [M+H]$^+$ calcd for $C_{12}H_{10}BrN_2O_3^+$ 308.9869, found 308.9871 (Δ=−0.6 ppm).

N'-(3,5-dibromo-2-hydroxybenzylidene)tetrahydro-2H-pyran-4-carbohydrazide (H15)

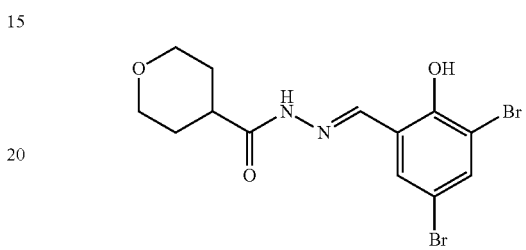

White solid (67% yield); $^1$H NMR (500 MHz, DMSO-$d_6$) δ 1.68 (s, 3H), 2.00 (s, 2H), 2.19 (s, 1H), 2.50 (s, 1H), 3.32-3.36 (m, 3H), 3.89 (d, 1H, J=2.2), 7.74-7.79 (m, 2H), 8.16-8.29 (m, 1H), 12.02 (s, 1H), 12.58 (d, 1H, J=3.97). $^{13}$C NMR (125 MHz, DMSO-$d_6$) δ 21.19, 28.49, 66.21, 111.03, 122.90, 132.04, 135.29, 140.97, 145.73, 153.47, 165.79, 171.45. MP>220° C. HRMS [M+H]$^+$ calcd for $C_{13}H_{15}Br_2N_2O_3^+$ 404.9444, found 404.9443 (Δ=0.2 ppm).

Example 8

In Vitro Activities ($MIC_{80}$ and $K_{100}$ of Acylhydrazones

In Vitro Susceptibility ($MIC_{80}$) Assay

MICs was determined following the methods of the Clinical and Laboratory Standards Institutes (CLSI) with modifications. Yeast Nitrogen Base (YNB) medium (pH 7.0, 0.2% glucose) buffered with HEPES was used for MIC studies. HEPES was used instead of morpholinepropanesulfonic acid (MOPS), because MOPS was found to inhibit the activity of this kind of compounds. The compound was serially diluted from 16 to 0.03 μg/ml, in a 96-well plate. The inoculum was prepared as described in the CLSI protocol M27A3 guidelines. The plates were incubated at 37° C. with 5% CO2 for 24 to 72 h and the optical density was measure at 450 nm. The MICs was determined as the lowest concentration of the compound that inhibited. 80% of growth compared to the control.

In Vitro Killing Activity ($K_{100}$) Assay

*C. neoformans* cells from a culture grown overnight were washed in PBS and resuspended in YNB buffered with HEPES at pH 7.4. The cells were counted, and 2×10$^4$ cells were incubated with different concentration of compounds in a final volume of 10 ml with a final concentration of 0.5% DMSO. The tubes were then incubated at 37° C. with 5% CO$_2$ on a rotary shaker at 200 rpm. Aliquots were taken at time points and diluted, and 100-1 portions were plated onto Yeast Extract-Peptone-Dextrose (YPD) plates. YPD plates were incubated in a 30° C. incubator and after 48 h, the numbers of CPU were counted and recorded.

TABLE 4

MIC$_{80}$ and killing activity (K$_{100}$) of aromatic acylhydrazones.

| Compound | MIC$_{80}$ (μg/mL) | K$_{100}$* (μg/mL) |
|---|---|---|
| A1 | 0.25 | >1 |
| A2 | 1 | >4 |
| A3 | 0.25 | 2 |
| A4 | 1 | >4 |
| A5 | 0.12 | Fungistatic |
| A6 | 0.12 | 0.5 |
| A7 | 0.5 | >4 |
| A8 | 0.5 | 1 |
| A9 | 0.12 | 0.5 |
| A10 | 0.25 | Fungistatic |
| A11 | 0.06 | >1 |
| A12 | 0.5 | 0.5 |
| A13 | 0.06 | 0.5 |
| A14 | 0.5 | >2 |
| A15 | 0.007 | 0.03 |
| A16 | 0.25 | >1 |
| A17 | 0.25 | 0.25 |
| A18 | 0.25 | 0.25 |
| A19 | 0.5 | 0.25 |
| A20 | 1 | 0.5 |
| A21 | 0.12 | — |
| A22 | 0.25 | — |
| A23 | 0.12 | — |
| A24 | 1 | 4 |
| A25 | 1 | 2 |
| A26 | 0.5 | 1 |
| A27 | 1 | 2 |
| A28 | 0.5 | >2 |
| A29 | 0.06 | >0.5 |
| A30 | <0.03 | >0.025 |
| A31 | 0.06 | >0.5 |
| A32 | 0.12 | >1 |
| A33 | 0.25 | 2 |
| A34 | 0.12 | >1 |
| A35 | 0.06 | >5 |
| A36 | 0.06 | >5 |
| A37 | 0.25 | 0.5 |
| A38 | 0.5 | 0.5 |
| A39 | 1 | 1 |
| A40 | 0.12 | 1 |
| A41 | 0.5 | 1 |
| A42 | 0.5 | 0.5 |
| A43 | 1 | 1 |
| A44 | 0.5 | 0.5 |
| A45 | 0.06 | — |
| A46 | 0.12 | Fungistatic |
| A47 | 0.12 | 0.12 |

*The minimum concentration of a compound that kills 100% of C. neoformans cells in 48 h.

TABLE 5

MIC$_{80}$ and killing activity (K$_{100}$) of heteroaromatic acylhydrazones.

| Compound | MIC$_{80}$ (μg/mL) | K$_{100}$* (μg/mL) |
|---|---|---|
| H1 | 0.25 | >2 |
| H2 | 0.12 | >0.5 |
| H3 | 0.12 | >0.5 |
| H4 | 0.06 | >0.25 |
| H5 | 0.12 | >0.5 |
| H6 | 1 | >4 |
| H7 | 0.25 | >1 |
| H8 | 0.06 | >0.25 |
| H9 | 0.12 | >0.5 |
| H10 | 0.12 | >0.5 |
| H11 | 0.25 | >1 |
| H12 | 0.5 | >2 |
| H13 | 0.06 | >0.25 |
| H14 | 0.5 | >1 |
| H15 | 0.5 | >2 |

*The minimum concentration of a compound that kills 100% of C. neoformans cells in 48 h.

Example 9

In Vivo Efficacy Evaluation (Survival Study) of Compound A15 in an Animal Model

Figure 2:
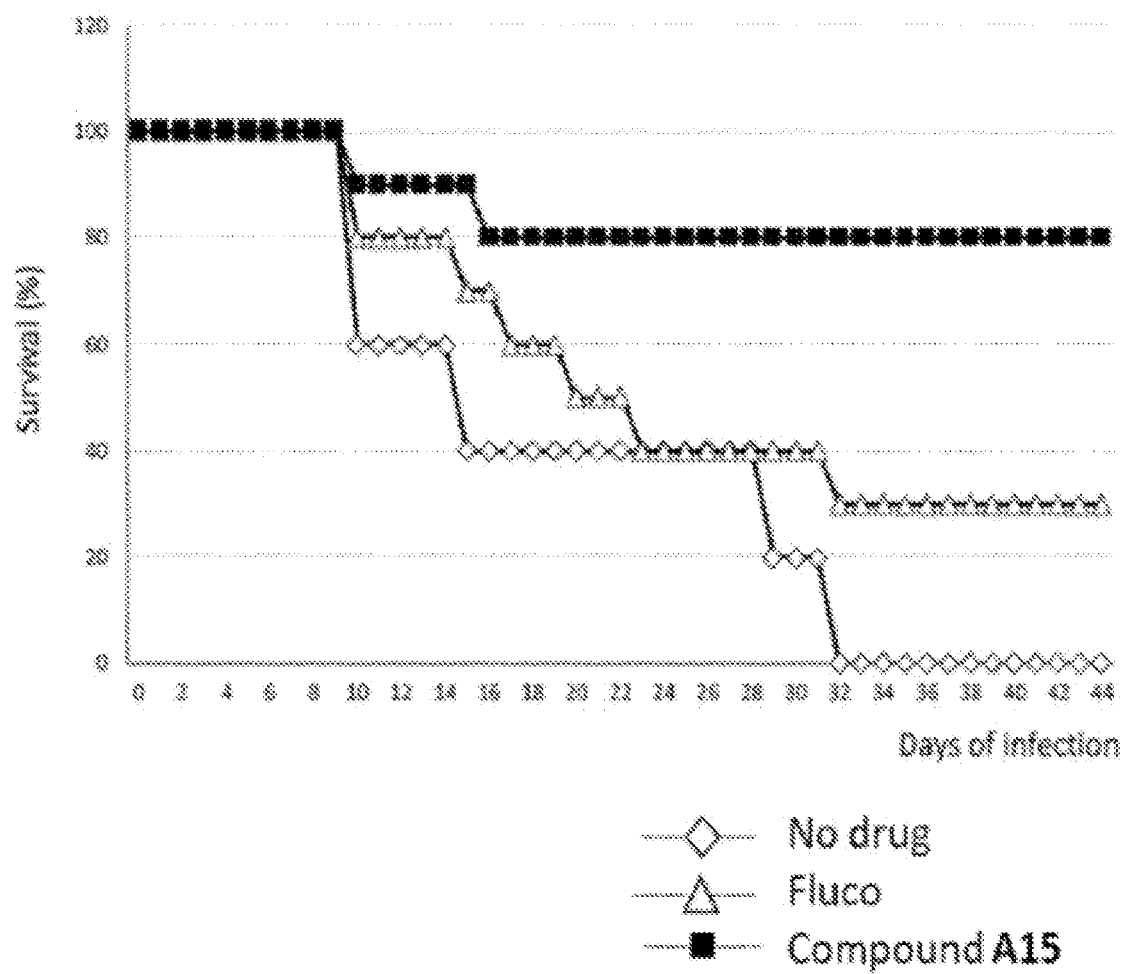
FIG. 2. In vivo efficacy evaluation (survival study) of compound A15 in an animal model.

For survival study, 4-week old CBA/J (Envigo) le mice were used. They were divided as ten mice for each treatment or control group. Mice were infected intranasally with 20 μl of a suspension containing 5×10$^5$ C. neoformans cells and subsequently treated orally with 20 mg/kg/day of compound A15 and fluconazole as drug control in a final volume of 100 μl of PEG30% in a saline buffer. The untreated control group mice received 100 μl of PEG30% in a saline buffer. Gavage was used as route of administration. At the end of the experiment, 80% of the mice treated with compound A15 survived whereas, only 30% of the mice treated with fluconazole survived. Mice were fed ad libitum and monitored every day for discomfort and meningitis signs. Mice showing weight loss, lethargy, tremor or inability to reach food or water were sacrificed and survival was counted until that day (see FIG. 2).

Discussion

The compounds described herein potent killing activity with low or no toxicity that can be used alone or in combination of current antifungal agents to treat superficial or invasive fungal infections.

A particular challenge with the discovery of antifungal drugs is toxicity due to the similarities between the fungal and human eukaryotic genomes. In exploring potential therapeutic targets, it became apparent that fungal sphingolipid pathways are quite distinct from human sphingolipid pathways. In addition, it is well established that the sphingolipid pathway is involved in the virulence of clinically important pathogenic fungi including *Cryptococcus neoformans* (Cn). Work from our lab and others showed that fungal sphingolipid complex, glucosylceramide (GlcCer), has increased expression on the fungal membrane in a lung infection model, GlcCer is critical in maintaining fungal cell membrane integrity and represents an attractive therapeutic target. In addition, it is well-established that gene deletion of glucosylceramide synthase (Gcs1) results in the creation of a *C. neoformans* strain, Δgcs1, that does not cause morbidity or mortality in a mouse model of CM. Moreover, Δgcs1 fungi exhibit deficient growth in vitro at a pH of >7, a similar pH to that found in the extracellular alveolar space in the lung where Cn thrives 10 and is the predominant first site of infection.

There is a major clinical need for new drugs due to a dramatic increase of morbidity and mortality by invasive fungal infections. Without being limited by a particular theory, the compounds contained herein decrease the synthesis of fungal but not mammalian GlcCer. This action seems to be specific to the transport of fungal ceramide species. The compounds are active in vitro against fungi, especially *C. neoformans, P. murina, P. jiroveci, R. oryzae*, and dimorphic fungi. The compounds appear to be effective in vivo against cryptococcosis, candidiasis and also against pneumocystosis. The compounds do not induce resistance in vitro and they are synergistic with existing antifungals.

*C. albicans* is resistant in vitro but not in vivo. Studies performed in this fungus have suggested that GlcCer is important for virulence but through a mechanism other than facilitating growth at neutral/alkaline pH, which is the pH used to screen our ChemBridge library. Hence, inhibition of GlcCer in *C. albicans* does not block fungal growth in vitro.

However, because the compound still decreases GlcCer synthesis, which is required for *Candida* virulence, the treatment is effective in partially protecting mice from invasive candidiasis. These findings support previous studies suggesting that the effect of GlcCer in vivo during *Candida* infection goes beyond the regulation of fungal alkaline tolerance.

The compounds disclosed herein inhibit GlcCer synthesis; however, this lipid is most likely not the only target of these compounds. In fact, the blockage of fungal growth in alkaline pH due to the loss of GlcCer (Δgcs1 mutant) can be restored if Δgcs1 cells are shifted to an acidic environment (Singh A. et al. 2012). This can occur even after the cells are left in cell cycle arrest for 72 hours. This means that the lack of GlcCer has a "static" effect on cell growth. However, the compounds disclosed herein kill fungal cells. One explanation for this effect is that treatment with the compound acutely leads to the accumulation of sphingosines, which is highly toxic to fungal cells (Chung, N. et al, 2001; Chung, N. et al. 2000). The accumulation of sphingosine species is not present when Gsc1 is deleted (Rittershaus, P. C. 2006) or in mammalian cells treated with compound. Thus, the effect seems to go beyond the inhibition of GlcCer and this may account for the fungal killing effect exerted by the compounds and not by the absence of GlcCer.

In summary, molecules were identified that target the synthesis of fungal but not mammalian GlcCer. These hydrazycins have potent antifungal in vitro and in vivo against a variety of clinically important fungi. They also displayed synergistic action with current antifungals, low toxicity, favorable PK parameters, and fungal specific mechanisms of action.

REFERENCES

Aerts A M, et al. The antifungal activity of RsAFP2, a plant defensin from *Raphanas sativas*, involves the induction of reactive oxygen species in *Candida albicans*. *J Mol Microbiol Biotechnol*. 2007; 13 (4):243-7.

Bligh E G, and Dyer W J. A rapid method for total lipid extraction and purification. *Can J Bioch Physiol*. 1959; 37; 911-7.

Brown G D, Denning D W, Gow N A, Levitz S M, Netea M G, and White T C. Hidden killers: human fungal infections. *Sci Transl Med*. 2012; 4 (165):165rv13.

Carmona E M, and Limper A H. Update on the diagnosis and treatment of *Pneumocystis pneumonia*. *Ther Adv Respir Dis*. 2011; 5 (1):41-59.

Chamilos G, Lewis R E, and Kontoyiannis D P. Lovastatin has significant activity against zygomycetes and interacts synergistically with voriconazole. *Antimicrob Agents Chemother*. 2006; 50 (1):96-103.

Chung N, Mao C, Heitman J, Hannun Y A, and Obeid L M. Phytosphingosine as a specific inhibitor of growth and nutrient import in *Saccharomyces cerevisiae*. *J Biol Chem*. 2001; 276 (38):35614-21.

Chung N, and Obeid L M. Use of yeast as a model system for studies of sphingolipid metabolism and signaling. *Methods Enzymol*. 2000; 311 (8):319-31.

da Silva A F, et al. Glucosylceramides in *Colletotrichum gloeosporioides* are involved in the differentiation of conidia into mycelial cells. *FEBS Lett*. 2004; 561 (1-3): 137-43.

DePristo, M. A., et al. A framework for variation discovery and genotyping using next-generation DNA sequencing data. Nature genetics 43, 491-490 (2011).

Del Poeta M, Nimrichter L, Rodrigues M L, and Luberto C. Synthesis and biological properties of fungal glucosylceramide. *PLoS Pathog*. 2014; 10 (1):e1003832.

Del Poeta M, et al. Synergistic antifungal activities of bafilomycin A(1), fluconazole, and the pneumocandin MK-0991/Caspofungin acetate (L-743, 873) with calcineurin inhibitors FK506 and L-685,818 against *Cryptococcus neoformans*. *Antimicrob Agents Chemother*. 2000; 44 (3):739-46.

Farowski F, et al. Intracellular concentrations of micafungin in different cellular compartments of the peripheral blood. *Int J Antimicrob Agents*. 2012; 39 (3):228-31.

Farowski F, et al. Intracellular concentrations of anidulafungin in different compartments of the peripheral blood. *Int J Antimicrob Agents*. 2013; 41 (4):379-82.

Funato K, and Riezman H. Vesicular and nonvesicular transport of ceramide from ER to the Golgi apparatus in yeast. *J Cell Biol*. 2001; 155 (6):949-59.

Fungal Infection Trust, How common are fungal diseases? *Fungal Research Trust 20th Anniversary Meeting*. Fungal Infection Trust; London). Jun. 18, 2011, updated December 2012.

Guery B P, et al. Management of invasive candidiasis and candidemia in adult non-neutropenic intensive care unit patients: Part I. Epidemiology and diagnosis. *Intensive Care Med*. 2009; 35 (1):55-62.

Gullo A. Invasive fungal infections: the challenge continues. *Drugs*. 2009; 69 Suppl 1, 65-73.

Heung L J, Luberto C, and Del Poeta M. Role of sphingolipids in microbial pathogenesis. *Infect Immun*. 2006; 74 (1):28-39.

Heung, L. J., Kaiser, A. E., Luberto, C. & Del Poeta, M. The role and mechanism of diacylglycerol-protein kinase C1 signaling in melanogenesis by *Cryptococcus neoformans*. J. Biol. Chem. 280, 28547-28555 (2005).

Hoffman. C. S., Winston, F. A ten-minute DNA preparation from yeast efficiently releases autonomous plasmids for transformation of *Escherichia coli*. Gene 57:267-272 (1987).

Hua, Z. & Graham, T. R. Requirement for neo1p in retrograde transport from the Golgi complex to the endoplasmic reticulum. Molecular biology of the cell 14, 4971-4983 (2003).

Huang L, Morris A, Limper A H, Beck J M, and Participants ATSPW. An Official ATS Workshop Summary: Recent advances and future directions in *Pneumocystis pneumonia* (PCP). *Proc Am Thorac Soc*. 2006; 3 (8):655-64.

Huang Z, et al. A functional variomics tool for discovering drug-resistance genes and drug targets. *Cell Rep*. 2013; 3 (2):577-85.

Huang Z, et al. Sampangine inhibits heme biosynthesis in both yeast and human. *Eukaryot Cell*. 2011; 10 (11):1536-44.

Kajiwara K, et al. Osh proteins regulate COPII-mediated vesicular transport of ceramide from the endoplasmic reticulum in budding yeast. *J Cell Sci*. 2014; 127 (Pt 2):376-87.

Kazanjian P, et al. *Pneumocystis carinii* cytochrome b mutations are associated with atovaquone exposure in patients with AIDS. *J Infect Dis*. 2001; 183 (5):819-22.

Kechichian T B, et al. Depletion of alveolar macrophages decreases the dissemination of a glucosylceramide-deficient mutant of *Cryptococcus neoformans* in immunodeficient mice. *Infect Immun*. 2007; 75 (10):4792-8.

Kelley C F, et al. Trends in hospitalizations for AIDS-associated *Pneumocystis jirovecii* Pneumonia in the United States (1986 to 2005). *Chest.* 2009; 136 (1):190-197.

Lee A Y, et al. Mapping the cellular response to small molecules using chemogenomic fitness signatures. *Science.* 2014; 344 (6180):208-11.

Levery S B, et al. Disruption of the glucosylceramide biosynthetic pathway in *Aspergillus nidulans* and *Aspergillus fumigatus* by inhibitors of UDP-Glc:ceramide glucosyltransferase strongly affects spore germination, cell cycle, and hyphal growth. *FEBS Lett.* 2002; 525 (1-3): 59-64.

Li, R, et al. SOAP2: an improved ultrafast tool for short read alignment. BioInformatics 25:1966-1967 (2009).

Li, H. & Durbin, P. Fast and accurate short read alignment with. Burrows-Wheeler transform. Bioinformatics 25, 1754-1760 (2009).

Lobo D S, et al. Antifungal Pisum sativum defensin 1 interacts with Neurospora crassa cyclin F related to the cell cycle. *Biochemistry.* 2007; 46 (4):987-96.

Ma L, Borio L, Masur H, and Kovacs J A. *Pneumocystis carinii* dihydropteroate synthase but not dihydrofolate reductase gene mutations correlate with prior trimethoprim-sulfamethoxazole or dapsone use. *J Infect Dis.* 1999; 180 (6):1969-78.

Mandala S M, et al. The discovery of australifungin, a novel inhibitor of sphinganine N-acyltransferase from *Sporormiella australis*. Producing organism, fermentation, isolation, and biological activity. *J Antibiot (Tokyo).* 1997; 50 (4):339-43.

Mayr A, and Lass-Florl C. Epidemiology and antifungal resistance in invasive Aspergillosis according to primary disease: review of the literature. *Eur J Med Res.* 2011; 16 (4):153-7.

McKenna, A., et al. The Genome Analysis Toolkit: a MapReduce framework for analyzing next-generation DNA sequencing data. Genome research 20, 1297-1303 (2010).

Mello Ede, O., et. al. Functional expression and activity of the recombinant antifungal defensin PvDir from Phaseolus vulgaris L. (common bean) seeds. *BMC Biochem.* 2014; 15 (1):7.

Munoz P, Guinea J, Narbona M T, and Bouza E. Treatment of invasive fungal infections in immunocompromised and transplant patients: AmBiLoad trial and other new data. *Int J Antimicrob Agents.* 2008; 32 Suppl 2: S125-31.

Noble S M, French S, Kohn L A, Chen V, and Johnson A D. Systematic screens of a *Candida albicans* homozygous deletion library decouple morphogenetic switching and pathogenicity. *Nat Genet.* 2010; 42 (7):590-8.

Oura T, and Kajiwara S. *Candida albicans* sphingolipid C9-methyltransferase is involved in hyphal elongation. *Microbiology.* 2010; 156 (Pt 4):1234-43.

Oura T, and Kajiwara S. Disruption of the sphingolipid. Delta8-desaturase gene causes a delay in morphological changes in *Candida albicans. Microbiology.* 2008; 154 (Pt 12):3795-803.

Pagano R E, Sepanski M A, and Martin O C. Molecular trapping of a fluorescent ceramide analogue at the Golgi apparatus of fixed cells: interaction with endogenous lipids provides a trans-Golgi marker for both light and electron microscopy. *J Cell Biol.* 1989; 109 (5):2067-79.

Perlroth J, Choi B, and Spellberg B. Nosocomial fungal infections: epidemiology, diagnosis, and treatment. *Med Mycol.* 2007; 45 (4):321-46.

Rhome R, et al. Biosynthesis and immunogenicity of glucosylceramide in *Cryptococcus neoformans* and other human pathogens. *Eukaryot Cell.* 2007; 6 (10):1715-26.

Rhome R, et al. Surface localization of glucosylceramide during *Cryptococcus neoformans* infection allows targeting as a potential antifungal. *PLoS One.* 2011; 6 (1): e15572.

Rueping M J, eInvasive candidiasis and candidemia: from current opinions to future perspectives. *Expert Opin Investig Drugs.* 2009; 18 (6):735-48.

Ruping M J, Vehreschild J J, and Comely O A. Patients at high risk of invasive fungal infections: when and how to treat. *Drugs.* 2008; 68 (14):1941-62.

Saribas Z, Yurdakul P, Cetin-Hazirolan G, and Arikan-Akdagli S. Influence of serum on in vitro susceptibility testing of echinocandins for *Candida parapsilosis* and *Candida guilliermondii. Mycoses.* 2012; 55 (2):156-60.

Singh A, and Del Poeta M. Lipid signalling in pathogenic fungi. *Cellular microbiology.* 2011; 13 (2) 177-85.

Singh A, Na C, Silva L C, Prieto M, Futerman A H, Luberto C, and Del Poeta M. Membrane lipid topography controlled by sphingolipids regulates pathogenicity of *Cryptococcus neoformans. Cellular Microbiology.* 2012; 14 (4):500-16.

Singh J, Rimek D, and Kappe R. In vitro susceptibility of 15 strains of zygomycetes to nine antifungal agents as determined by the NCCLS M38-A microdilution method. Mycoses. 2005; 48 (4):246-50.

Sorrell T C, Chen S C-A, Phillips P, and Marr K A. In: Heitman J, Kozel T R, Kwon-Chung K J, Perfect J, and Casadevall A eds. *Cryptococcus: from human pathogen to model yeast.* Washington, DC: ASM; 2011:595-606.

Suzuki, Y., et al. Knocking out multigene redundancies via cycles of sexual assortment and fluorescence selection. Nature methods 8, 159-164 (2011).

Tavares P M, et al. In vitro activity of the antifungal plant defensin RsAFP2 against *Candida* isolates and its in vivo efficacy in prophylactic murine models of candidiasis. *Antimicrob Agents Chemother,* 2008; 52 (12):4522-5.

Thevissen K, et al. The plant defensin RsAFP2 induces cell wall stress, septin mislocalization and accumulation of ceramides in *Candida albicans. Mol Microbiol.* 2012; 84 (1):166-80.

Thevissen K. et al. Defensins from insects and plants interact with fungal glucosylceramides. *J Biol Chem.* 2004; 279 (6):3900-5.

Toledo M S, et al. Characterization of cerebroside: from the thermally dimorphic mycopathogen *Histoplasma capsulatum*: expression of 2-hydroxy fatty N-acyl (E)-Delta(3)-unsaturation correlates with the yeast-mycelium phase transition. *Glycobiology.* 2001; 11 (2):113-24.

Wesp, A., et al. End4p/Sla2p interacts with actin-associated proteins for endocytosis in *Saccharomyces cerevisiae*. Molecular biology of the cell 8, 2291-2306 (1997).

World Health Organization. World Malaria Report 2013—http://www.who.int/malaria/publications/world_malaria_report_2013/en/. Accessed Dec. 11, 2013.

World Health Organization. Global Tuberculosis Report 2013—http://www.who.int/tb/publications/global_report_en/. Accessed November 2013.

What is claimed is:

1. A method of inhibiting the growth of a fungus comprising contacting the fungus with an effective amount of the compound having the structure:

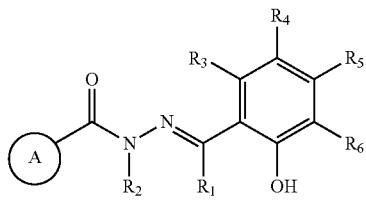

wherein $R_1$ is —H, alkyl, alkenyl, or alkynyl;

$R_2$ is —H, alkyl, alkenyl, or alkynyl;

$R_3$, $R_4$, $R_5$, and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, or $R_3$ and $R_4$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_5$ and $R_6$ combine to form a fused aryl or fused heteroaryl, which are each unsubstituted or substituted, or $R_3$ and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_4$ and $R_5$ combine to form a fused aryl or fused heteroaryl, which are each unsubstituted or substitute, or $R_5$ and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_3$ and $R_4$ combine to form a fused aryl or fused heteroaryl, which are each unsubstituted or substituted; and A is an aryl or heteroaryl, which are each unsubstituted or substituted, wherein when $R_3$, $R_4$, and $R_6$ are each —H and $R_5$ is —OH or —$OCH_3$, or $R_3$, $R_5$, and $R_6$ are each —H and $R_4$ is —Br, then A is other than ortho-tolyl or meta-bromophenyl, or a pharmaceutically acceptable salt or ester thereof, so as to thereby inhibit the growth of the fungus.

2. A method of inhibiting fungal sphingolipid synthesis in a fungus comprising contacting the fungus with an effective amount of the compound having the structure:

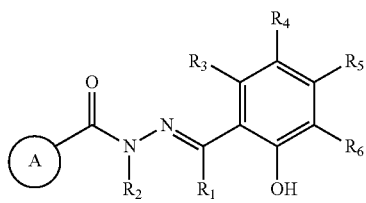

wherein $R_1$ is —H, alkyl, alkenyl, or alkynyl;

$R_2$ is —H, alkyl, alkenyl, or alkynyl;

$R_3$, $R_4$, $R_5$, and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, or $R_3$ and $R_4$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_5$ and $R_6$ combine to form a fused aryl or fused heteroaryl, which are each unsubstituted or substituted, or $R_3$ and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_4$ and $R_5$ combine to form a fused aryl or fused heteroaryl, which are each unsubstituted or substitute, or $R_5$ and $R_6$ are each independently —H, halogen, $C_1$-$C_6$ alkyl, —OH, —O—($C_4$-$C_6$ alkyl), —$CHF_2$, —$CF_3$, —$OCHF_2$ or —$OCF_3$, and $R_3$ and $R_4$ combine to form a fused aryl or fused heteroaryl, which are each unsubstituted or substituted; and A is an aryl or heteroaryl, which are each unsubstituted or substituted, wherein when $R_3$, $R_4$, and $R_6$ are each —H and $R_5$ is —OH or —$OCH_3$, or $R_3$, $R_5$, and $R_6$ are each —H and $R_4$ is —Br, then A is other than ortho-tolyl or meta-bromophenyl, or a pharmaceutically acceptable salt or ester thereof, so as to thereby inhibit sphingolipid synthesis in the fungus.

3. A method of inhibiting fungal sphingolipid synthesis in a fungus in a mammal without substantially inhibiting mammalian sphingolipid synthesis comprising administering to the mammal an effective amount of the compound of having the structure:

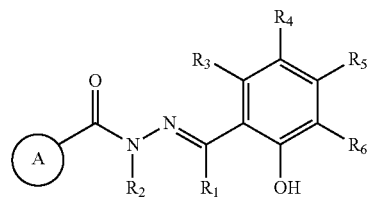

wherein $R_4$ is —H, alkyl, alkenyl, or alkynyl;

$R_2$ is —H, alkyl, alkenyl, or alkynyl;

$R_3$, $R_4$, $R_5$, and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, or $R_3$ and $R_4$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_5$ and $R_6$ combine to form a fused aryl or fused heteroaryl, which are each unsubstituted or substituted, or $R_3$ and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_4$ and $R_5$ combine to form a fused aryl or fused heteroaryl, which are each unsubstituted or substitute, or $R_5$ and $R_6$ are each independently —H, halogen, $C_1$-$C_6$ alkyl, —OH, —O—($C_1$-$C_6$ alkyl), —$CHF_2$, —$CF_3$, —$OCHF_2$ or —$OCF_3$, and $R_3$ and $R_4$ combine to form a fused aryl or fused heteroaryl, which are each unsubstituted or substituted; and A is an aryl or heteroaryl, which are each unsubstituted or substituted, wherein when $R_3$, $R_4$, and $R_6$ are each —H and $R_5$ is —OH or —$OCH_3$, or $R_3$, $R_5$, and $R_6$ are each —H and $R_4$ is —Br, then A is other than ortho-tolyl or meta-bromophenyl, or a pharmaceutically acceptable salt or ester thereof, so as to thereby inhibit fungal sphingolipid synthesis in the fungus in the mammal without substantially inhibiting mammalian sphingolipid synthesis.

4. The method of claim 1, wherein the compound has the structure:

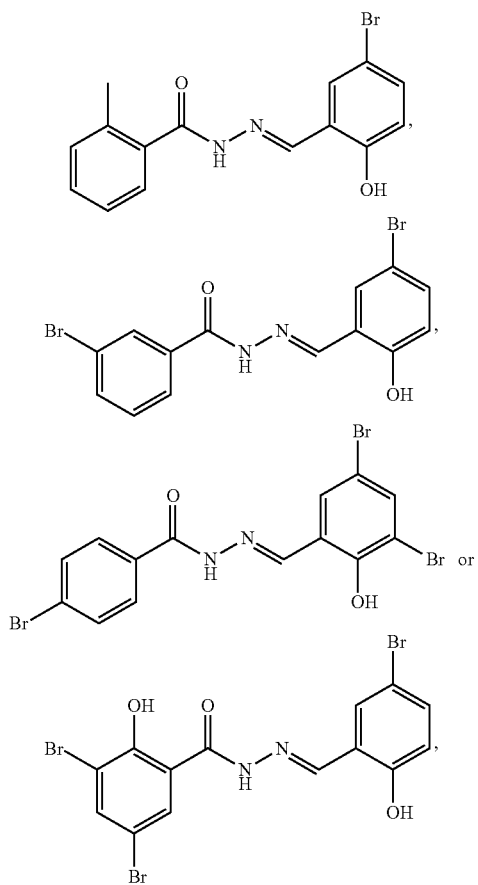

or a pharmaceutically acceptable salt thereof.

5. The method of claim 1, further comprising contacting the fungus with an effective amount of an anti-fungal agent.

6. The method of claim 3, further comprising administering to the mammal an effective amount of an anti-fungal agent.

7. The method of claim 6, wherein the amount of the compound and the amount of the anti-fungal agent when taken together is more effective to inhibit the growth of the fungus than the anti-fungal agent alone, or more effective to inhibit fungal sphingolipid synthesis than the anti-fungal agent alone.

8. The method of claim 6, wherein the amount of the compound and the amount of the anti-fungal agent when taken together is more effective to inhibit fungal sphingolipid synthesis without substantially inhibiting mammalian sphingolipid synthesis in the mammal than the anti-fungal agent alone.

9. The method of claim 5, wherein the anti-fungal agent is fluconazole, amphotericin B, caspofungin, tunicamycin or aureobasidin A.

10. The method of claim 1, wherein the fungus is Cryptococcus Neoformans, Cryptococcus gattii, Candida albicans, Candida krusei, Candida glabrata, Candida parapsilosis, Candida guilliermondii, Aspergillus fumigatus, Rhizopus oryzae, Rhizopus spp., Blastomyces dermatitis, Histoplasma capsulatum, Coccidioides spp., Paecilomyces variotii, Pneumocystis murina, Pneumocystis jiroveci, Histoplasma capsulatum, Aspergillus spp., dimorphic fungi or mucorales fungi.

11. The method of claim 1, wherein the fungus is other than Cryptococcus Neoformans.

12. The method of claim 1, wherein the fungus is Cryptococcus gattii, Candida albicans, Candida krusei, Candida glabrata, Candida parapsilosis, Candida guilliermondii, Aspergillus fumigatus, Rhizopus oryzae, Rhizopus spp., Blastomyces dermatitis, Histoplasma capsulatum, Coccidioides spp., Paecilomyces variotii, Pneumocystis murina, Pneumocystis jiroveci, Histoplasma capsulatum, Aspergillus spp., dimorphic fungi or mucorales fungi.

13. The method of claim 2, wherein the fungal sphingolipid is glucosylceramide (GlcCer).

14. The method of any claim 2, wherein the compound has the structure:

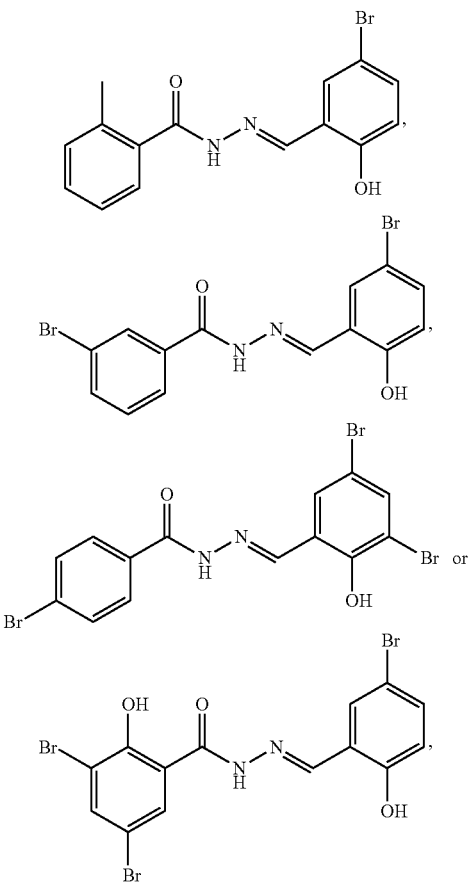

or a pharmaceutically acceptable salt thereof.

15. The method of claim 2, further comprising contacting the fungus with an effective amount of an anti-fungal agent.

16. The method of claim 2, wherein the anti-fungal agent is fluconazole, amphotericin B, caspofungin, tunicamycin or aureobasidin A.

17. The method of claim 2, wherein the fungus is Cryptococcus Neoformans, Cryptococcus gattii, Candida albicans, Candida krusei, Candida glabrata, Candida parapsilosis, Candida guilliermondii, Aspergillus fumigatus, Rhizopus oryzae, Rhizopus spp., Blastomyces dermatitis, Histoplasma capsulatum, Coccidioides spp., Paecilomyces variotii, Pneumocystis murina, Pneumocystis jiroveci, Histoplasma capsulatum, Aspergillus spp., dimorphic fungi or mucorales fungi.

18. The method of any claim 3, wherein the compound has the structure:

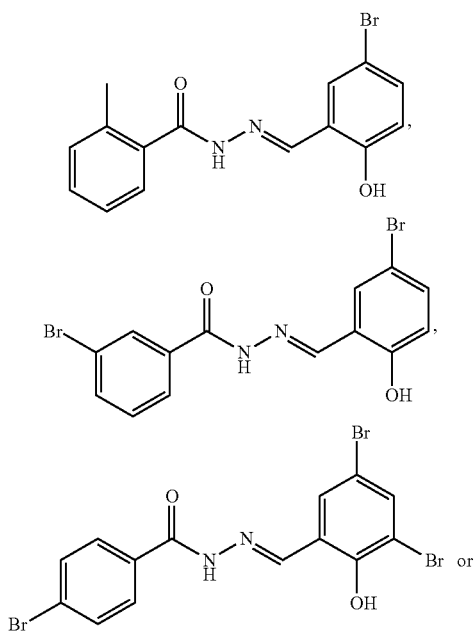

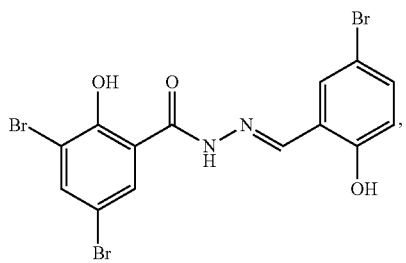

or a pharmaceutically acceptable salt thereof.

19. The method of claim 3, wherein the anti-fungal agent is fluconazole, amphotericin B, caspofungin, tunicamycin or aureobasidin A.

20. The method of claim 3, wherein the fungus is *Cryptococcus Neoformans, Cryptococcus gattii, Candida albicans, Candida krusei, Candida glabrata, Candida parapsilosis, Candida guilliermondii, Aspergillus fumigatus, Rhizopus oryzae, Rhizopus* spp., *Blastomyces* dermatitis, *Histoplasma capsulatum, Coccidioides* spp., *Paecilomyces variotii, Pneumocystis murina, Pneumocystis jiroveci, Histoplasma capsulatum, Aspergillus* spp., dimorphic fungi or mucorales fungi.

* * * * *